(12) United States Patent
McLoughlin et al.

(10) Patent No.: US 10,099,013 B2
(45) Date of Patent: Oct. 16, 2018

(54) INJECTOR

(71) Applicant: UCB BIOPHARMA SPRL, Brussels (BE)

(72) Inventors: Martin John McLoughlin, Berkshire (GB); Michael James David Heald, Berkshire (GB); Barry Alan Knight, Berkshire (GB); Dirushan Pillay, Berkshire (GB)

(73) Assignee: UCB Biopharma SPRL, Brussels (BE)

( * ) Notice: Subject to any disclaimer, the term of this patent is extended or adjusted under 35 U.S.C. 154(b) by 232 days.

(21) Appl. No.: 14/911,670

(22) PCT Filed: Aug. 11, 2014

(86) PCT No.: PCT/EP2014/067171
§ 371 (c)(1),
(2) Date: Feb. 11, 2016

(87) PCT Pub. No.: WO2015/022295
PCT Pub. Date: Feb. 19, 2015

(65) Prior Publication Data
US 2016/0193414 A1    Jul. 7, 2016

(30) Foreign Application Priority Data
Aug. 11, 2014 (GB) .................................. 1314381.3

(51) Int. Cl.
*A61M 5/24* (2006.01)
*A61M 5/31* (2006.01)
(Continued)

(52) U.S. Cl.
CPC ............ *A61M 5/3137* (2013.01); *A61M 5/24* (2013.01); *A61M 5/3158* (2013.01);
(Continued)

(58) Field of Classification Search
CPC .................. A61M 5/3137; A61M 5/24; A61M 2005/3139; A61M 2005/2407;
(Continued)

(56) References Cited

U.S. PATENT DOCUMENTS 1,685,984 A    10/1928    Jules et al.
2,118,221 A    5/1938    Montuori et al.
(Continued)

FOREIGN PATENT DOCUMENTS

DE    102012106437 A1    5/2013
WO    WO 03/015846 A2    2/2003
(Continued)

*Primary Examiner* — Theodore Stigell
*Assistant Examiner* — Hong-Van Trinh
(74) *Attorney, Agent, or Firm* — Muncy, Geissler, Olds & Lowe, P.C.

(57) ABSTRACT

Provided is a manual drive unit for use with a cassette unit comprising a cassette unit housing containing there within a syringe comprising a barrel for containing a volume of a liquid drug formulation; a hollow needle at a front end of the barrel, the hollow needle defining a needle tip for dispensing of the liquid drug formulation; and a plunger that is axially movable within the barrel. The manual drive unit comprises a manual drive unit housing defining a docking cavity and a needle delivery aperture, wherein said docking cavity is arranged for docking receipt of the cassette unit at a docking position; and received by the manual drive unit housing and axially movable relative thereto, a manually operable drive transfer element for transferring axial drive to the plunger of the syringe for moving the plunger into the barrel of the syringe to eject at least part of the volume of liquid drug formulation.

34 Claims, 50 Drawing Sheets

(51) Int. Cl.
*A61M 5/315* (2006.01)
*A61M 5/50* (2006.01)
*A61M 5/32* (2006.01)

(52) U.S. Cl.
CPC ...... *A61M 5/31515* (2013.01); *A61M 5/3204* (2013.01); *A61M 5/3213* (2013.01); *A61M 5/5086* (2013.01); *A61M 5/31505* (2013.01); *A61M 5/3202* (2013.01); *A61M 2005/244* (2013.01); *A61M 2005/2407* (2013.01); *A61M 2005/2418* (2013.01); *A61M 2005/2477* (2013.01); *A61M 2005/2481* (2013.01); *A61M 2005/2492* (2013.01); *A61M 2005/3139* (2013.01); *A61M 2205/584* (2013.01); *A61M 2205/586* (2013.01); *A61M 2205/6054* (2013.01)

(58) Field of Classification Search
CPC .. A61M 2005/2403; A61M 2005/2481; A61M 2005/2485; A61M 2005/2492; A61M 2205/586; A61M 5/3204; A61M 5/3213; A61M 5/3202; A61M 2005/2418; A61M 2005/312
See application file for complete search history.

(56) References Cited

U.S. PATENT DOCUMENTS

| | | | | |
|---|---|---|---|---|
| 5,334,162 A | * | 8/1994 | Harris | A61J 1/062 604/232 |
| 5,496,286 A | * | 3/1996 | Stiehl | A61M 5/24 604/232 |
| 2008/0097338 A1 | * | 4/2008 | Cheng | A61M 5/24 604/201 |
| 2009/0118679 A1 | * | 5/2009 | Ito | A61M 5/3135 604/232 |
| 2009/0182284 A1 | * | 7/2009 | Morgan | A61M 5/3137 604/198 |

FOREIGN PATENT DOCUMENTS

| | | | | |
|---|---|---|---|---|
| WO | WO 03/015846 A3 | 2/2003 | | |
| WO | WO 03015846 A2 | * 2/2003 | ............. | A61D 1/025 |
| WO | WO 2009/143255 A1 | 11/2009 | | |
| WO | WO 2012/145685 A1 | 10/2012 | | |
| WO | WO 2012/164397 A1 | 12/2012 | | |
| WO | WO 2014/020001 A1 | 2/2014 | | |
| WO | WO 2014/066256 A1 | 5/2014 | | |

\* cited by examiner

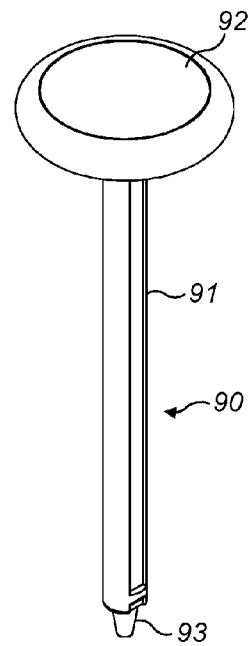
FIG. 19A
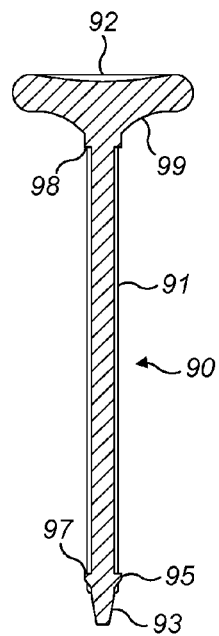 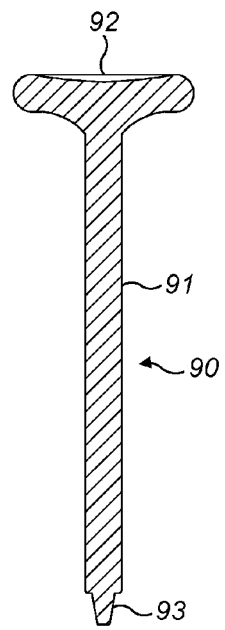
FIG. 19B　　　　FIG. 19C

INJECTOR

BACKGROUND

The present invention relates to an injector device for receipt of a syringe that is suitable for use in the injected delivery of a drug formulation to a patient and a manual drive unit therefor.

It is well-known to use syringes for the delivery of injectable liquid drug formulation to a patient. Syringes rely on puncturing of the patient's skin by a hollow needle through which the injectable liquid drug (e.g. in solution or suspension form) is delivered to the muscle or tissue of the patient. Typically, syringes comprise a barrel for containing a volume of the liquid drug; a hollow needle defining a needle tip for dispensing of the liquid; and a plunger that is axially movable within the barrel.

It is also known to provide manual injectors for use with syringes. Such injectors typically comprise a body for housing the syringe and a manual actuating mechanism, which is triggered in use, to allow for delivery of the liquid drug formulation from the syringe. Actuating mechanisms typically comprise a drive transfer element (e.g. a plunger rod) that transfers drive to the plunger for axial movement thereof within the syringe barrel. Such movement of the plunger results in the plunged driving of the liquid drug from the syringe barrel to the hollow needle for dispensing to the patient via the needle tip thereof.

Manual injectors are typically configured as a single device that incorporates both syringe and manually operable drive transfer element in the same device housing. It is common for such devices to be arranged to be disposable such that following injected delivery of the liquid drug formulation, and typically also following retraction of the syringe back into the housing, the whole device may be safely disposed of.

SUMMARY

It has been proposed to configure manual injectors to be particularly suitable for use by patients whose manual dexterity is so compromised (e.g. due to severe arthritis) that injecting by use of ordinary syringes is difficult. One such manual injector, which has a handhold arranged for ease of gripping by a patient's fingers and a readily removable needle tip cap, is described in PCT patent publication no. WO2009/090499 A2, the entire contents of which are incorporated herein by reference.

In some situations, it is undesirable for a manual injector to be fully disposable. Injectors disclosed herein, in certain embodiments, include both a re-useable manual drive unit comprising a drive transfer element and a cassette unit comprising a syringe, which releasably interfits with the manual drive unit and can be arranged to be disposable. Such injectors may be arranged to be 'environmentally friendly,' wherein the majority of components are retained to be used for further injection procedures. It also allows for the manual drive unit to be fitted with additional features such as those enabling ease of use for patients whose manual dexterity is compromised.

The manual drive unit includes a manual drive unit housing arranged for docking receipt of at least part of the cassette unit and a manually operable drive transfer element for transferring axial drive to the plunger of the syringe of the cassette unit for moving the plunger into the barrel of the syringe to eject at least part of the volume of liquid drug formulation.

The cassette unit comprises a cassette unit housing defining a cassette unit housing cavity and a needle projection aperture. The cassette unit housing cavity is arranged for receipt of a standard syringe, which typically comprises a barrel for containing a volume of a liquid drug formulation, a hollow needle at a front end of said barrel defining a needle tip for dispensing of the liquid drug formulation and a plunger that is axially movable within the barrel. Either the syringe or the cassette unit and syringe held thereby is movable within the manual drive unit housing from a rest position, in which the needle tip of the syringe is within the manual drive unit housing to a use position, in which the needle tip protrudes from a needle delivery aperture of the manual drive unit housing. In embodiments, the cassette unit is also provided with a removable cap that fits over and thereby, acts such as to close off, the needle projection aperture. In embodiments, connecting to the removable cap, there is also provided a needle cover defining a needle sheath arranged in a sheathing configuration for sheathing of said needle tip.

According to one aspect of the present invention there is provided a manual drive unit for use with a cassette unit comprising a cassette unit housing containing there within a syringe comprising a barrel; a hollow needle at a front end of said barrel; and a plunger that is axially movable within the barrel, the manual drive unit comprising:

a manual drive unit housing defining a docking cavity and a needle delivery aperture, wherein said docking cavity is arranged for docking receipt of said cassette unit at a docking position; and a manually operable drive transfer element for transferring axial drive to the plunger of the syringe for moving the plunger into the barrel of the syringe to eject at least part of said volume of liquid drug formulation.

According to another aspect of the present invention there is provided an injector comprising:

(a) a manual drive unit as described herein; and
(b) a cassette unit comprising:

a cassette unit housing defining a cassette unit housing cavity, a rearward entrance to said cavity and a forward needle projection aperture;

said cassette unit housing cavity in receipt of a syringe comprising:

a barrel for containing a volume of a liquid drug formulation, said barrel defining a flange at the rear end thereof and a forward shoulder at the forward end thereof;

a hollow needle at a front end of said barrel, said hollow needle defining a needle tip for dispensing of said liquid drug formulation; and a plunger that is axially movable within the barrel, wherein said plunger of the syringe is arranged for receipt of axial drive from the manually operable drive transfer element for moving the plunger into the barrel of the syringe to eject at least part of said volume of liquid drug formulation.

These and other embodiments are set forth in the later description, which describes for illustrative purposes only various embodiments thereof.

In relation to aspects of the injector device described herein the term 'forward' is used to mean that end of the device, which locates closest to the injection site in use (i.e. the needle tip end) and the term 'rear' or 'rearward' is used to mean that end of the device, which locates furthest from the injection site in use.

There is provided an injector that is arranged for use with a syringe that contains a liquid drug formulation. The syringe is arranged to be suitable for use in the injected delivery of the liquid drug formulation to a patient. The injector comprises both a manual drive unit and a cassette unit receivable by the manual drive unit. The individual manual drive unit and cassette unit parts thereof comprise further separate aspects of the present invention. In embodiments the manual drive unit and cassette unit are provided as a kit of parts.

Injectors comprising both a manual drive unit comprising an electrically powered source of axial drive and a cassette unit comprising a syringe, which releasably interfits with the manual drive unit already have been described in Applicant's PCT publications WO2012/164,390; WO2012/164,402; WO2012/164,404; WO2012/164,389; WO2012/164,397; WO2012/164,394; WO2013/001378; WO2012/164,406; WO2012/164,403; WO2014/020,001; WO2014/020,000; WO2014/019,999; and WO2014/019,997, the contents of all of which are incorporated by reference in their entirety and made part of this application.

Manual Drive Unit

There is provided a manual drive unit for use with a cassette unit. The cassette unit comprises a cassette unit housing containing there within a syringe comprising a barrel for containing a volume of a liquid drug formulation; a hollow needle at a front end of the barrel, the hollow needle defining a needle tip for dispensing of said liquid drug formulation; and a plunger that is axially movable within the barrel.

The manual drive unit comprises a manual drive unit housing defining a docking cavity and a needle delivery aperture, wherein the docking cavity is arranged for docking receipt of a cassette unit at a docking position. The docking cavity and receivable part of the cassette unit are correspondingly sized and shaped to facilitate the intended docking relationship.

The manual drive unit also comprises a manually operable drive transfer element for transferring axial drive to the plunger of the syringe for moving the plunger into the barrel of the syringe to eject at least part of the volume of liquid drug formulation. The drive transfer element is received by the manual drive unit housing and is axially movable relative thereto.

In use, axial drive force applied manually to the drive transfer element (e.g. plunger rod) results in drivable movement of the plunger within the syringe barrel of the syringe, ultimately to a fully plunged position when most, in embodiments all, of the liquid drug formulation contents of the syringe barrel have been drivably expelled therefrom.

In embodiments, the drive transfer element communicates directly with (e.g. contacts or abuts) the plunger of the syringe for transferring drive thereto. In embodiments, an end portion of the drive transfer element directly communicates with (e.g. contacts or abuts) the plunger. In other embodiments, the drive transfer element communicates indirectly with (e.g. via a slaving or coupling element) the plunger of the syringe for transferring drive thereto.

In embodiments, the manual drive unit housing defines a drive aperture for receipt of the drive transfer element.

In embodiments, the drive transfer element is provided with a first retaining feature arranged for retaining interaction with a second retaining feature of the manual drive unit housing such as to retain the drive transfer element in movable relationship to the manual drive unit housing. In embodiments, the retaining interaction acts to limit the extent of axial driving movement of the drive transfer element relative to the manual drive unit housing (e.g. by defining maximum forward and/or rearward extents thereof).

In embodiments, the drive transfer element defines a drive shaft having a drive head and a drive tip. In embodiments, the first retaining feature is provided to the drive shaft adjacent to the drive tip. In embodiments, the first retaining feature comprises a first ratchet feature arranged for ratchet interaction with a corresponding second ratchet feature of the manual drive unit housing. In embodiments, the first ratchet feature of the drive transfer element is pushed forwards (e.g. during assembly of the manual drive unit) and beyond the second ratchet feature of the manual drive unit housing. In embodiments, the first ratchet feature defines an arrowhead shaped feature (e.g. provided adjacent to the drive tip of the drive shaft thereof).

In embodiments, the manual drive unit housing is provided with one or more cassette unit locking features for reversibly locking the cassette unit there within at the docking position.

In embodiments, the manual drive unit housing is provided with a biasing element (e.g. a spring) arranged to bias the cassette unit away from the docking position towards a cassette-ejected position. In other embodiments, no such biasing element is present.

In embodiments, the manual drive unit housing defines a docking cavity of generally tubular form for docking receipt of a cassette unit having a cassette unit housing of generally tubular form.

In embodiments, the manual drive unit housing defines a handle arranged for ease of holding (e.g. gripping) by the fingers of a user.

In embodiments, the handle has a first flange and a second flange, thereby defining a handhold (e.g. handgrip).

In embodiments, the handle defines a first arc forming a bottom surface of the first flange contoured to correspond to a radius of an arc formed by a user's fingers and a second arc forming a bottom surface of the second flange contoured to correspond to a radius of an arc formed by the user's fingers. In embodiments, the second arc is shaped flatter than the first arc. In embodiments, the second flange is from 1.3 to 1.7 times as long as the first flange.

In embodiments, the handle of the manual drive unit housing defines a handle body, and said handle body is provided with a top cover. In embodiments, the top cover has a plurality of first mating features (e.g. pegs) adapted to mate with a set of corresponding second mating features (e.g. depressions or peg-holes) formed on the handle body.

In embodiments, the top cover includes an aperture for receiving the drive transfer element.

In embodiments, the handle body includes an aperture for receiving the drive transfer element.

In embodiments, the handle body and/or the top cover is provided with a cap lock release feature defining forwardly protruding elements arranged for pushing interaction with a cap lock feature of the cassette unit.

In embodiments, the docking cavity of the manual drive unit housing is provided with positioning features for positioning of the cassette unit received thereby. In embodiments, such positioning features comprise shaped features arranged for positioning interaction with corresponding shaped features of the cassette unit.

Cassette Unit

The cassette unit comprises a cassette unit housing defining a cassette unit housing cavity. The cassette unit housing cavity is arranged for receipt of a syringe and is therefore typically sized and shaped for this purpose. In embodiments, the cassette unit housing may be arranged as a single part or a multi-part (e.g. two part) cassette unit housing assembly.

In embodiments, the syringe is held in generally fixed fashion within the cassette unit housing. In other embodiments, the syringe is movable within the cassette unit housing such as in a direction parallel with or along the drive axis.

In embodiments, wherein the syringe is held in generally fixed fashion within the cassette unit housing, at least the needle tip of the syringe normally protrudes out of the cassette unit housing cavity such as from a needle projection aperture thereof.

The syringe that is receivable within the cassette unit housing cavity comprises a syringe barrel for holding a volume of the liquid drug formulation; a hollow needle at a front end of the barrel, the hollow needle defining a needle tip for dispensing of said liquid drug formulation; and a plunger (e.g. in the form of a rubber stopper) that is axially movable within the syringe barrel. The syringe plunger is movable axially within the barrel so as to enable the liquid drug formulation to be expelled from the barrel and thence through the hollow needle via the dispensing tip for injection into the patient. The syringe barrel is typically, comprised of glass but may also be comprised of a relatively hard plastic polymer such as hardened polyethylene, polycarbonate or cyclic olefin polymers.

In embodiments, the plunger is comprised of a natural or synthetic polymer friction material, which frictionally interacts with the side wall of the syringe barrel. Suitable plunger materials include natural or synthetic rubbers or elastomeric materials.

In more detail, the syringe barrel is selected such as to define a barrel chamber for containing a suitable volume of the liquid drug formulation. In embodiments, that suitable volume is selected to correspond to a single dose of the drug formulation to be delivered to the patient. In other words, delivery of that single dose involves expelling all of the liquid drug formulation contents of the barrel chamber through the hollow needle for injection into the patient.

In embodiments, the rear end of the syringe barrel is provided with an end flange. In embodiments, the forward end of the syringe barrel is shaped to provide a shoulder. In embodiments, forward of that shoulder the syringe narrows further into a neck, which typically forms the needle-holding part thereof.

In embodiments, the needle barrel is provided with a barrel sleeve that is arranged to fit over part or all of the length of the needle barrel. The barrel sleeve may also extend out beyond the syringe barrel to wholly or partly enclose a length of the forward shoulder of the syringe barrel and of the hollow needle that extends from (the forward shoulder) of the syringe barrel.

In embodiments, the cassette unit is arranged to accommodate multiple syringe sizes. Common sizes of syringe include the 2.25 ml syringe and the 1 ml 'long' syringe, which has a smaller syringe barrel diameter.

In embodiments, accommodation of multiple syringe sizes within the same cassette unit geometry is achievable by providing suitable adapters to the barrel of the syringe. In embodiments, sleeve form adapters are employed.

In embodiments, the sleeve form adapter is arranged for receipt by the syringe barrel and fits at least partly over the flange of the rear end of the syringe barrel. In embodiments, the sleeve adapter is arranged for snap fitting over the end flange of the syringe. In embodiments, the flange is effectively capped by the relevant 'end flange' part of the sleeve form adapter.

In embodiments, a major portion of the syringe barrel and end flange thereof is in use, sleeved by the sleeve form adapter. The overall effect of this sleeving of a major portion is firstly to increase the effective diameter of the syringe barrel; secondly to provide strengthening reinforcement to the end flange; and thirdly to increase the effective length of the syringe.

In one particular embodiment, the cassette unit is shaped and sized based on the geometry of the larger 2.25 ml syringe. A syringe having a smaller outer dimension (e.g. a 1 ml 'long' syringe) may then be accommodated in this same cassette unit by use of a sleeve adapter that effectively functions to adapt the outer syringe geometry (e.g. the outer diameter thereof) to closely correspond to or to be identical with that of the 2.25 ml syringe.

In embodiments, adding a sleeve adapter to the smaller diameter 1 ml 'long' syringe can make it slightly longer than the 2.25 ml syringe. In embodiments, when the cassette unit is assembled with the 2.25 ml syringe, an adapter ring may be added underneath the syringe flange to make its effective flange thickness the same as that of a smaller 1 ml syringe with a sleeve adapter.

In embodiments, the sleeve adapter is provided with one or more slits in the wall(s) of the sleeve adapter such as to define flexible fingers, which allow the adapter to flex open. In embodiments, the presence of such flexible fingers is of utility during assembly of the sleeved syringe as the needle cover (e.g. rigid needle shield), which typically has a larger diameter than the syringe barrel, passes through the centre of it when the syringe is pressed into the adapter. In embodiments, the end flange at the rear end of the syringe then snaps into the rear end of the adapter such that the syringe is locked into the adapter once assembled.

In embodiments, one or more positioning and/or retaining features are provided to the cassette unit housing for positioning and/or retaining the syringe and sleeve form adapter in the cassette unit housing cavity. In embodiments, the one or more positioning and/or retaining features comprise one or more snap features provided interiorly to the cassette unit housing.

In certain implementations, the ability of the cassette unit to accommodate syringes of different sizes confers certain advantages. In the case of manual drive units with a variable performance across the injection stroke it may be advantageous in some circumstances to use a syringe of larger bore diameter because the same volume of drug can be delivered from a shorter injection stroke, thereby enabling the manual drive unit performance to be optimized.

Similarly, for a given combination of needle and drug (same needle bore and viscosity) the volume injected per unit displacement of the plunger is greater in the case of a wider bore syringe by a factor proportional to the square of the difference in syringe diameter. A faster injection can therefore be achieved for the same plunger displacement velocity. In this case the force applied by the plunger will be greater in the larger syringe due to the increase in volumetric flow rate. This may be useful in cases where the maximum displacement velocity is limiting.

It has been appreciated that to reduce the risk of the syringe shattering under the loads associated with injecting the drug, it is important for a majority of the load path to travel through the shoulder at the forward end of the syringe and lesser load to pass through the flange at the rear end of the syringe.

In embodiments, the forward shoulder of the syringe is provided with one or more shoulder support features. In embodiments, the one or more shoulder support features are integral (e.g. integrally formed) with the cassette unit housing. In other embodiments, the one or more shoulder support features are defined by one or more separate shoulder support parts provided to the cassette unit.

In embodiments, the one or more shoulder support features locate (e.g. in snap-fit arrangement) between the needle cover (e.g. rigid needle shield) and the forward shoulder of the syringe. In embodiments, the sleeve adapter as described above, is provided with such one or more shoulder support features that in embodiments, snap-fit between the needle cover (e.g. rigid needle shield) and the forward shoulder of the syringe. This snap fitting is typically enabled after the syringe assembly has been pressed through the sleeve adapter during the assembly operation.

In embodiments, a clearance space is defined between the bottom of the syringe flange and the closest surface of the sleeve adapter. In embodiments, the sleeve form adapter acts to space the end flange of the syringe from the inner walls of the cassette unit housing. In embodiments, when the syringe is loaded within the cassette unit housing the flange of the syringe is spaced from the inner walls of the cassette unit housing and/or the sleeve adapter and in embodiments, is not in contact with anything.

In embodiments, at least part of the syringe or syringe/sleeve adapter combination interacts with (e.g. inserts into) a constraining feature of the cassette unit housing that has a tight clearance between its inner walls and the outside diameter of the standard (e.g. 2.25 ml) syringe. In embodiments, this constraining feature of the cassette unit housing interacts with the shoulder and/or neck of the syringe. In embodiments, this feature is the only surface acting to constrain the position of the syringe within the cassette unit housing (e.g. during injection). In embodiments, the constraining feature of the cassette unit housing that constrains the syringe also prevents the sleeve adapter from flexing outwards when the injection loads are applied to the syringe. With the rear end of the sleeve adapter (e.g. any defined fingers thereof) securely snapped under the shoulder of the syringe and so prevented from flexing outwards, the syringe is effectively secured within the cassette unit housing. In embodiments, if this were not the case the force applied to the syringe during injection could push the fingers open and enable the syringe to push through.

The hollow needle defines a needle bore, which is most typically of circular cross-section and of selected bore diameter. It may be appreciated that in embodiments, the bore diameter may affect the force required to expel the liquid drug formulation through the needle and also the velocity at which the liquid drug formulation is expelled.

The selected needle bore may also, in embodiments affect the degree of patient discomfort during injection. Smaller bore diameters, typically provide more patient comfort, whereas larger bore diameters enable more rapid/lower force delivery of the liquid through the needle. A compromise is therefore needed in selecting a needle bore to provide acceptable patient comfort and liquid delivery through the needle characteristics.

Examples of typical needles that are suitable for use therein include 12.5 mm ("half inch") long thin wall needles of grade 23G, 25G or 27G. These have a needle bore of from about 0.2 to 0.4 mm such as from 0.25 to 0.35 mm. Other examples include both regular and thin wall needles used in conventional syringes including those with bevels such as 3 and 5 bevels.

The cassette unit housing and any inner cassette unit housing sub assembly thereof is shaped to define a cassette unit housing cavity within which the syringe is receivable, and in embodiments, a needle projection aperture. The cassette unit housing cavity is typically cylindrical in form, thereby matching the typically cylindrical outer profile of a syringe. The cassette unit housing cavity may be further shaped with any manner of grooves, indentations or other shaping or surface details to define a 'lock and key' relationship between the cassette unit housing and any inner cassette unit housing sub assembly thereof and the syringe. Colour guides, arrows and any other surface markings may also be employed.

Typically, the cassette unit housing and/or any inner cassette unit housing sub assembly thereof is provided with a barrel receiving part for receiving the barrel of the syringe; a plunger receiving part for receiving the plunger of the syringe; and in embodiments, a needle receiving part for receiving the hollow needle of the syringe.

In embodiments, the plunger receiving part of the cassette unit housing and/or any inner cassette unit housing sub assembly thereof allows the plunger within the syringe barrel to be received thereby and for the plunger to be movable (e.g. axially) therein from a first position to a second position, in which it is moved somewhat into the syringe barrel. During use the plunger is in embodiments, movable to a fully plunged position in which most, in embodiments all of the liquid drug formulation contents of the barrel have been expelled.

In embodiments, the needle receiving part of the cassette unit housing and/or any inner cassette unit housing sub assembly thereof includes a needle projection aperture through which the hollow needle may protrude from the housing, for example during expelling of the liquid drug formulation through the hollow needle and its needle tip for delivery to the patient.

In embodiments, the cassette unit housing is provided with a removable cap that fits over and thereby, acts such as to close off, the needle projection aperture. It may therefore, be appreciated that when in the capped position, the removable cap acts such as to prevent ingress of contaminants into the needle receiving part of the housing.

In embodiments, the syringe further comprises a needle cover defining a needle sheath arranged in a sheathing configuration for sheathing (e.g. sealing) of the needle tip.

In embodiments, the needle sheath is comprised of a (e.g. resiliently) compressible material such as a natural or synthetic rubber material. In a storage configuration, the needle tip sticks into (e.g. is spiked or staked into) the needle sheath such that sealing of the needle tip is achieved. Usually, at least the first 3 to 4 mm of the needle tip end is so sheathed. It will be appreciated that for clinical reasons, the sealing of the needle tip acts in embodiments, such as to prevent passage of contaminant, bacterial or otherwise, through the needle tip and thus into the needle bore and syringe barrel chamber. Sterile sealing is preferred.

In embodiments, the needle cover is provided with a needle sheath cover for covering the needle sheath thereof. In embodiments, the needle sheath cover is comprised of a rigid material (e.g. polypropylene). In embodiments, the needle sheath cover is provided with one or more gripping elements (e.g. hooks) arranged for gripping of the needle sheath. In embodiments, the needle sheath is provided with one or more features arranged for receipt of the one or more gripping elements such as one or more indents, grooves or cavities.

In embodiments, the needle cover is provided to (e.g. fixed to or integral with) a removable cap for the cassette unit housing. Thus, in embodiments, the needle cover projects within the cap such that when the removable cap is in the capped position the needle sheath and any needle sheath cover therefor projects towards the needle tip of the syringe. In such embodiments, when in the capped position, the needle tip is sheathed by the needle sheath, and when the cap is removed the needle sheath and any needle sheath cover therefor are also removed such as to thereby, unsheathe the needle tip. In embodiments, the removable cap defines an essentially closed cylindrical cap chamber, optionally tapering, and the needle sheath and any needle sheath cover are provided along the axis of that cylindrical chamber.

In embodiments, the interior of the removable cap is provided with a connector defining one or more needle cover gripping elements for gripping the needle cover (i.e. gripping the needle sheath and/or any needle sheath cover therefor). In embodiments, such gripping elements are arranged for gripping of the needle cover when in the capping position. In embodiments such gripping elements are (e.g. additionally) arranged for gripping of the needle cover on removal of the cap such that removal of the cap also results in removal of the needle cover and hence, unsheathing of the needle tip. In embodiments, the needle cover gripping elements are arranged to project away from the top inner surface (e.g. of the cylindrical cap chamber) of the removable cap and towards its open end.

In embodiments, the connector comprises one or more needle cover gripping elements (e.g. gripping legs) attaching to a central hub. In embodiments, the connector is in the form of a cage-like needle cover gripper. In embodiments, each gripping element (e.g. leg) is provided (e.g. at the foot thereof) with one or more gripping protrusions such as one or more internally facing hooks or barbs. In embodiments, the internally facing hooks or barbs are disposed at an angle with respect to the gripping leg. In embodiments, the connector locates within the removable cap such that the central hub locates adjacent to or slightly spaced from the top inner cap wall or surface and the gripping legs project away from the top inner cap wall or surface and towards the open end of the cap. Other needle cover gripper arrangements are disclosed in Applicant's PCT publication no. WO2009/081103 the entire contents of which are incorporated herein by reference.

In embodiments, the removable cap is provided with a connector. The connector is shaped to fit within and engage the needle cover and to engage the inner part of the removable cap. In embodiments, the connector includes one or more needle gripper elements in the form of first legs attaching to a central hub and spaced symmetrically away from one another, each first leg having one or more internally facing barbs pointing toward a forward region of the connector and adapted to engage a proximal region of the needle cover. In embodiments, the one or more internally facing barbs are disposed at an angle with respect to the first leg. In embodiments, the connector also includes one or more second legs spaced symmetrically away from one another, each second leg having one or more externally facing barbs located in the forward region of the connector and adapted to engage a forward region of the inner part of the removable cap. In embodiments, the one or more first legs are biased initially at about 60 to 80 degrees with respect to the horizontal. Arrangements of removable cap and connector of this type are disclosed in Applicant's PCT publication no. WO2009/090499 the entire contents of which are incorporated herein by reference.

In embodiments, the geometry of the removable cap is selected to allow for the needle cover to be sufficiently aligned with the needle of the syringe so that on re-capping the needle does not undesirably catch on the needle sheath inside the needle cover. In embodiments, wherein the connector comprises one or more needle cover gripping elements (e.g. gripping legs) attaching to a central hub, Applicant has found that to assist re-sheathing of the needle cover it is desirable to position the connector within the removable cap such that the central hub is in spaced relationship to the top inner cap wall of the removable cap. When so-positioned, the gripping legs project away from the top inner cap wall and towards the open end of the cap. Applicant has found that having the central hub in somewhat spaced relationship to the top inner cap wall allows for a certain 'give' in the axial position of the needle cover such that in the event of any snagging of needle cover by the needle tip during re-sheathing, the connector and/or needle cover is free to move into the 'give' space, thereby ensuring that the snagging event does not result in any bending, or in a worst case scenario snapping, of the needle. The occurrence of any needle stick hazards during re-capping and re-sheathing is thus, minimized. In addition, the presence of 'give' space ensures that it is always possible to refit the cap, which may otherwise be prevented by needle snagging.

In embodiments, the removable cap is provided with a spacer insert and the connector is provided to (e.g. locates within) the spacer insert. In these embodiments, the function of the spacer insert is effectively to assist in defining of the 'give' space as described above. In embodiments, the spacer insert defines a central end hub and an inner boss, which extends from the central end hub to define a chamber for receiving the connector and in embodiments also, in use for receiving the needle cover as gripped by the connector. In embodiments, the spacer insert also defines an outer boss, which extends from the end hub and in embodiments, also extends about (e.g. circumferentially about) the inner boss. In embodiments, the outer boss includes crenellated portions therein. In embodiments, the outer boss defines flexible fingers, which splay out from the central end hub and thus, extend about the outer surface (e.g. of the lower part of) the outer boss. In embodiments, the flexible fingers of the outer boss locate within the crenellated portions of the outer boss. In embodiments, the spacer insert is comprised of a plastic (e.g. a plastic polymer) material and thus, may be referred to as a plastic 'outer flower' structure. In embodiments, the chamber of inner boss of the spacer insert is provided with a connector (e.g. a needle cover gripper such as in the form of a cage-like structure) and defining plural gripping elements arranged about a central hub. In embodiments, the connector is comprised of a metal and may thus, be referred to as a metal 'inner flower' structure.

To assist with re-sheathing of the needle cover on re-capping of the cassette unit after an injection procedure, the position of spacer insert and connector held there-within is in embodiments, arranged within the removable cap such that central end hub of the spacer insert is in spaced relationship to the effective end wall of the removable cap. By effective end wall it is meant either the actual end wall of the removable cap or a structure (e.g. ledge-like structure) that functions as a seat for the central end hub of the spacer insert and thus, defines the minimum spaced relationship between that central end hub and the end of the removable cap. Having the central end hub of the spacer insert in somewhat spaced relationship to the effective end wall of the removable cap allows for a certain 'give' in the axial position of the connector and needle cover gripped thereby such that in the event of any snagging of needle cover by the needle tip during re-sheathing, the spacer insert, connector and needle cover are free to move into the 'give' space, thereby ensuring that the snagging event does not result in any bending, or in a worst case scenario snapping, of the needle. The occurrence of any needle stick hazards during re-capping and re-sheathing is thus, minimized.

In embodiments, the removable cap is provided with a finger-grip feature that is sized and shaped for gripping by the finger of a user and to provide a ready means for removing the cap and needle cover attached thereto. In embodiments, the finger-grip feature is shaped to provide a ring (e.g. a gripping ring or ring pull) for ready finger gripping by the user by placing a finger or thumb inside the ring.

In embodiments, the removable cap, in a capping position, fits over and thereby, acts such as to close off, the needle projection aperture of the cassette unit housing.

In embodiments, the cassette unit housing is provided with a cap lock feature that is movable from a first cap locking position in which it prevents removal of the cap from the cassette unit to a second cap un-locking position in which it no longer prevents such cap removal.

In embodiments, the cassette unit housing is provided with one or more first engagement features arranged for reversibly engaging one or more second engagement features of the removable cap for reversible lock engagement of the removable cap to the cassette unit housing.

In embodiments, the first engagement features of the removable cap and the second engagement features of the cassette unit housing are arranged to have a mutually engaging form selected from the group consisting of latching, peg and socket and snap-fit.

In embodiments, the cassette unit housing is provided at the forward end thereof with one or more axially protruding legs each having a first engagement feature arranged thereon, the one or more legs arranged to extend up into the removable cap when the cap is in the capping position and the one or more second engagement features are defined as sockets of the removable cap.

In embodiments, the one or more legs are arranged in a circumferential arrangement about the forward end of the cassette unit housing and said sockets of the removable cap adopt a corresponding circumferential arrangement.

In embodiments, each of the one or more first engagement features of the one or more legs is in the form of a protruding heel having a shaped tip.

In embodiments, the geometry of the removable cap is selected to allow for the needle cover to be sufficiently aligned with the needle of the syringe so that on re-capping the needle does not undesirably catch on the needle sheath inside the needle cover. In embodiments, the geometry of the first engagement features of the cassette unit housing and/or second engagement features of the removable cap is selected to allow for such ease of re-capping. In embodiments, once the first engagement features of the cassette unit housing begin to engage with the second engagement features of the removable cap it is held concentrically enough to prevent the needle from catching on the needle sheath. This is important to ensure that on re-capping the needle cover is able to fully sheathe the used needle to minimize the occurrence of any needle stick hazards.

In embodiments, the cassette unit is provided with a cap lock (i.e. cap removal prevention) feature for selectively preventing removal of the removable cap. In embodiments, the cap lock feature is movable from a first cap locking position in which it prevents removal of the cap from the cassette unit to a second cap un-locking position in which it no longer prevents such cap removal.

In embodiments, the cassette unit is provided with a shuttle lock control defining one or more blocking elements for selectively blocking movement of said one or more first engagement features of the cassette unit housing relative to the one or more second engagement features of the removable cap.

In embodiments, the shuttle lock control is axially movable relative to the cassette unit housing between:

(i) a first 'cassette unused' position, in which said one or more blocking elements block movement of the one or more first engagement features relative to the one or more second engagement features, thereby keeping the removable cap in locked relationship to the cassette unit housing;

(ii) a second 'cassette unlocked' position, in which said one or more blocking elements no longer block movement of the one or more first engagement features relative to the one or more second engagement features, thereby allowing for unlocking of the removable cap from the cassette unit housing and for removal and replacement thereof; and (iii) after replacement of the removable cap, a third 'cassette used' position, locating intermediate said first and second positions, in which the one or more blocking elements again block movement of the one or more first engagement features relative to the one or more second engagement features, thereby restoring the locked relationship between the removable cap and the cassette unit housing.

In embodiments, the shuttle lock is biased from the second position to the third position.

In embodiments, in use, on removal of the removable cap the shuttle lock control is in the second position; during use of the cassette for injection the shuttle lock control is biased into the third position; and during replacement of the removable cap the shuttle lock control is in the second position.

In embodiments, the shuttle lock control is further provided with an axial position locator, which defines three distinct axial positions of the shuttle lock control relative to cassette unit housing and corresponding to the first, second and third positions.

In embodiments, the axial position locator comprises one or more axial protrusions each having a follower arranged thereon for receipt within a corresponding axial track of the inner cassette unit housing such as to define an axial track-follower relationship therebetween.

In embodiments, the first and second positions correspond to the opposite extremes of the axial track-follower relationship.

In embodiments, each of the one or more axial protrusions of the axial position locator comprises a first latch element arranged for selective latching relationship with a corresponding second latch element of the inner cassette unit housing.

In embodiments, the first latch element defines an axial latching slot and the second latch element comprises a latching foot selectively receivable thereby and movable therewithin such as to define an axial foot-in-slot relationship therebetween.

In embodiments, in the first position the axial latching slot and latching foot are in non-latching relationship and in the second and third positions the axial latching slot and latching foot are in latching relationship, wherein the second and third positions respectively correspond to opposing slot ends of the axial latching slot.

In embodiments, the cassette unit (e.g. at the shuttle lock control) additionally comprises a non-return feature arranged such that when the first and second latch elements have come into latching relationship return to a non-latching relationship is prevented.

In embodiments, as part of the non-return feature the first latch element defines a forward ramped surface and the second latch element defines a corresponding ramped surface such as to facilitate ramping over each other when coming into latching relationship.

In embodiments, the shuttle lock control is marked with a 'used cassette' flag arranged to be brought into registration with an indicator opening or window of the cassette unit housing at the third 'cassette used' position.

In embodiments, the cap lock (i.e. cap removal prevention) feature selectively prevents removal of the removable cap until either the cassette unit locates at the docking position within the manual drive unit housing or until a release mechanism is activated. In embodiments, the cap lock feature of the cassette unit is only movable from a cap locking position to a cap non-locking position when the cassette unit locates at the docking position within the manual drive unit housing. In embodiments, the cap lock feature is in the first position during insertion of the cassette unit into the manual drive unit and moves to the second position when the cassette unit is in the docking position in the manual drive unit.

In embodiments, the manual drive unit includes a cap lock release feature arranged such that on moving of the cassette unit towards the docking position in the manual drive unit said cap lock release feature interacts with the cap lock feature of the cassette unit to move the cap lock feature to the second cap unlocking position when the cassette unit is at the docking position in the manual drive unit.

In embodiments, the cassette unit includes a plunger slaving part, which is axially movable within the barrel of the syringe for forward movement into contact with the plunger. In embodiments, the plunger slaving part defines a circumferential wall arranged for frictional sliding relationship with the inner wall of the barrel, a rear drive-receiving face and a front plunger-contacting face.

In injected use, the plunger slaving part is in embodiments, brought into contact with the plunger of the syringe and is axially movable within the barrel. In embodiments, the plunger slaving part arranged such that when a drive load is applied to the rear drive-receiving face to bring the front plunger-contacting face into contact with the plunger the drive load is evenly transmitted to the plunger.

In embodiments, the front plunger-contacting face of plunger slaving part is arranged for engagement with the plunger. In embodiments, the diameter of the plunger slaving part corresponds to the diameter of the plunger.

In embodiments, the plunger is made of a material that is resiliently compressible (e.g. rubber or an organic polymeric material) and the plunger slaving part is made of a less compressible material. In embodiments, the plunger slaving part is made of a rigid material (e.g. a hard plastic polymer material such as poly propylene).

In embodiments, the rear drive-receiving face of the plunger slaving part has a central recess for receipt of a drive transfer element. In embodiments, the central recess is shaped such that the drive transfer element is rotatable therein. In embodiments, the central recess is of conical form. In embodiments, the central recess tapers to a square-cut end or to a neb end.

In embodiments, the slaving part may be configured to perform a second purpose of providing an easy-to-identify visual indicator of the plunger's position within the syringe so that the patient can visually confirm the drug had been fully injected. In this embodiment, the slaving part may also be called a stopper position indicator.

In embodiments, the circumferential wall of the plunger slaving part is provided with one or more slide restrictors that restrict frictional sliding movement thereof in relation to the inner wall of the barrel. In embodiments, the one or more slide restrictors are arranged to increase the resistance thereof to frictional sliding movement.

In embodiments, each of the one or more slide restrictors comprises a flexible vane arranged to flex slightly in response to frictional sliding movement of the plunger slaving part.

In embodiments, the one or more slide restrictors are arranged to increase the initial resistance to forward frictional sliding movement but to impart lesser resistance to said forward frictional sliding movement once movement is underway.

In embodiments, the one or more slide restrictors are arranged to more greatly increase the resistance to a backward frictional sliding movement than to the forward frictional sliding movement.

In embodiments, the one or more slide restrictors are arranged at evenly spaced intervals around the circumferential wall.

In embodiments, the cassette unit housing defines a rearward entrance to the cassette unit housing cavity, additionally comprising in capping relationship with a rearward entrance of the cassette unit housing, a cassette unit end-cap. In embodiments, the cassette unit end-cap defines a drive transfer element-receiving opening for receipt of a drive rod for providing forward axial drive to said plunger slaving part.

In embodiments, in a pre-use configuration, the plunger slaving part is shaped for releasable engagement with the cassette unit end-cap.

In embodiments, the drive transfer element-receiving opening is defined by a periphery and the plunger slaving part is shaped for releasable engagement in the pre-use configuration with the periphery.

In embodiments, the drive transfer element-receiving opening is defined by a peripheral rim and said plunger slaving part is shaped for releasable engagement in the pre-use configuration with the peripheral rim.

In embodiments, the drive transfer element-receiving opening is defined by a periphery, the periphery is provided with a forward skirt and the plunger slaving part is shaped for releasable engagement in the pre-use configuration with the forward skirt.

In embodiments, the forward skirt is provided with an inner-facing rim and the plunger slaving part is shaped for releasable engagement in the pre-use configuration with the inner-facing rim.

In embodiments, the plunger slaving part defines a circumferential rim for releasable engagement in the pre-use configuration with the cassette unit end-cap.

In embodiments, the plunger slaving part defines a circumferential trough for releasable engagement in the pre-use configuration with the cassette unit end-cap.

In embodiments, the plunger slaving part is releasable from the cassette unit end-cap in response to forward axial drive provided to the rear drive-receiving face thereof.

In embodiments, the end-cap is arranged for snap-fit relationship with the cassette unit housing.

In embodiments, the cassette unit additionally comprises a biasing element (e.g. a spring) defining a biasing relationship (a sprung biasing relationship) between the cassette unit end-cap and the flange of the syringe, thereby urging the syringe forwards in relation to the cassette unit end cap.

In embodiments, the drive transfer element-receiving opening of the cassette unit end cap is defined by a periphery, the periphery is provided with a forward skirt and said biasing element (e.g. a spring) is arranged for receipt about the forward skirt.

In embodiments, the biasing element (e.g. a spring) is provided as a separate component to the cassette unit end-cap. In other embodiments, the biasing element (e.g. a spring) is provided integrally with the cassette unit end-cap.

In embodiments, the cassette unit additionally comprises one or more shoulder support features for supporting the forward shoulder of the syringe.

In embodiments, the cassette unit further comprises a needle cover defining a needle sheath for sheathing of the needle tip, wherein the one or more shoulder support features locate between the needle cover and the forward shoulder of the syringe.

In embodiments, the needle cover is provided with a needle sheath cover for covering the needle sheath thereof and the one or more shoulder support features locate between the needle sheath cover and the forward shoulder of the syringe.

In embodiments, the needle sheath cover is comprised of a rigid material.

In embodiments, the one or more shoulder support features are in snap-fit arrangement between the needle cover and the forward shoulder of the syringe.

In embodiments, the one or more shoulder support features are defined by one or more separate shoulder support parts provided to the syringe.

In embodiments, the one or more shoulder support features include a split-cylindrical form arranged for receipt by the barrel of the syringe.

Interaction of Cassette Unit with Manual Drive Unit

In embodiments, the manual drive unit housing and/or any inner manual drive unit housing sub assembly thereof includes a needle projection aperture through which the hollow needle of the syringe of the cassette unit may protrude, for example during expelling of the liquid drug formulation through the hollow needle and its needle tip for delivery to the patient.

In embodiments, the manual drive unit housing is provided with one or more cassette unit locking features for reversibly locking the cassette unit within the housing and hence, within the manual drive unit. In embodiments, the manual drive unit housing is provided with a push arm arranged for pushing interaction with said locking features, thereby allow for unlocking thereof. In embodiments, the push arm is a flexible push arm. In embodiments, the push arm pivotally connects to the manual drive unit housing.

In embodiments, the one or more cassette unit locking features are arranged to be in a locking position when the cassette unit is in the docking position.

In embodiments, in the locking position the one or more locking features of the cassette unit housing align with corresponding features (e.g. apertures) of the manual drive unit housing.

In embodiments, movement of the cassette unit from an intermediate pre-docking position to the docking position results in movement of the one or more locking features from the non-locking to the locking position.

In embodiments, each cassette unit locking feature comprises a latching feature, lock tab feature or snap-lock feature. In embodiments, engagement of the locking feature provides tactile or audible feedback to the user as an indication that the cassette unit has been correctly received within the manual drive unit housing of the manual drive unit.

In embodiments, the manual drive unit housing is provided with one or more cassette unit locking features protruding from the inner wall(s) thereof. In embodiments, the cassette unit locking features are biased towards (e.g. in response to biasing means) or naturally bias towards the cassette locking position.

In embodiments, the manual drive unit housing has plural (e.g. two) cassette unit locking features (e.g. snap lock-tabs) integral with and protruding inwards from the walls thereof.

In embodiments, each of the cassette unit locking features has one or more angled faces arranged such that the locking feature may be pushed outwards as a result of force applied to the angled face.

In embodiments, each cassette unit locking feature (e.g. lock tab) has angled faces at the top and bottom thereof arranged such that the locking feature (e.g. lock tab) flexes outwards when a force (e.g. from an edge of another mechanical part) is pushed into them from either direction. In embodiments, the angled face at the bottom side of the locking feature allow for it to flex out of the way as the cassette unit is inserted into the manual drive unit housing until the cassette unit is inserted to a holding and locking position, wherein the locking feature flexes back to its original position and lockingly engages the cassette unit housing. In this position the cassette unit is held in the manual drive unit housing by the locking features (e.g. lock-tabs) because the top faces of the locking features (e.g. lock-tabs) support the cassette unit. The angled faces on the top of the locking features (e.g. lock-tabs) also allow for the cassette unit to be pulled out of the manual drive unit housing by having the lock-tabs flex outwards in a similar fashion as when a cassette unit is inserted into the manual drive unit housing of the manual drive unit of the injector.

In embodiments, as the cassette is moved to the docking position within the manual drive unit, the one or more locking features of the cassette unit holder are aligned with rigid features within the manual drive unit that maintain the locking features in the locking position such as by preventing lock-tabs from flexing outwards. Thus, the cassette unit is effectively locked within the manual drive unit when the locking features are aligned with these rigid features of the manual drive unit.

In embodiments, once the cassette unit has been received at the docking position the removable cap and needle cover attached thereto is removed. Where in embodiments, there is a cap lock feature this must first be released. In embodiments, as the cassette is moved to the docking position (e.g. by being inserted fully into the manual drive unit) the cassette unit is also brought into contact with cap lock release features, which in embodiments comprise one or more (e.g. two) forwardly protruding elements (e.g. rigid arms), which extend into the cassette unit to depress, and thereby to unlock, the cap lock feature. In embodiments, the cap lock release features are rigidly fixed within the manual drive unit, and the protruding elements (e.g. rigid arms) thereof that move into the cassette unit to depress, and thereby to unlock, the cap lock feature pass through cut-outs in the top of the cassette unit holder.

In embodiments, the manual drive unit housing is provided with one or more cassette unit securing arms arranged to prevent removal of an uncapped cassette unit therefrom. In embodiments, the one or more cassette unit securing arms have securing (e.g. blocking) tips arranged for securing (e.g. blocking) interaction with (e.g. a forward end of) the cassette unit housing. In embodiments, in a 'cassette unit securing' position, the one or more cassette unit securing arms protrude upwardly and inwardly into the manual drive unit housing. In embodiments, the one or more cassette unit securing arms are biased (e.g. sprung) towards that 'cassette unit securing' position. In embodiments, the one or more cassette unit securing arms interact with the removable cap of the cassette unit such that when the cap is in place (i.e. a cassette capped position), the one or more cassette unit securing arms are displaced to a 'cassette unit non-securing' position, and when the cap is not in place (i.e. a cassette uncapped position), the one or more cassette unit securing arms are in the 'cassette unit securing' position.

In embodiments, the drive transfer element could direct undesirably high drive loads on the system if the drive transfer element makes direct contact with the syringe plunger. To minimize these loads, the syringe barrel of the cassette unit may be provided with a plunger slaving part. Thus, the drive transfer element acts to transfer axial drive to the plunger slaving part and hence, to the plunger of the syringe for moving the plunger into the barrel of the syringe to eject at least part of said volume of liquid drug formulation.

In embodiments, the plunger slaving part is in contact with the plunger of the syringe and is axially movable within the barrel. In embodiments, the plunger slaving part is arranged such that when a drive load is applied to a rear (e.g. top) drive-receiving face thereof the drive load is evenly transmitted to the plunger. In embodiments, the plunger slaving part engages (e.g. is in threaded engagement) with the plunger. In embodiments, the diameter of the plunger slaving part corresponds to the diameter of the plunger.

In embodiments, the plunger is made of a material that is resiliently compressible (e.g. rubber or an organic polymeric material) and the plunger slaving part is made of a less compressible material. In embodiments, the plunger slaving part is made of a rigid material (e.g. a hard plastic polymer material such as poly propylene).

In embodiments, the rear face of the plunger slaving part has a central recess for receipt of a drive transfer element. In embodiments, the central recess is of conical form. Thus in embodiments, the drive transfer element defines a drive end arranged for receipt by the central recess of the rear drive-receiving face of the plunger slaving part. In embodiments, the drive end defines a conical tip and said central recess is of conical form to guide and centre said conical tip therein. In embodiments, the angle of the conical recess is greater than the angle of the conical tip.

In embodiments, the slaving part may be configured to perform a second purpose of providing an easy-to-identify visual indicator of the plunger's position within the syringe so that the patient can visually confirm the drug had been fully injected. In this embodiment, the slaving part may be called a stopper position indicator.

Kit of Parts

In embodiments, there is also provided a kit of parts comprising a cassette unit (absent syringe) as described above; and a syringe containing a liquid drug formulation.

In embodiments, there is further provided a kit of parts comprising a cassette unit (which may in embodiments, be in kit of parts form) as described above; and a manual drive unit as described above.

In embodiments, there is further provided a kit of parts comprising an injector (which may in embodiments, be in kit of parts form) as described above; and packaging therefor. Suitable packaging typically comprises a storage container for the manual drive unit and one or more cassette units.

BRIEF DESCRIPTION OF THE DRAWINGS

The disclosure is further described with reference to the accompanying drawings, in which:

FIG. 5b is a perspective view of the syringe with shoulder support assembly of FIG. 5a;

FIG. 5b is a sectional view of the syringe with shoulder support assembly of FIGS. 5a and 5b;

FIGS. 19a to 19c are perspective, side cross-sectional and front cross-sectional views of the drive rod of the manual drive unit of FIG. 16;

DETAILED DESCRIPTION

To provide an overall understanding of the systems, devices and methods described herein, certain illustrative embodiments will now be described. For the purpose of clarity and illustration these systems and methods will be described with respect to injectors that employ manual drive units and cassette units that receive medicament syringes. It will be understood by one of ordinary skill in the art that the systems, devices and methods described herein may be adapted and modified as is appropriate, and that these systems, devices and methods may be employed in other suitable applications, such as for other types of manual drive units and cassette units, and that other such additions and modifications will not depart from the scope hereof.

Figure 1:
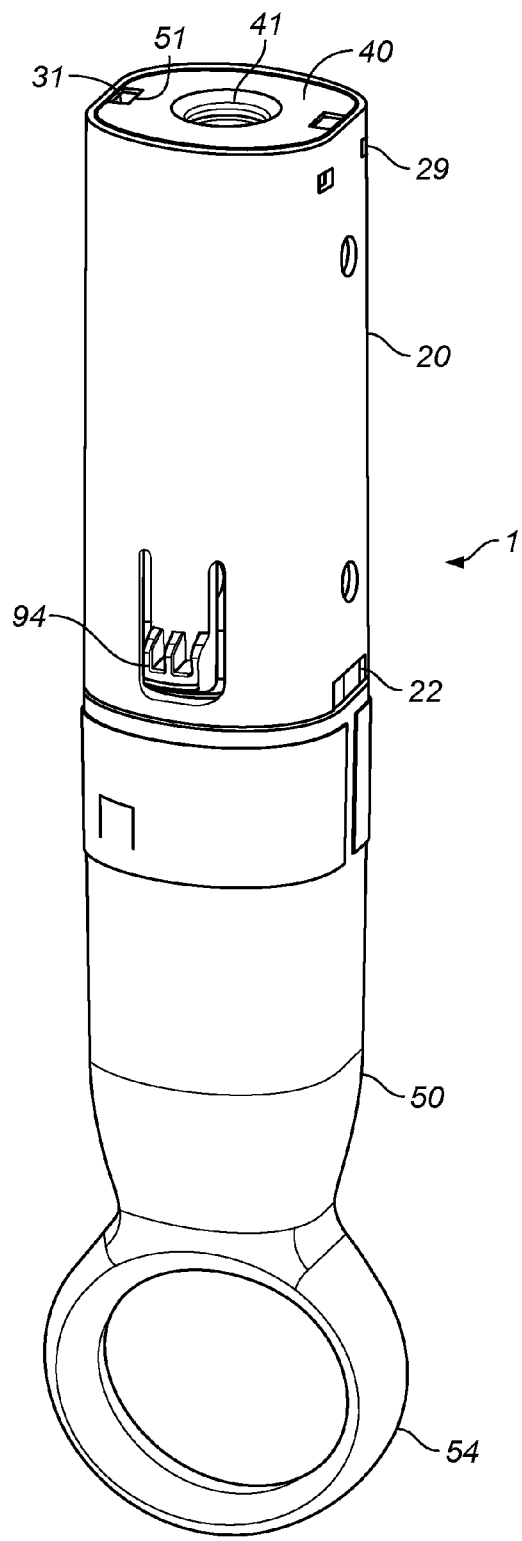
FIG. 1 is a perspective view of a cassette unit of an injector herein and shown in the 'pre-use' configuration.
Figure 2:
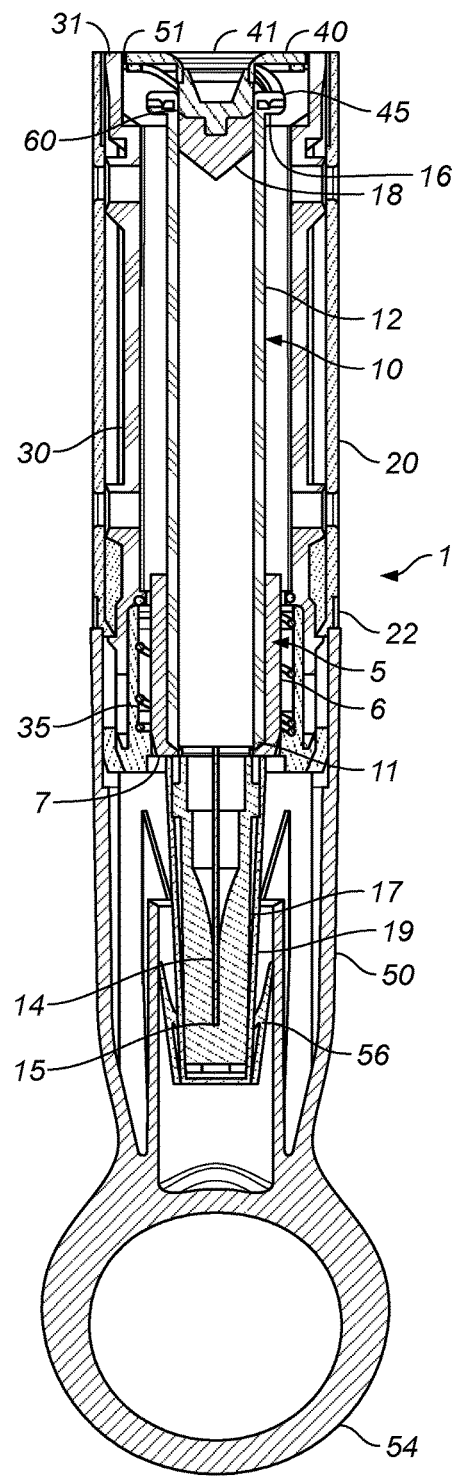
FIG. 2 is a sectional view of the cassette unit of FIG. 1 arranged for use with a 1 ml syringe also in the 'pre-use' configuration.
Figure 3:
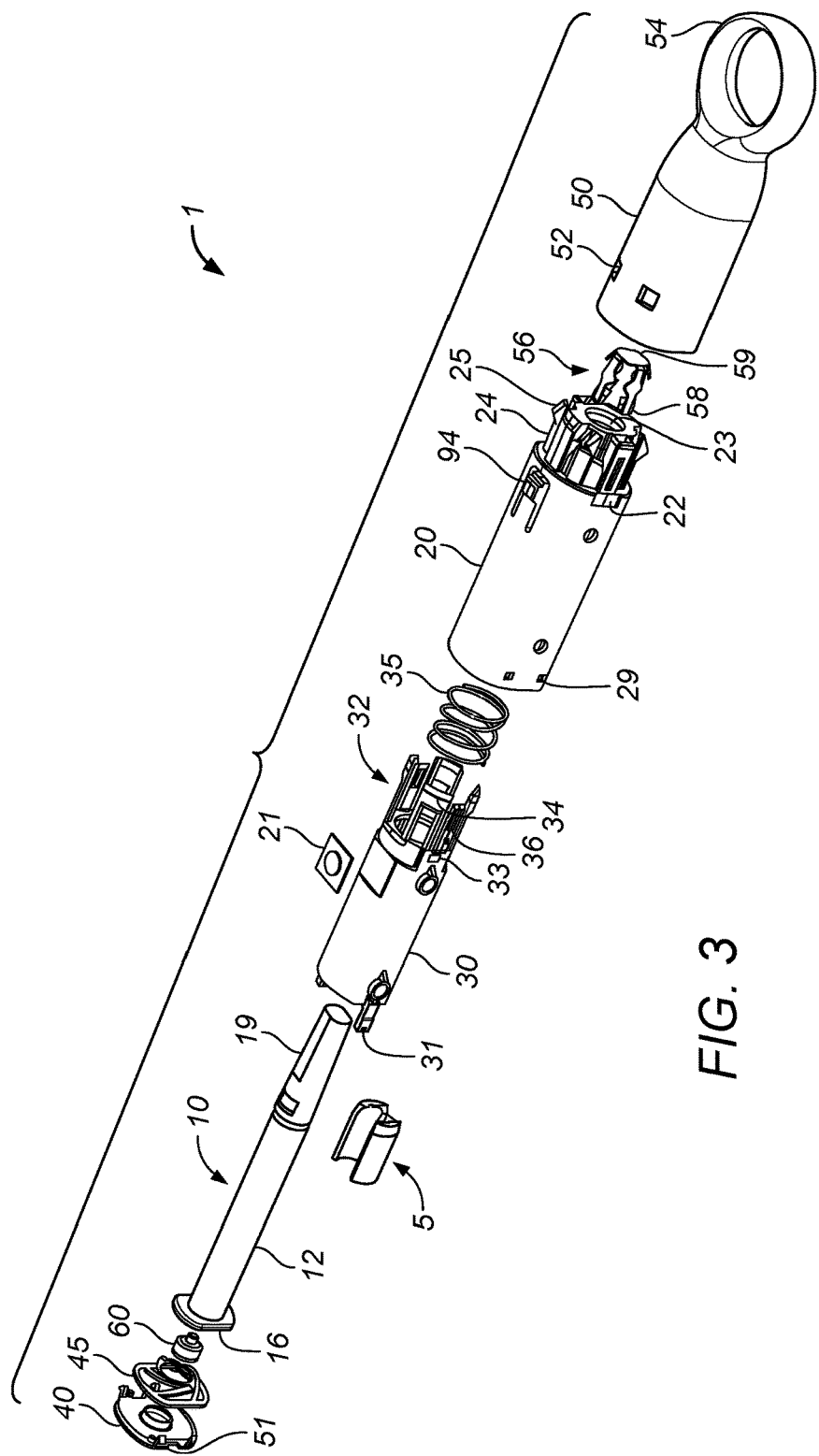
FIG. 3 is an exploded view of the cassette unit of FIG. 1.
Figure 4:
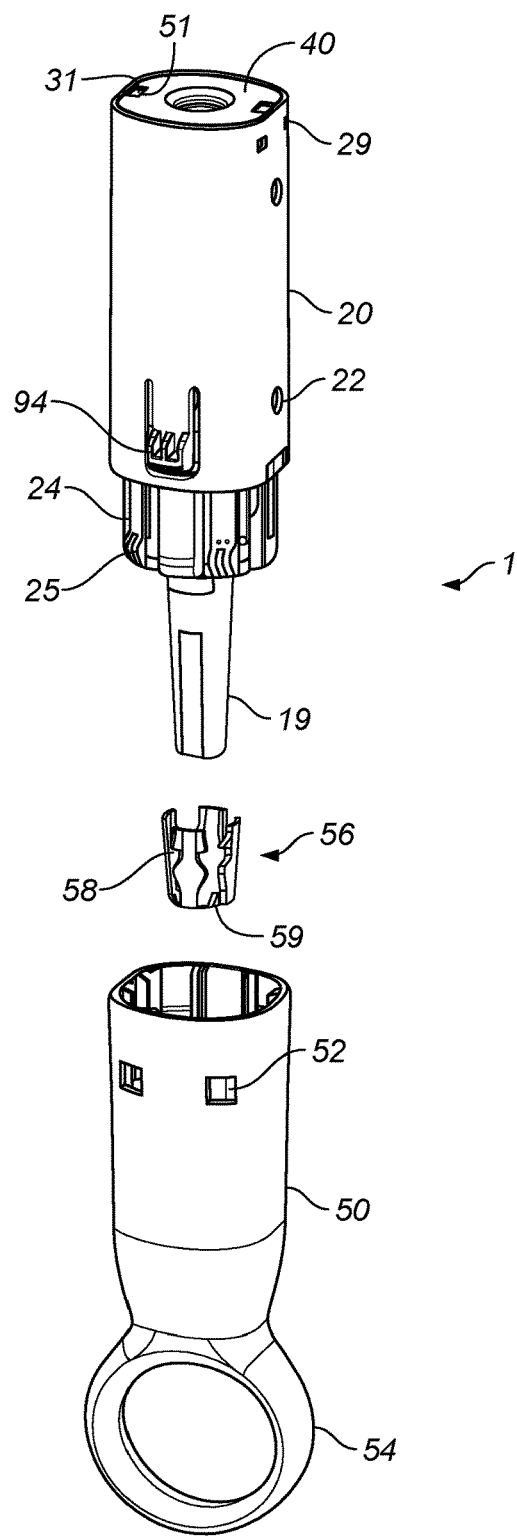
FIG. 4 is a part-exploded view of the cassette unit of FIG. 1 showing in greater detail the relation between needle cover, needle cover gripper and removable cap.

FIGS. 1 to 4 show a cassette unit 1 of an injector herein arranged for use with a 1 ml syringe 10 that contains a liquid drug formulation (not shown). The cassette unit 1 comprises an elongate form cassette unit housing 20 having an end cap 40 that is arranged for receipt of the syringe 10 and is sized and shaped for this purpose. The cassette unit housing 20 is provided with a viewing window 22 that allows for viewing of a 'used cassette flag' 33 provided to inner housing sleeve 30 to provide a visual indication of use, the operation of which will be described in more detail hereinafter. The cassette unit housing 20 is further provided with security label 21, which may in aspects be an RFID tag label for use in verification purposes. The cassette unit 1 is provided with a removable cap 50 that is arranged to engage the needle cover 19 of the syringe 10 that is shown at FIGS. 1 and 2 in the capped position. The cap 50 is provided at the brim thereof with a peripheral arrangement of through-hole (i.e. socket like) first engagement features 52 (not visible on FIG. 2). The cap 50 is shaped to define a ring pull 54 for receipt by the finger of a user.

Needle cover gripper 56 in the form of a cage-like (or 'flower') structure and defining plural gripping elements 58 arranged about a central hub 59 is further provided to the removable cap 50. Such gripping elements 58 are arranged for gripping of the rigid needle sheath shield 19 on removal of the removable cap 50 such that removal of the cap 50 also results in removal of the rigid needle sheath shield 19 and needle sheath 17 enclosed thereby, and hence, unsheathing of the needle tip 15.

The gripping ring 54 of the removable cap defines a finger aperture to receive a patient's thumb or other preferred finger for pulling the removable cap away from the cassette unit 1 to expose the needle 14. In certain embodiments, the finger aperture is adapted to receive a hook that some patients use to pull the removable cap 50 away from the cassette unit 1. The removable cap 50 with gripping ring 54 makes it easier for patients to engage and disengage the needle cover 17 and rigid needle shield 19 from the syringe barrel 12 as it does not require the patient to contort their fingers by pressing on the sides of a narrow needle cover 17/19. As noted before, the present injector is intended for use by patients having compromised manual dexterity who may therefore experience difficulty pulling a conventional needle cover 17 and/or rigid needle shield 19 off the syringe 10 before self-injection. The gripping ring 54 addresses this need by allowing the patient to simply put the thumb or other preferred finger through the finger aperture 54 and pull on the removable cap to thereby remove the needle cover 17 and rigid needle shield 19.

The syringe 10 is of a standard 1 ml type and comprises a barrel 12 with end flange 16 for holding a liquid drug formulation; a hollow needle 14 at one end of the barrel 12; and a syringe plunger 18 in the form of a rubber stopper that is arranged for axial movement within the barrel 12 such as to enable the liquid drug formulation to be expelled through the hollow needle 14. As shown at FIG. 2, the syringe plunger 18 is at the 'pre-use' position. The hollow needle 14 defines a needle bore, which is of circular cross-section (e.g. 23G, 25G or 27G diameter) and a needle tip 15. The needle tip 15 is sheathed by needle sheath 17, which is also provided with rigid needle sheath shell 19. More detail of this relationship is now described by reference to FIGS. 6a to 7b, which illustrate an exemplary arrangement of needle sheath 17 and needle cover 19.

Figure 6A:
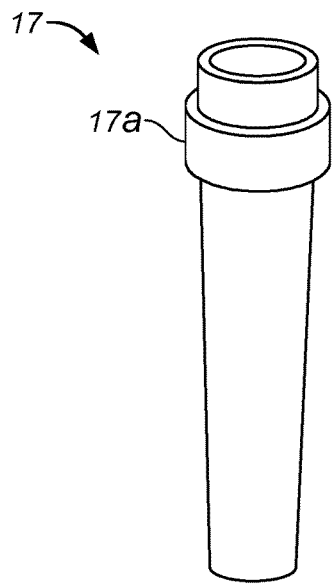
FIGS. 6a and 6b are perspective and cross sectional view of a first needle cover for use with the cassette unit of FIGS. 1 to 4.
Figure 6B:
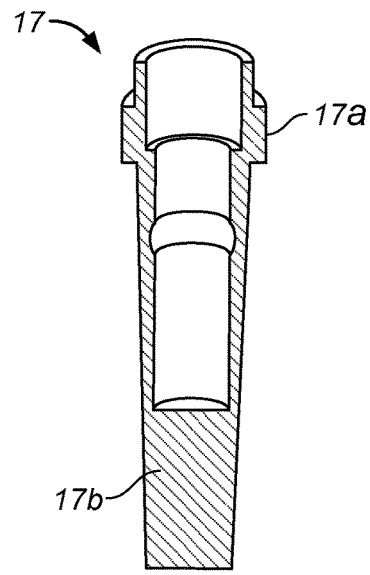

FIG. 6a depicts a perspective view of an exemplary embodiment of a sheath-like needle cover 17, which is cylindrical in shape and defines a shoulder 17a at the rear end. The needle sheath 17 may be made out of rubbery material that allows a portion of the connector 56 to dig into the outer surface thereof, such as that defined by the shoulder 17*a* to permanently engage the needle sheath 17 to the connector 56. FIG. 6*b* shows a cross sectional view of the same needle sheath 17. As depicted, the needle cover 17 includes a needle receiving portion 17*b* that is arranged in use, for piercing receipt of the tip 15 of the needle 14 as for example, shown at FIG. 2. In embodiments, the needle receiving portion 17*b* is made from butadiene rubber. In certain embodiments, the needle sheath 17 is hollow, but other shaped arrangements of the interior of the needle sheath 17 are also possible.

Figure 7A:
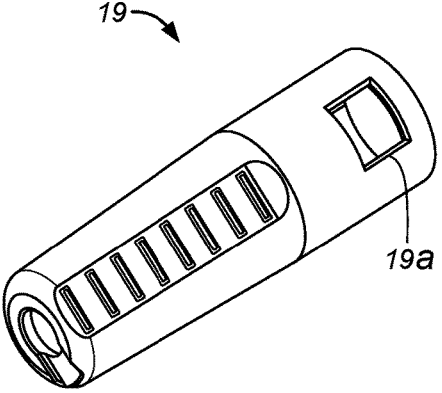
FIGS. 7a and 7b are perspective and cross sectional view of a rigid needle shield for use with the needle cover of FIGS. 6a and 6b.
Figure 7B:
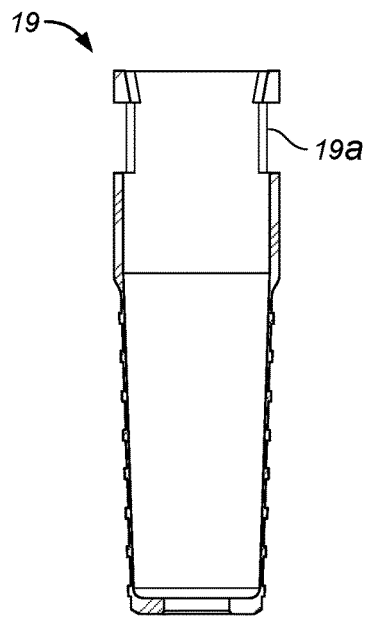

FIGS. 7*a* and 7*b* show views of a rigid needle shield 19 for use with the needle sheath 17 of FIGS. 6*a* and 6*b*. Rectangular openings 19*a* are provided at the rear end of the needle shield for receipt of the shoulder 17*a* of the needle sheath 17 to enable the forming of a needle cover as may be seen at FIG. 2.

The cassette unit housing 20 of the cassette unit 1 is arranged to define a cassette unit housing cavity that is sized and shaped for generally fixed receipt of the syringe 10. The cassette unit housing 20 defines at its forward end a needle delivery aperture 23 through which in use, the hollow needle 14 of the syringe 10 and a portion of the glass hub thereof protrudes on removal of the cap 50 there from. The cassette unit housing 20 defines at its rearward end an end cap 40 adjacent to which the end flange 16 of the syringe 10 seats.

The cassette unit housing 20 is provided with a radial arrangement of first engagement features in the form of movable locking legs 24 defining angled tips 25 (not visible on FIG. 2) thereon arranged for reversibly engaging the corresponding radial arrangement of second engagement features in the form of socket through holes 52 of the removable cap 50 for reversible lock engagement of the removable cap 50 to the cassette unit housing 20.

The cassette unit 1 is provided with an inner housing sleeve 30 for sleeved receipt of the syringe 10. The rear part of the inner housing sleeve 30 is provided with a spaced pair of rearward protruding arms 31. The inner housing sleeve 30 also forms a shuttle lock control feature 32 defining a radial arrangement of blocking elements 34 for selectively blocking movement of the movable locking legs 24 of the cassette unit housing 20 relative to the socket holes 52 of the cap 50, thereby providing for selective control of cap locking/unlocking, more details of which are described hereinafter with reference to FIGS. 8*a* to 11*c*.

Figure 5A:
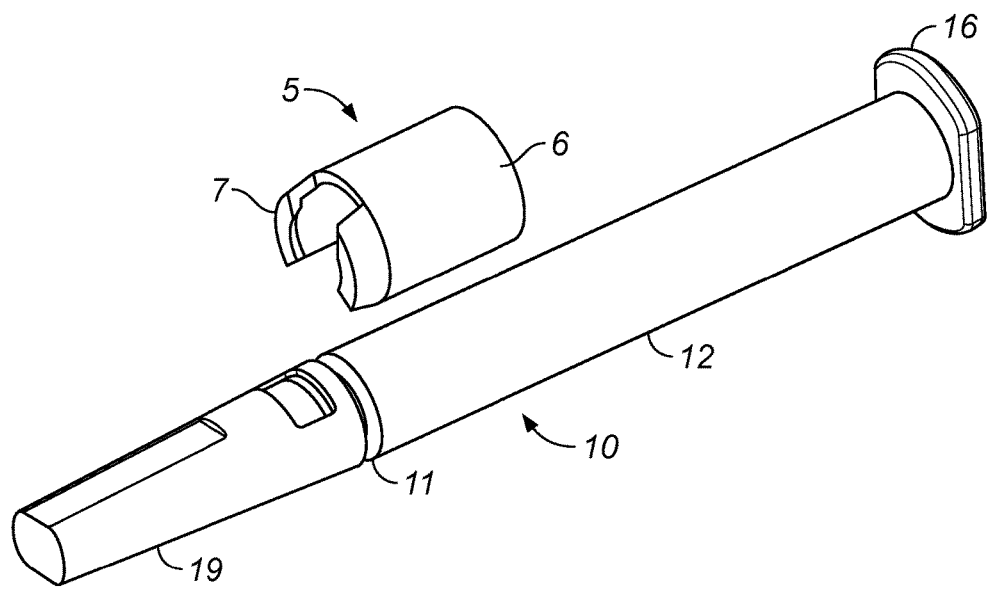
FIG. 5a is a part-exploded view of a syringe with shoulder support assembly suitable for use with the cassette unit of FIGS. 1 to 4.
Figure 5B:
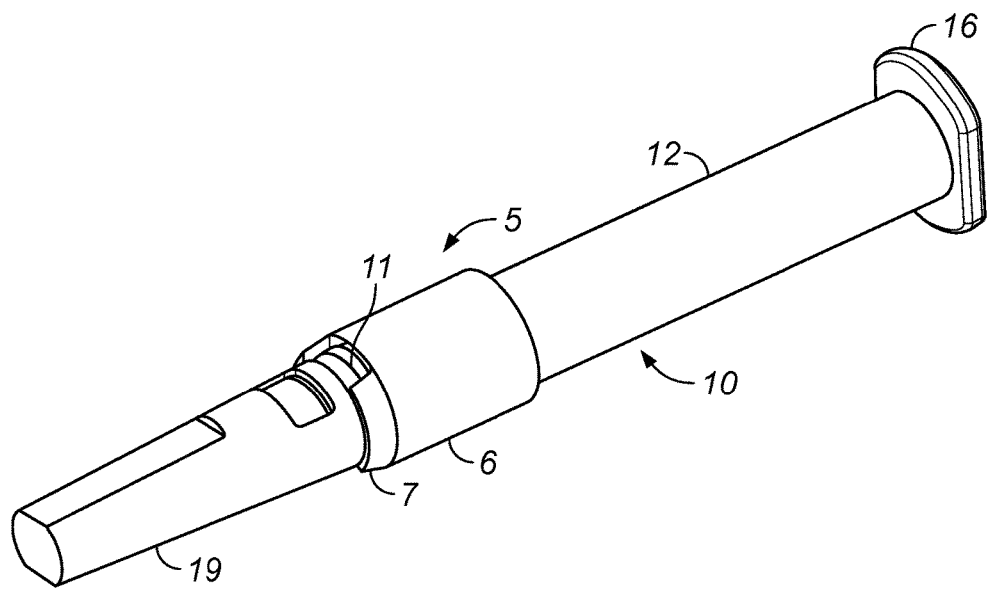
Figure 5C:
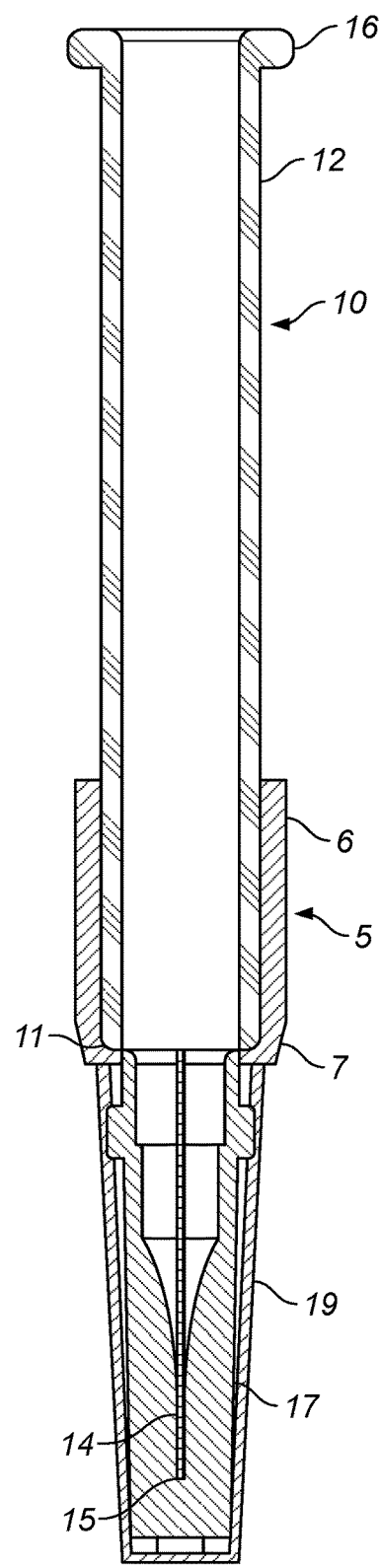

Applicant has found that to reduce the risk of the syringe 10 fracturing under the loads associated with injecting the drug, it is important for a majority of the load path to travel through the forward shoulder 11 of the syringe barrel 12 and lesser load to pass through the flange 16 at the rear end thereof. Thus, as further shown at FIGS. 5*a* to 5*c* but with syringe plunger 18 absent, the syringe 10 of the cassette unit 1 additionally comprises a shoulder support feature 5 for supporting the forward shoulder 11 of the syringe. The shoulder support feature 5 may also used to adapt a 1 ml syringe for use in the cassette unit 1. It supports the 1 ml syringe shoulder 11, and transmits the load through to the same surface that would support a 2.25 ml syringe shoulder directly.

The shoulder support feature 5 may be seen to comprise a split-barrel 6 that is sized and shaped for receipt by the syringe barrel 12 and a forward split lip 7 that is arranged to locate in snap-fit fashion between the rigid needle sheath shell 19 and the forward shoulder 11 of the syringe 10. In embodiments, the use of such a shoulder support feature 5 is to adapt the smaller diameter 1 ml syringe to the rigid shell 19 designed to support the 2.25 ml syringe shoulder 11.

Within the cassette unit 1, the shoulder support feature 5 for the syringe 10 interacts with the inner wall of the cassette unit housing 20, which thereby acts to constrain the position of the shoulder support feature 5 and syringe 10 within the cassette unit housing 20. The inner wall of the cassette unit housing 20 also prevents the forward split lip 7 of the shoulder support feature 5 from flexing outwards when injection loads are applied to the syringe 10. Thus, the forward shoulder 11 of the syringe 10 effectively captures the forward split lip 7 of the shoulder support feature. Also, the rearward split-barrel part 6 of the shoulder support feature 5 acts to sleeve a portion of the syringe barrel 12.

An additional consequence of this part-sleeved relationship between shoulder support feature 5 and syringe barrel 12 is to increase the effective diameter of the syringe barrel 12. By choice of different sizes, particularly inner diameters, of shoulder support feature 5 different syringe 10 sizes may be accommodated within the same cassette unit housing 20. Thus, the shoulder support 5 may also effectively be used as a syringe size adapter feature.

The syringe plunger 18 is provided with a plunger slaving part 60 that is axially movable within the syringe barrel 12 and for receipt by the rear end of the plunger 18. The syringe plunger 18 is made of a material that is resiliently compressible and the plunger slaving part 60 is made of a less compressible material, typically a rigid material.

Further structural details of the plunger slaving part 60 may be seen by reference to FIGS. 12, 13 and 14*a* to 14*c*. Thus, the plunger slaving part 60 defining a circumferential wall 62 arranged for frictional sliding relationship with the inner wall 12*a* of the syringe barrel 12, a rear drive-receiving face 63 and a front plunger-contacting face 64. The slaving part 60 is arranged to function such that when a load is applied to its drive-receiving face 63 the load is evenly transmitted directly into the plunger 18. As may be seen at FIGS. 13 and 14*b*, the rear drive-receiving face 63 of the plunger slaving part 60 has a central recess 65 for receipt of a drive transfer element. The central recess 65 is shaped such that the drive transfer element is rotatably receivable therein and has a recess form 65 that tapers to a square-cut end 66. The front plunger-contacting face 64 defines a protruding plug end 67 that is arranged for receipt by the rear end of the syringe plunger 18. In embodiments, the plug end 67 is designed to prevent collapse in use, of the plunger 18, which has a cavity in its centre into which a plunger rod may be screwed for manual syringe applications.

The circumferential wall 63 of the plunger slaving part is provided with an evenly spaced radial arrangement of slide restrictors 68 that function to restrict frictional sliding movement thereof in relation to the inner wall of the syringe barrel 18. Each of the slide restrictors comprises a flexible vane 68 arranged to flex slightly in response to frictional sliding movement of the plunger slaving part 60 and to thereby to increase the resistance of the plunger slaving part 60 to frictional sliding movement. In embodiments, the flexible vanes 68 are arranged to increase the initial resistance to forward frictional sliding movement but to impart lesser resistance to said forward frictional sliding movement once movement is underway. In embodiments, the flexible vanes 68 are arranged to more greatly increase the resistance to a backward frictional sliding movement than to the forward frictional sliding movement.

The slaving part 60 is brightly coloured and performs a second function of providing an easy-to-identify visual indicator of the position of the plunger 18 within the syringe 10 so that the patient can visually confirm the drug had been fully injected. The flexible vanes 68 act such as to maintain the plunger slaving part 60 in the 'after use' (i.e. post-injection) position such that this indicator can be relied upon to signal this 'after use' state. In embodiments, the plunger slaving part 60 has a third function; one of tamper evidence: If an attempt is made to access the syringe 10 via the end-cap 40, the plunger slaving part 60 will be pushed out of engagement with the end-cap 40, resulting in visible evidence of tamper.

The cassette unit 1 includes, in capping relationship with a rear opening of the cassette unit housing 20, a cassette unit end-cap 40. Further structural details of the cassette unit end-cap 40 may be seen by reference to FIGS. 12 and 13. The cassette unit end-cap 40 defines a drive transfer element-receiving opening 41 for receipt of a drive rod (part of the manual drive unit, not shown) for providing forward axial drive to the plunger slaving part 60. Four fixing legs 39 with heels 38 locate at spaced intervals about the inner end wall of the end-cap 40 and protrude forwards for fixing receipt (not visible on FIG. 13) with fixing sockets 29 of the cassette unit housing 20.

The cassette unit end cap 40 also defines a spaced pair of cut-away apertures 51 positioned such that when the cassette unit end-cap 40 is in capped relationship with the cassette unit housing 20 the cut-away apertures 51 are in registration with the protruding arms 31 of the inner housing sleeve 30. Each cut-away aperture 51 is designed allow for insertion of a pushing member (e.g. a pin) such that forward pushing force may be applied to the top of the protruding arms 31 to push the inner housing sleeve 30 forward, thereby allowing for actuation of the shuttle lock control 32, as described in more detail hereinafter.

Figure 13:
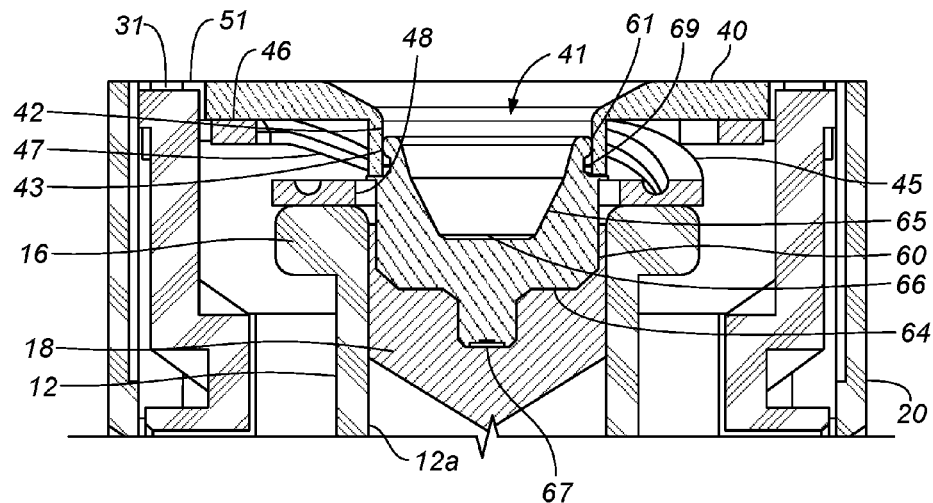
FIG. 13 is a sectional view of the upper part of the cassette unit of FIGS. 1 to 4 showing details of end cap, end cap spring and plunger slaving part interaction with the rearward flange of the syringe within the cassette unit housing.
Figure 14A:
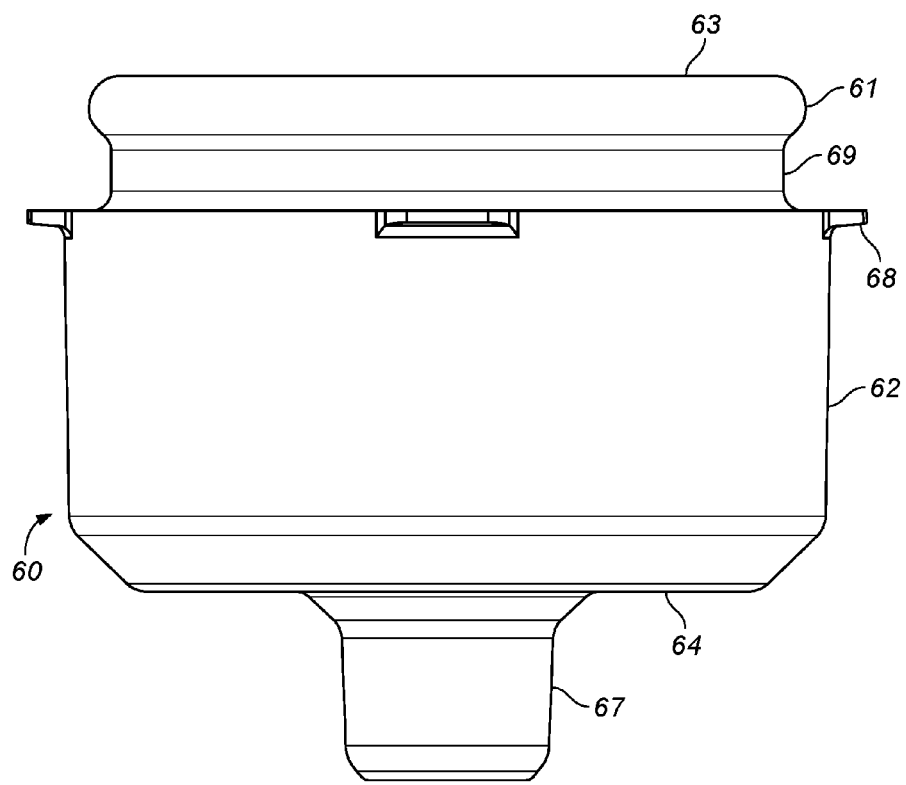
FIGS. 14a to 14c are side, rear plan and front plan views of a plunger slaving part for use with the cassette unit of FIGS. 1 to 4.
Figure 14B:
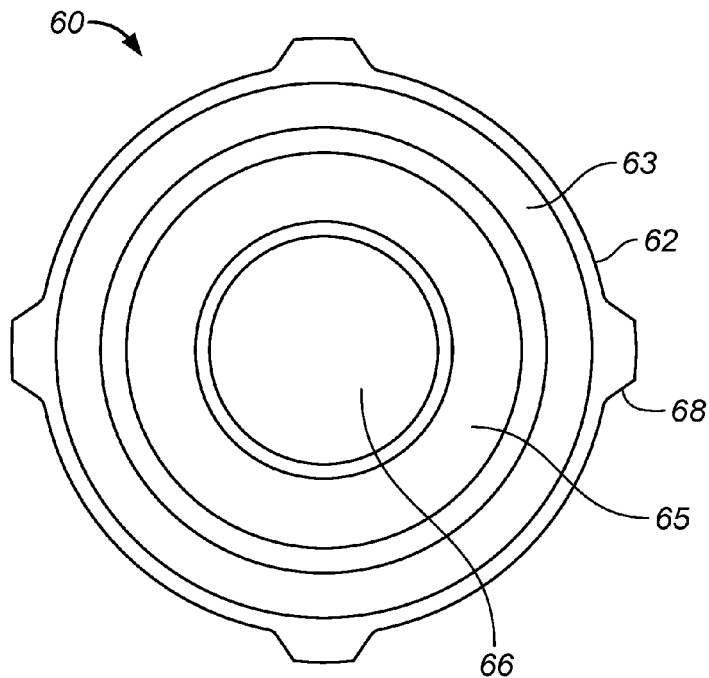
Figure 14C:
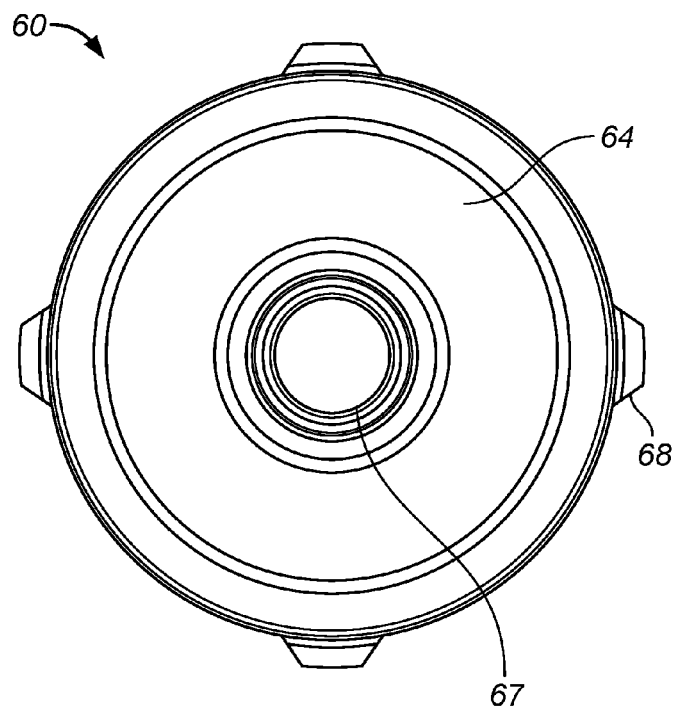
Figure 15A:
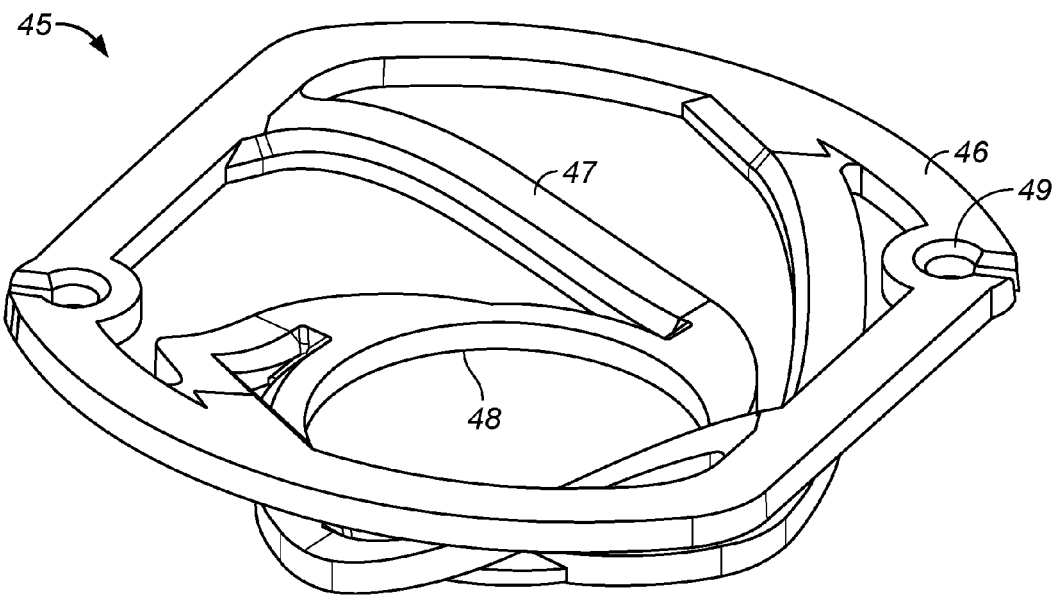
FIGS. 15a to 15d are perspective, side, rear plan and front plan views of an end cap spring for use with the cassette unit of FIGS. 1 to 4.
Figure 15B:
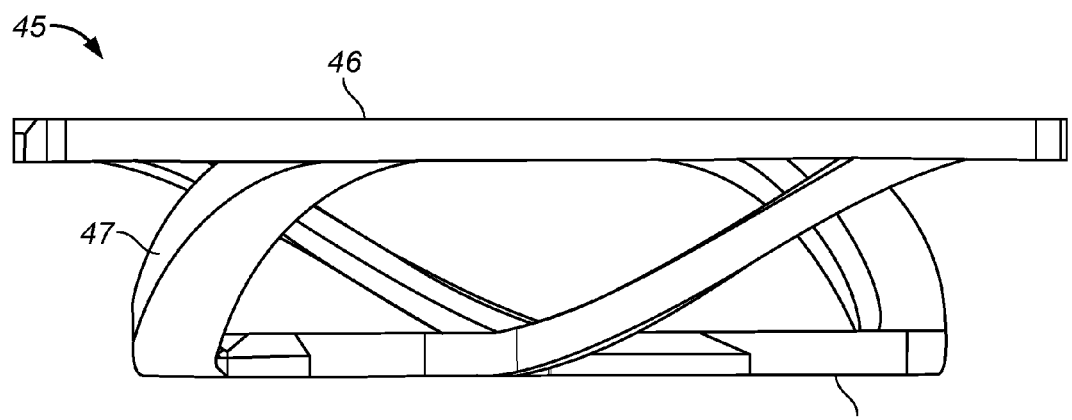
Figure 15C:
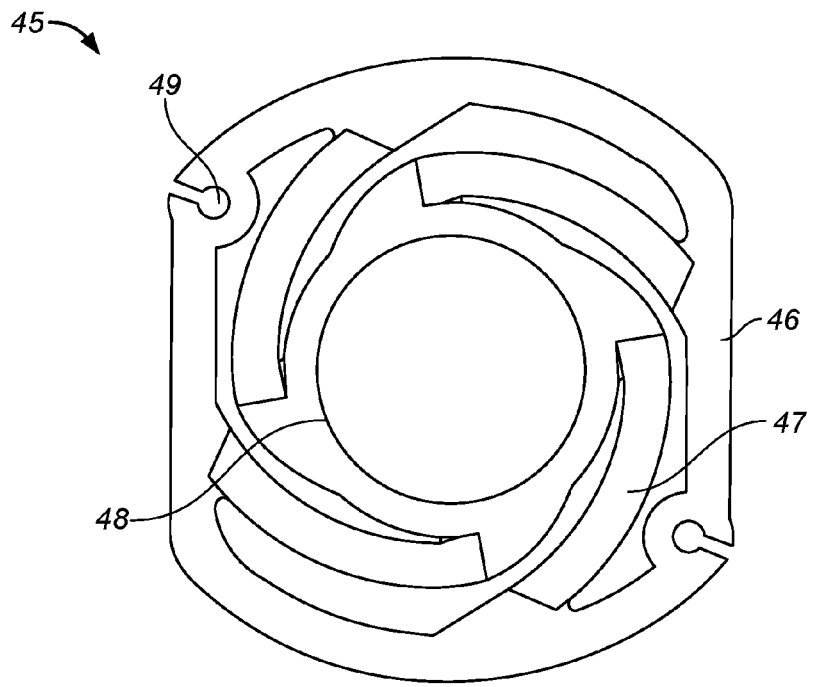
Figure 15D:
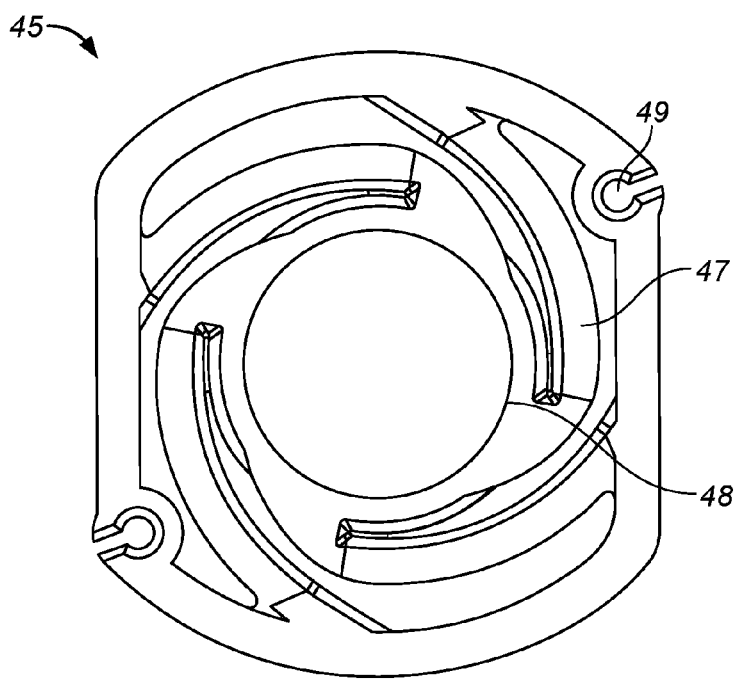

In the pre-use configuration (e.g. as shown at FIGS. 2 and 13), the plunger slaving part 60 is in releasable engagement with the cassette unit end-cap 40. Structurally, the drive transfer element-receiving opening 41 is defined by a periphery, which is provided with a forward skirt 42 and the plunger slaving part 60 is shaped for releasable engagement in the pre-use configuration with the forward skirt 42. In more detail and with particular reference to FIG. 13, the forward skirt 42 is provided with an inner-facing rim 43 and the plunger slaving part 60 defines a circumferential rim 61 and trough 69 shaped for releasable engagement in the pre-use configuration with the inner-facing rim 43 of the end-cap 40. In use, the plunger slaving part 60 is releasable from the cassette unit end-cap 40 in response to forward axial drive provided to said rear drive-receiving face 63, 66 thereof.

The cassette unit 1 additionally comprises an end-cap spring 45 defining a sprung biasing relationship between the cassette unit end-cap 40 and the flange 16 of the syringe 10, thereby urging the syringe 10 forwards in relation to the cassette unit end cap 40. The effect of this sprung relationship is to better hold the syringe 10 within the cassette unit housing 20, and in particular to minimize any potential for the syringe to 'rattle about' within the cassette unit housing 20. It will also be appreciated, particularly when reference is made to FIG. 2, that the effect of such urging forwards of the syringe 10 is also to bring the forward shoulder 11 of the syringe 10 into closer relationship with shoulder support feature 5, which sits between that forward shoulder 11 and the rigid needle sheath cover 19. Overall, thus the forward end of the syringe 10 thus, tends to be more supported. An additional effect of the end-cap spring 45 is to prevent rearward movement of the syringe 10 during needle insertion, ensuring that full insertion depth is achieved.

Further structural details of the end-cap spring 45, which is typically comprised of a polymeric material, may be seen by reference to FIGS. 12, 13 and 15a to 15d. The rear end 46 of the end-cap spring 45 defines an essentially flat profile, which allows it to seat up against the inner end wall of the end-cap 40 where it is held in place by the interaction of pegs 44 on the inner wall of the end-cap 40 with peg-sockets 49 on the rear end 46 of the end-cap spring 45. Sprung arms 47 extends forwards in spiral fashion and meet at circular ring 48 at the forward end of the end-cap spring 45. Within the cassette unit, this ring 48 is sized and shaped to fit about the forward skirt 42 of the end-cap 40 and when the plunger slaving part 60 is engaged with the end-cap 40 (e.g. as shown at FIGS. 2 and 13) about the outer circumferential wall 62 of the plunger slaving part 60.

Figure 8A:
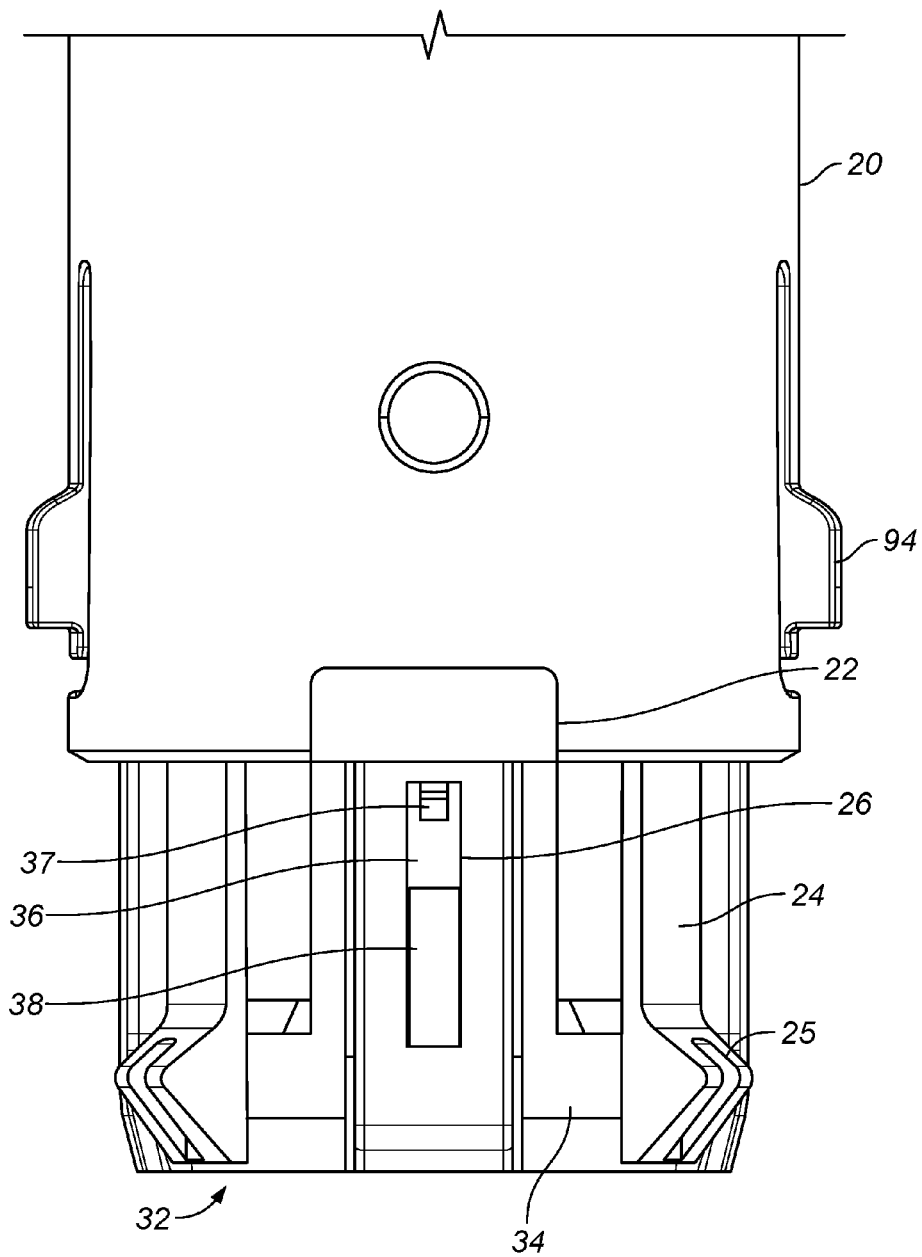
FIGS. 8a and 8b are perspective side-on views of a cassette unit housing and shuttle lock control part-assembly of the cassette unit of FIGS. 1 to 4 at respective, first 'cassette unused' and third 'cassette used' positions.
Figure 8B:
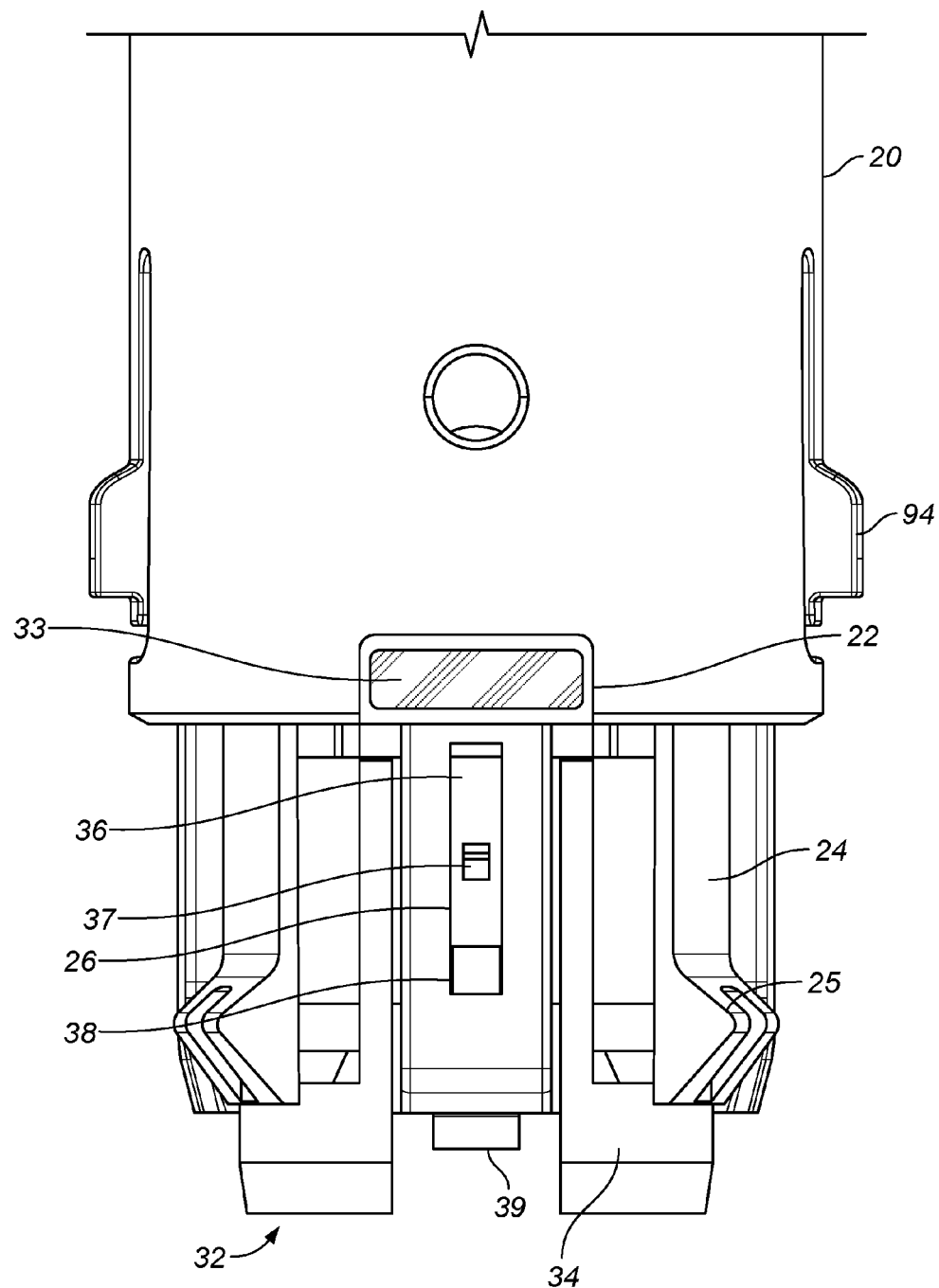
Figure 8C:
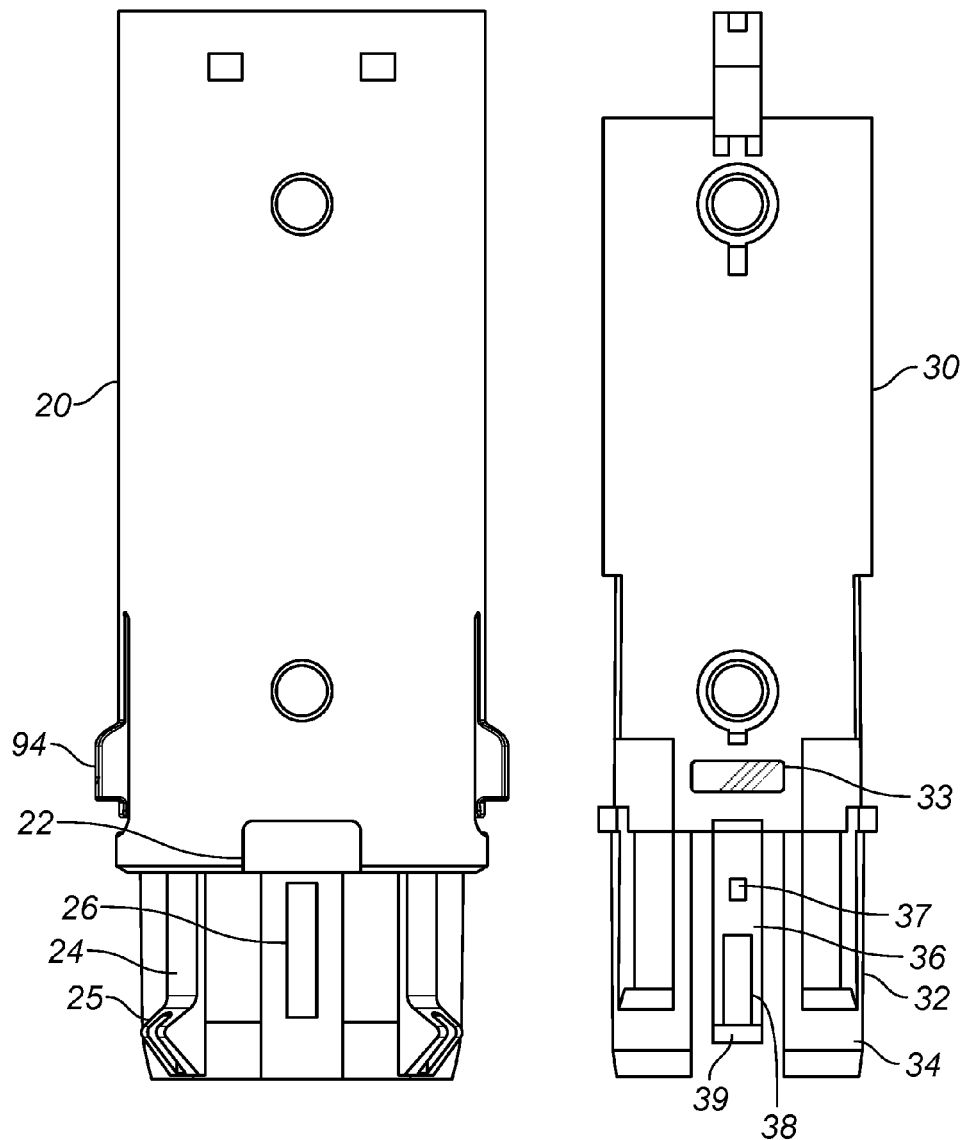
FIG. 8c shows the separate cassette unit housing and shuttle lock control parts of the part-assembly of FIGS. 8a and 8b.

Details of the selective control of cap locking/unlocking of the cassette unit 1 are now described by reference to FIGS. 8a to 11c. It will be noted that for illustrative purposes only, FIG. 8c shows the separate cassette unit housing 20 and shuttle lock control 32 parts of the part-assembly of FIGS. 8a and 8b.

The cassette unit housing 20 is provided with a radial arrangement of first engagement features in the form of axially protruding locking legs 24 having heels defining angled tips 25 movable by flexing action and arranged for reversibly engaging a corresponding radial arrangement of second engagement features in the form of socket through holes 52 of the removable cap 50 (see FIGS. 3 and 4) for reversible lock engagement of the removable cap 50 to the cassette unit housing 20. In a secondary aspect, this arrangement also acts to prevent rotation of the cap 50 relative to the cassette unit housing 20.

The inner housing sleeve 30 defines a shuttle lock control feature 32 comprising a radial arrangement of blocking elements 34 for selectively blocking inwardly flexing movement of the movable locking legs 24 of the cassette unit housing 20 relative to the socket holes 52 of the cap 50, thereby providing for selective control of cap locking/unlocking.

Figure 9A:
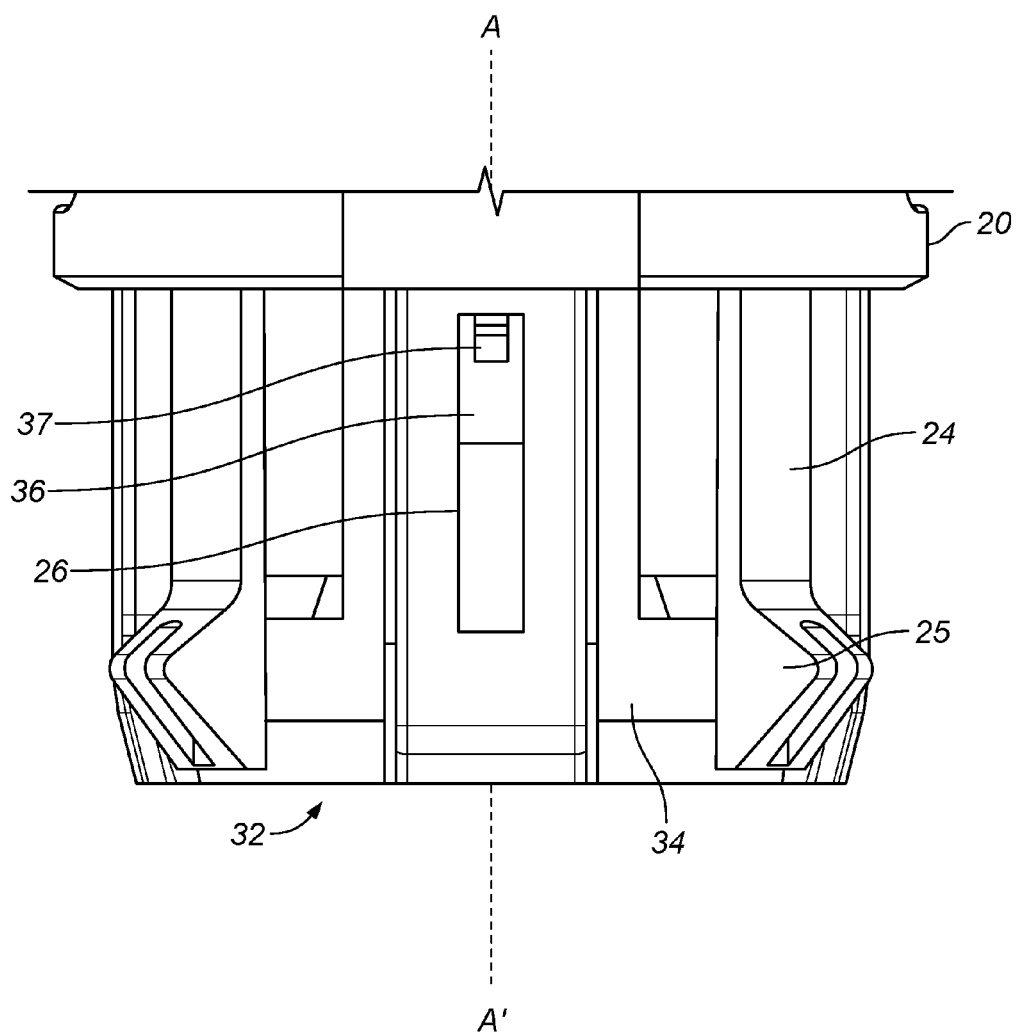
FIGS. 9a to 9c are close-up perspective side-on views of the cassette unit housing and shuttle lock control part-assembly of FIGS. 8a and 8b at respective, first 'cassette unused', second 'cassette unlocked' and third 'cassette used' positions.
Figure 9B:
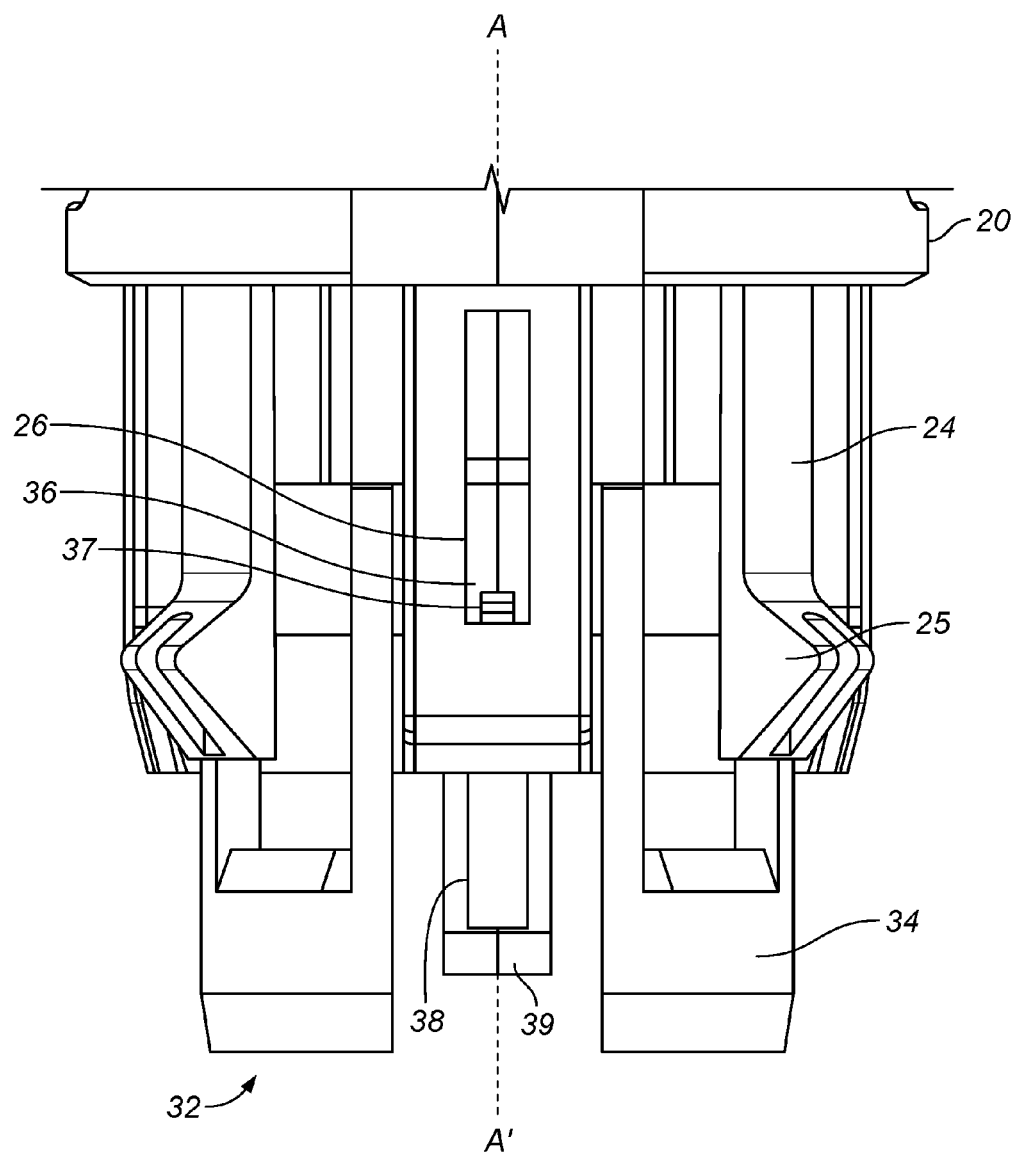
Figure 9C:
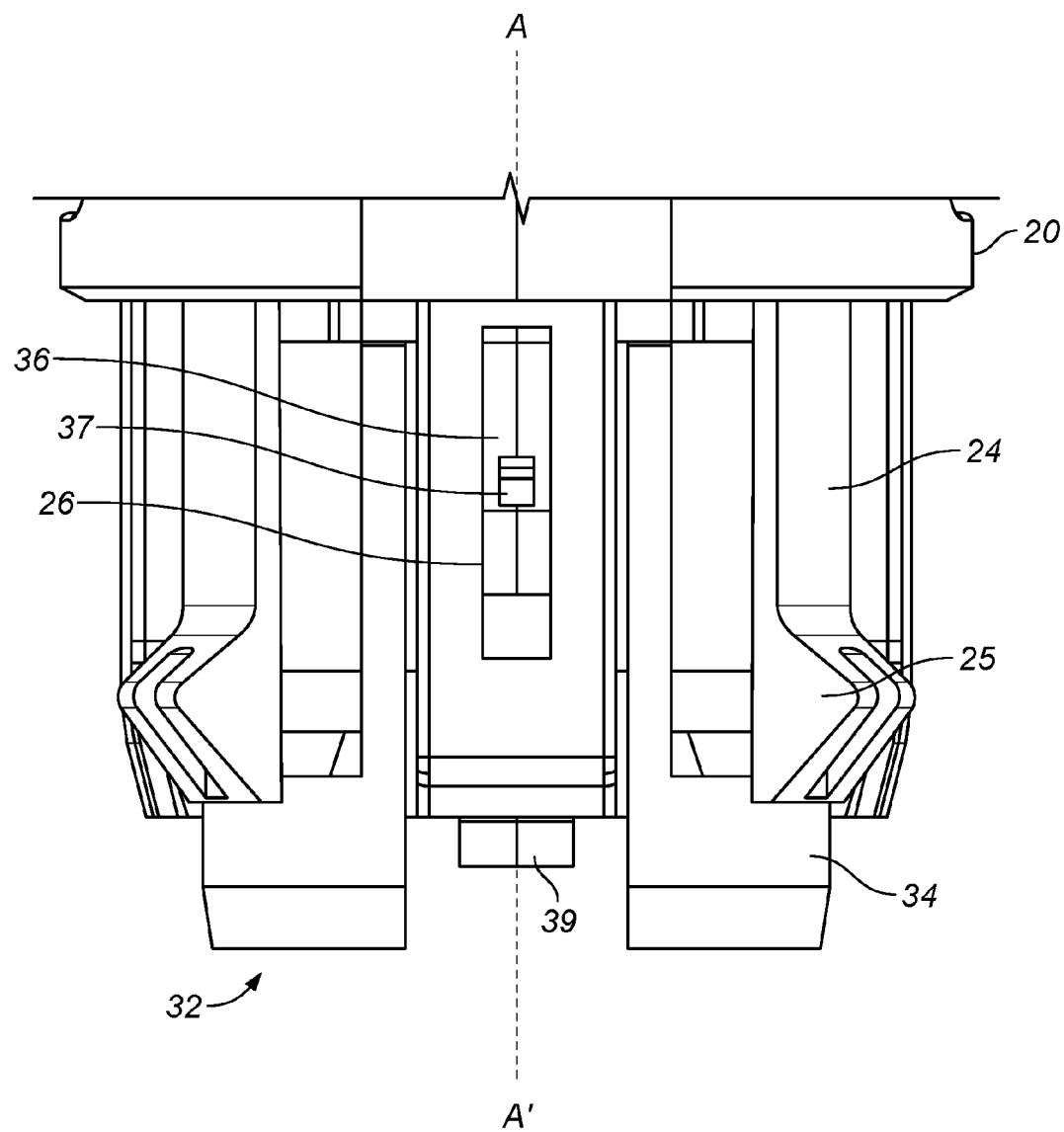

The shuttle lock control 32 is axially movable relative to the cassette unit housing 20 in between three positions, namely:
 (i) as shown at FIGS. 8a, 9a, 10a and 11a, a first 'cassette unused' position, in which the blocking elements 34 block movement of the locking legs 24 of the cassette unit housing 20 relative to the socket through holes 52 of the removable cap, thereby keeping the removable cap 50 in locked relationship to the cassette unit housing 20;
 (ii) as shown at FIGS. 9b, 10b and 11b, a second 'cassette unlocked' position, in which the blocking elements 34 no longer block movement of the locking legs 24 of the cassette unit housing 20 relative to relative to the socket through holes 52 of the removable cap 50, thereby allowing for unlocking of the removable cap 50 from the cassette unit housing 20 and for removal and replacement thereof; and
 (iii) as shown at FIGS. 8b, 9c, 10c and 11c, after replacement of the removable cap 50, a third 'cassette used' position, locating intermediate the first and second positions, in which the blocking elements 34 again block movement of the locking legs 24 of the cassette unit housing 20 relative to the socket through holes 52 of the removable cap, thereby restoring the locked relationship between the removable cap 50 and the cassette unit housing 20.

Movement of the shuttle lock control 32 is typically achieved by application of forward pushing force to the top of the protruding arms 31 of inner housing sleeve 30 to push the inner housing sleeve 30 and the shuttle lock control 32 forward. This is typically achieved by insertion of a pushing member (e.g. a pin) into each of the cut-away apertures 51 of the cassette unit end cap 40 to push forward the protruding arms 31 of the inner housing sleeve 30.

The shuttle lock 32 is biased by the action of shuttle lock spring 35 from the second position to the third position. Thus, in a typical use operation, on removal of the removable cap 34 the shuttle lock 32 is in the second position; during use of the cassette for injection the shuttle lock 32 is biased into the third position; and during replacement of the removable cap 50 the shuttle lock is in the second position.

The shuttle lock control 32 is further provided with a pair of diametrically oppositely located axial position locators 36, each of which is arranged to define three distinct axial positions of the shuttle lock control 32 relative to cassette unit housing 20 and corresponding to said first, second and third positions. Each axial position locator 36 comprises an axial protrusion having a follower 37 arranged thereon for receipt within a corresponding axial track 26 of the inner cassette unit housing 20 such as to define an axial track-follower relationship between the shuttle lock control 32/inner housing sleeve and the cassette unit housing 20. The previously defined first and second positions correspond to the opposite extremes of this axial track-follower relationship.

Figure 10A:
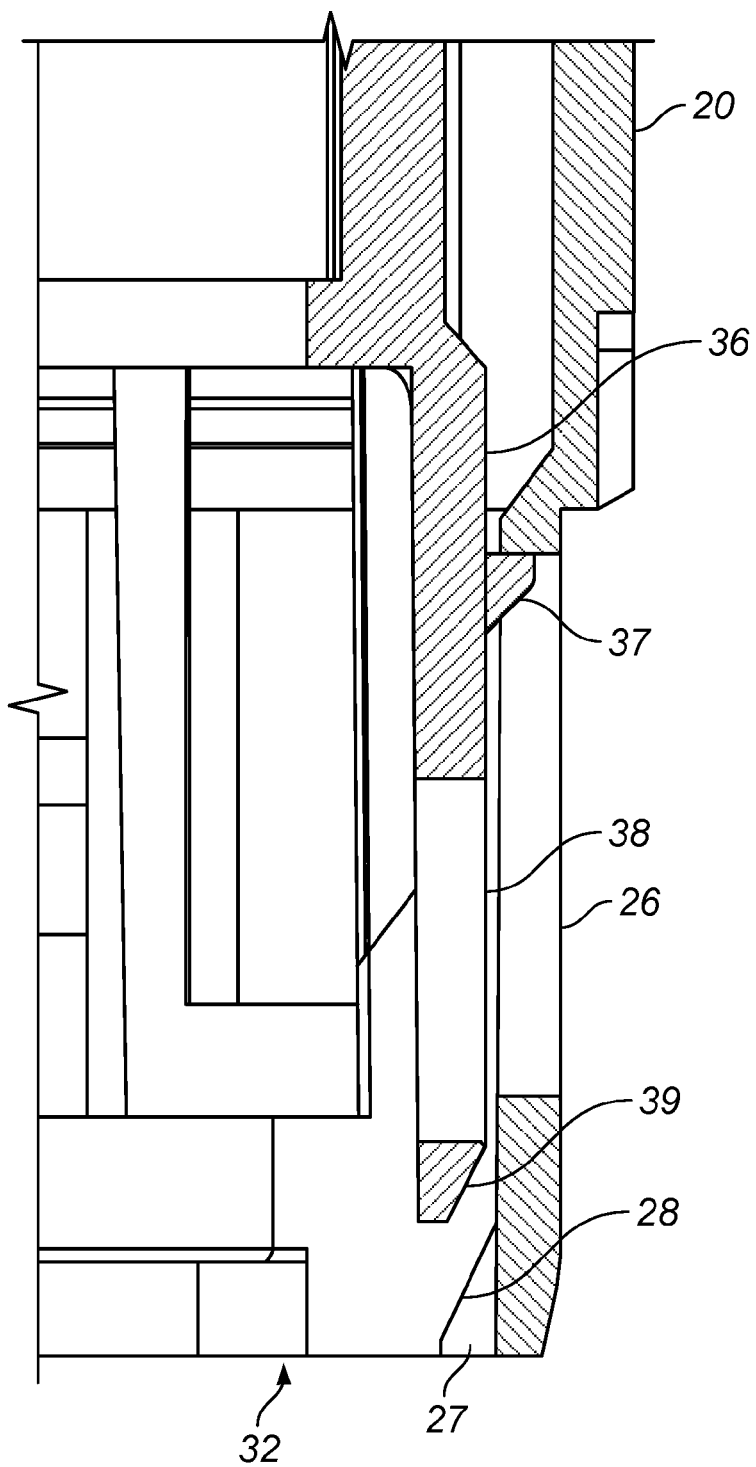
FIGS. 10a to 10c are sectional views taken along the line A-A' of FIGS. 9a to 9c of the cassette unit housing and shuttle lock control part-assembly of FIGS. 8a and 8b at respective, first 'cassette unused', second 'cassette unlocked' and third 'cassette used' positions.
Figure 10B:
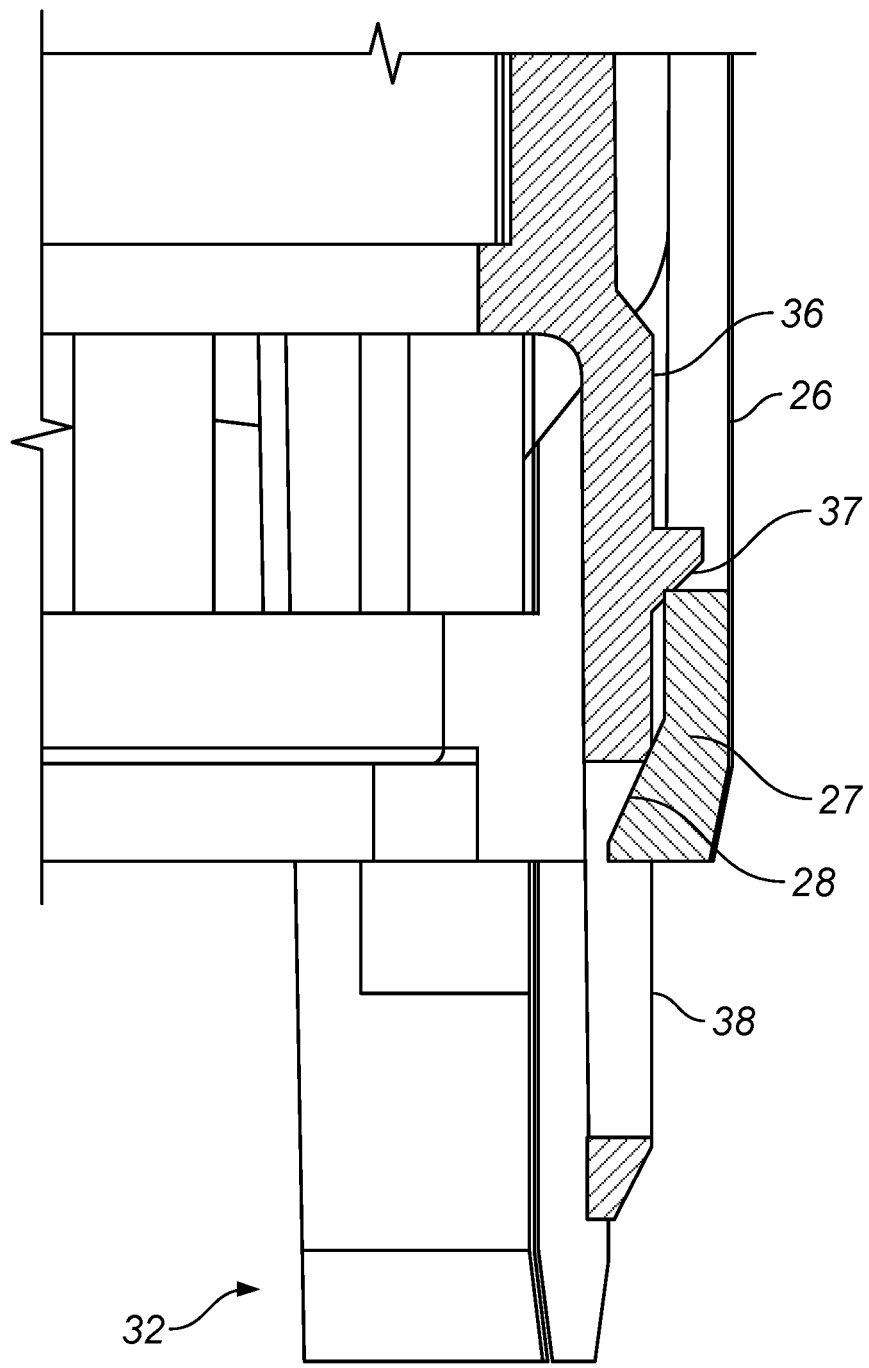
Figure 10C:
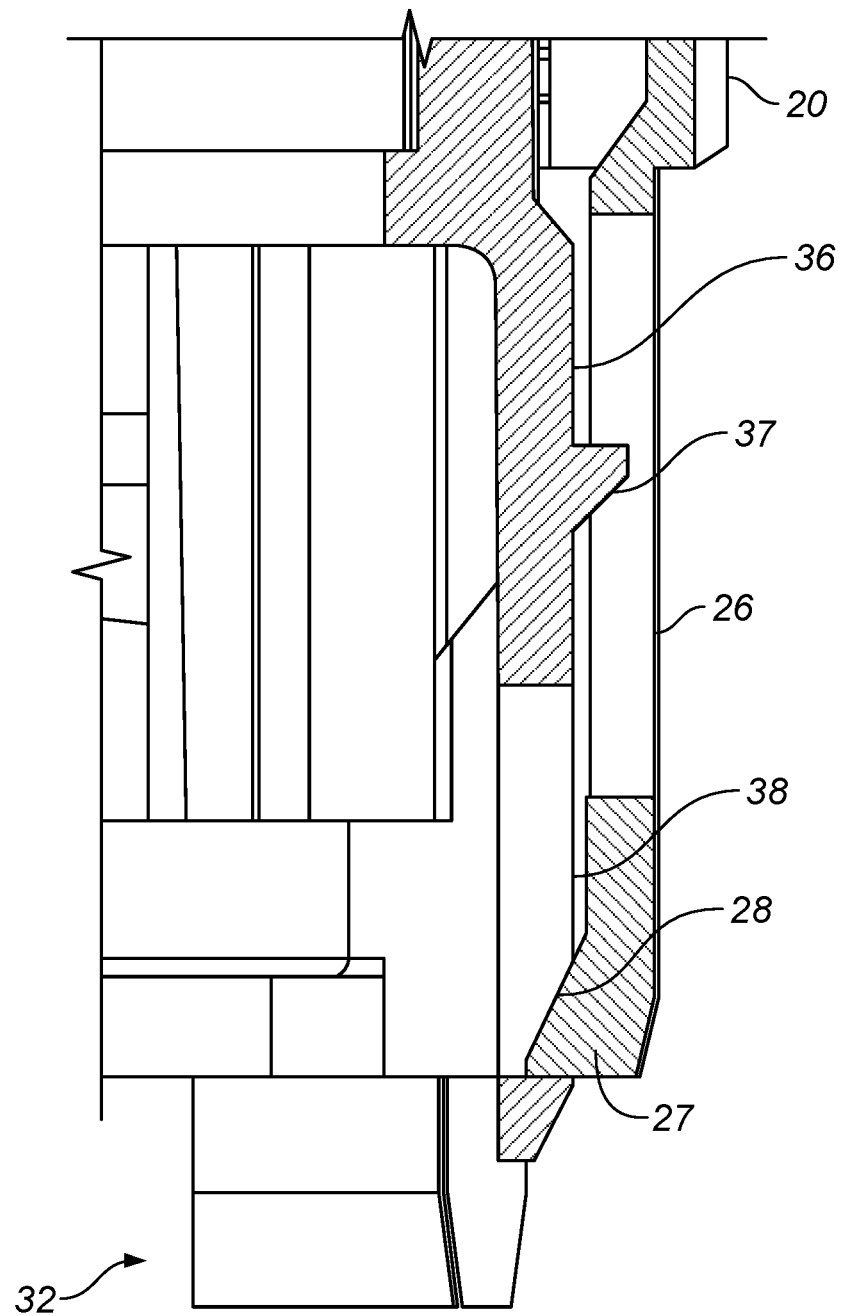
Figure 11A:
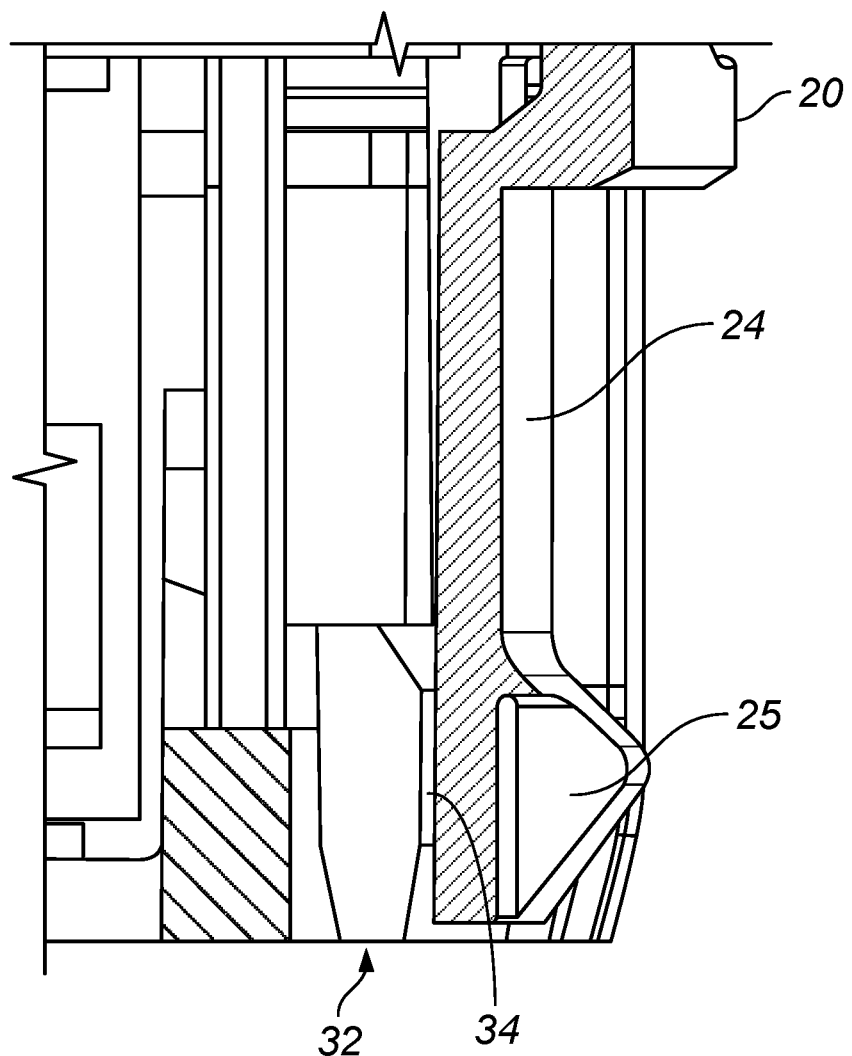
FIGS. 11a to 11c are sectional views taken along the plane bisecting locking arm 24 of FIGS. 9a to 9c of the cassette unit housing and shuttle lock control part-assembly of FIGS. 8a and 8b at respective, first 'cassette unused', second 'cassette unlocked' and third 'cassette used' positions.
Figure 11B:
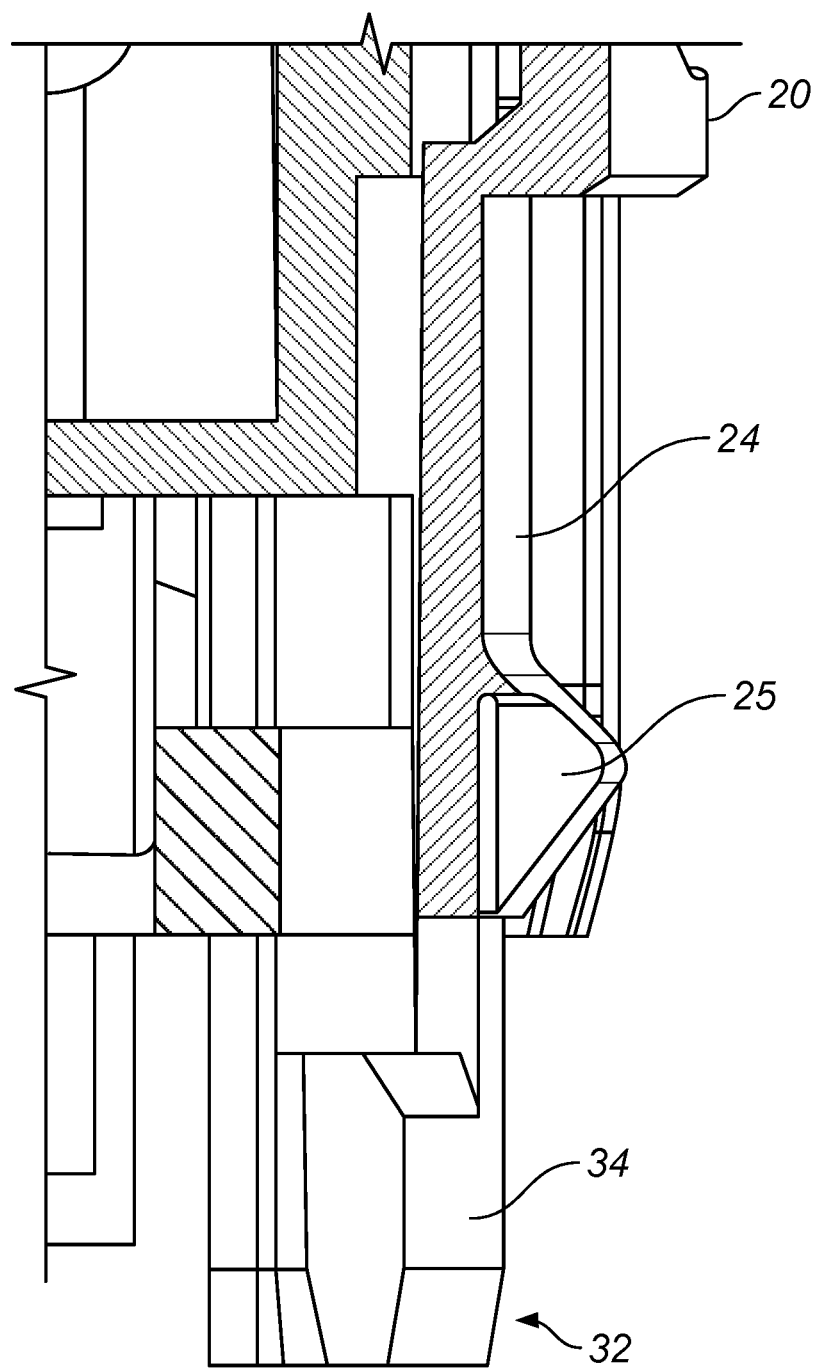
Figure 11C:
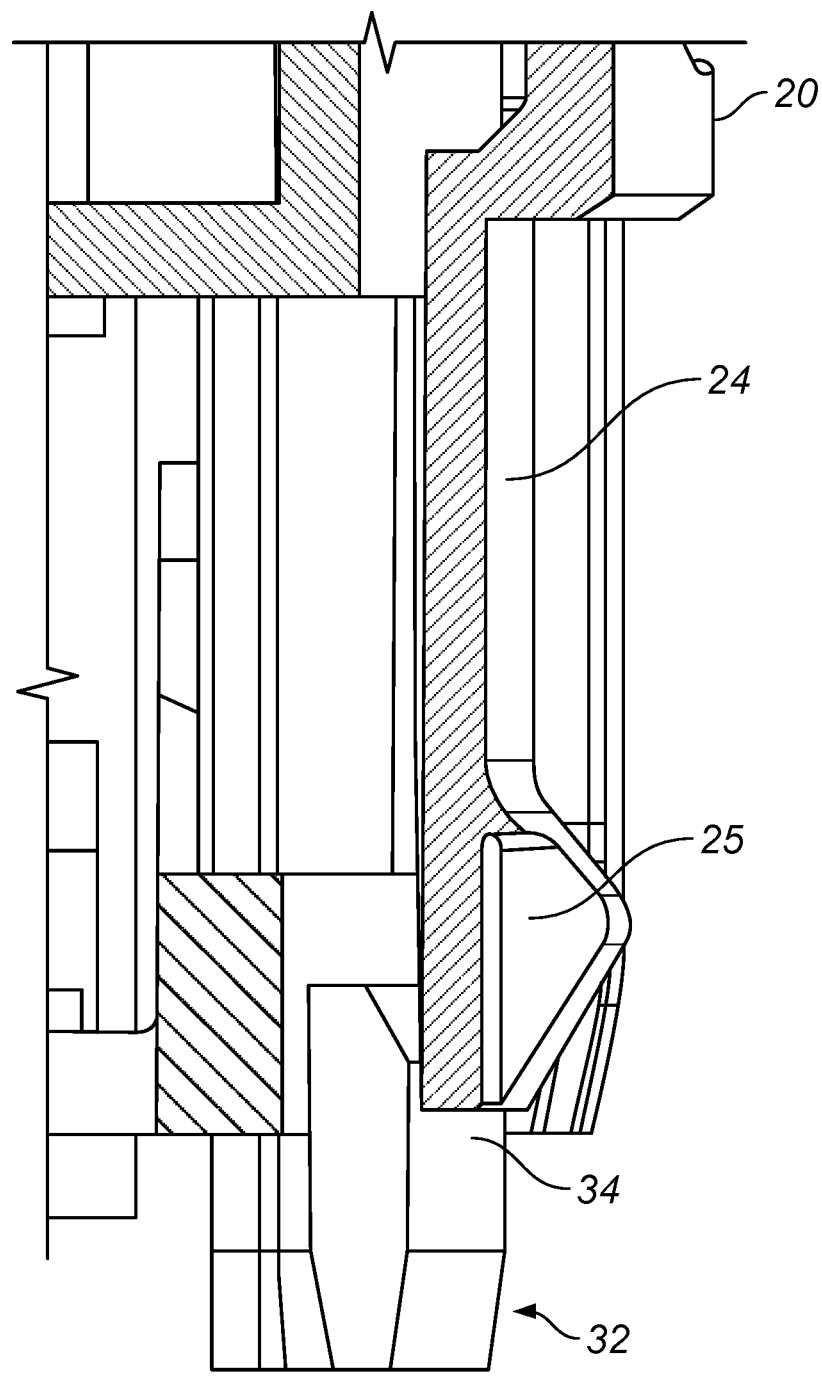
Figure 12:
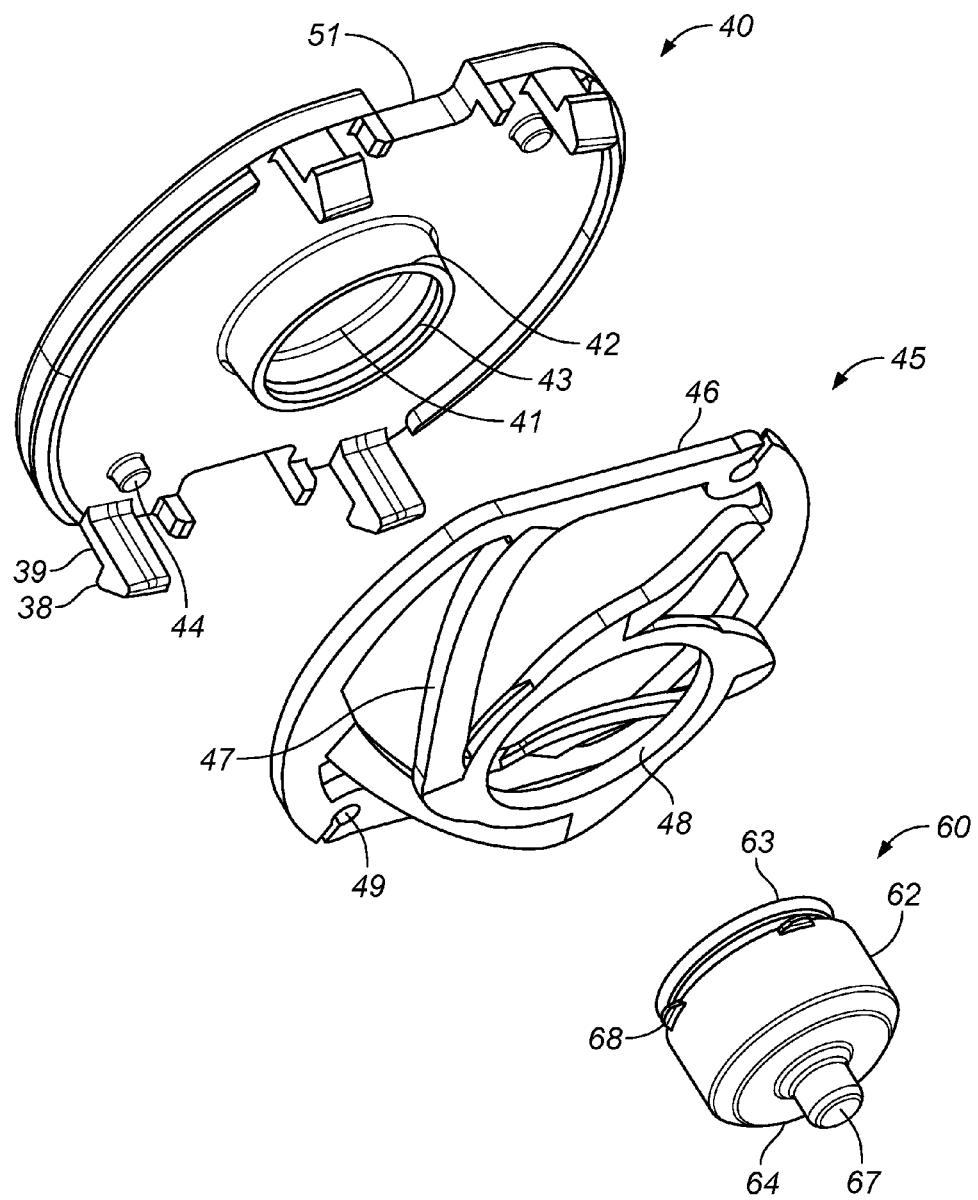
FIG. 12 is a perspective exploded view of an end cap, end cap spring and plunger slaving part for use with the cassette unit of FIGS. 1 to 4

In a further structural detail, and with particular reference to FIGS. 10a to 10c, each axial position locator 36 further comprises a first latch element in the form of an axial latching slot 38 arranged for selective latching relationship with a corresponding second latch element in the form of a latching foot 27 of the cassette unit housing 20. The latching foot 27 of the cassette unit housing 20 is movable within the axial latching slot 38 of the axial position locator 36 such as to define an axial foot-in-slot relationship between these parts.

As shown at FIG. 10a, in the first position the axial latching slot 38 and latching foot 27 are in non-latching relationship and as shown at FIGS. 10b and 10c respectively, in the second and third positions the axial latching slot 38 and latching foot 27 are in latching relationship, wherein the second (FIG. 10b) and third (FIG. 10c) positions respectively correspond to opposing slot ends of said axial latching slot 38.

A non-return feature is also provided and arranged such that when the first and second latch elements 38, 27 have come into latching relationship return to a non-latching relationship is prevented. Thus, a forward ramped surface 39 is provided at the forward end of the first latch element, in which the axial latching slot 38 is defined, and a corresponding ramped surface 28 is defined at latching foot 27 such as to facilitate ramping over each other when coming into latching relationship. However, once the latching foot 27 has been received within the axial latching slot 38 (second and third positions, see FIGS. 10b and 10c) it is retained there and may not return to the first position (FIG. 10a).

In use, the cassette unit 1 is initially in the first 'cassette unused' position, in which the angled tip 25 of each flexibly resilient locking leg 24 of the cassette unit housing 20 protrudes slightly into a socket through-hole first engagement feature 52 of the removable cap 50. It will be appreciated that this engaging interaction of the angled tip 25 of locking leg 24 with socket through-hole feature 52 effectively prevents movement (including rotation) of the cap 50 relative to the cassette unit housing 20. In this first position, the blocking elements 34 block movement of the locking legs 24 of the cassette unit housing 20 relative to the socket through holes 52 of the removable cap, thereby keeping the removable cap 50 in locked relationship to the cassette unit housing 20.

In the second 'cassette unlocked' position, this engaging interaction can be released by pushing each locking leg 24 inwards, thereby clearing the angled tip 25 from engaging relationship with each relevant socket through-hole 52. Such inward pushing action on the locking leg 24 can be achieved (in the cap unlocked position of FIGS. 9b, 10b and 11b) by pulling the cap 50 forwards and away from the cassette unit housing 20, which results in the angled tip 25 interacting with the wall edges of the through-hole 52 to push the locking leg 24 inwards.

After cap removal and during injected use, the action of shuttle lock spring 35 results in adoption of the third position until such time as the removable cap 50 is replaced when the second position is again adopted during cap 50 replacement. After cap replacement, the third position is again adopted. The shuttle lock control 32 is marked with a 'used cassette' flag 33 arranged to be brought into registration with the indicator opening of the cassette unit housing 20 at the third 'cassette used' position (see FIG. 8b) as a visual indicator that the cassette has been used.

The cassette unit 1 further comprises flexible locking arms 94 for locking receipt within locking apertures 96 of a manual drive unit, as will be described hereinafter.

Figure 16:
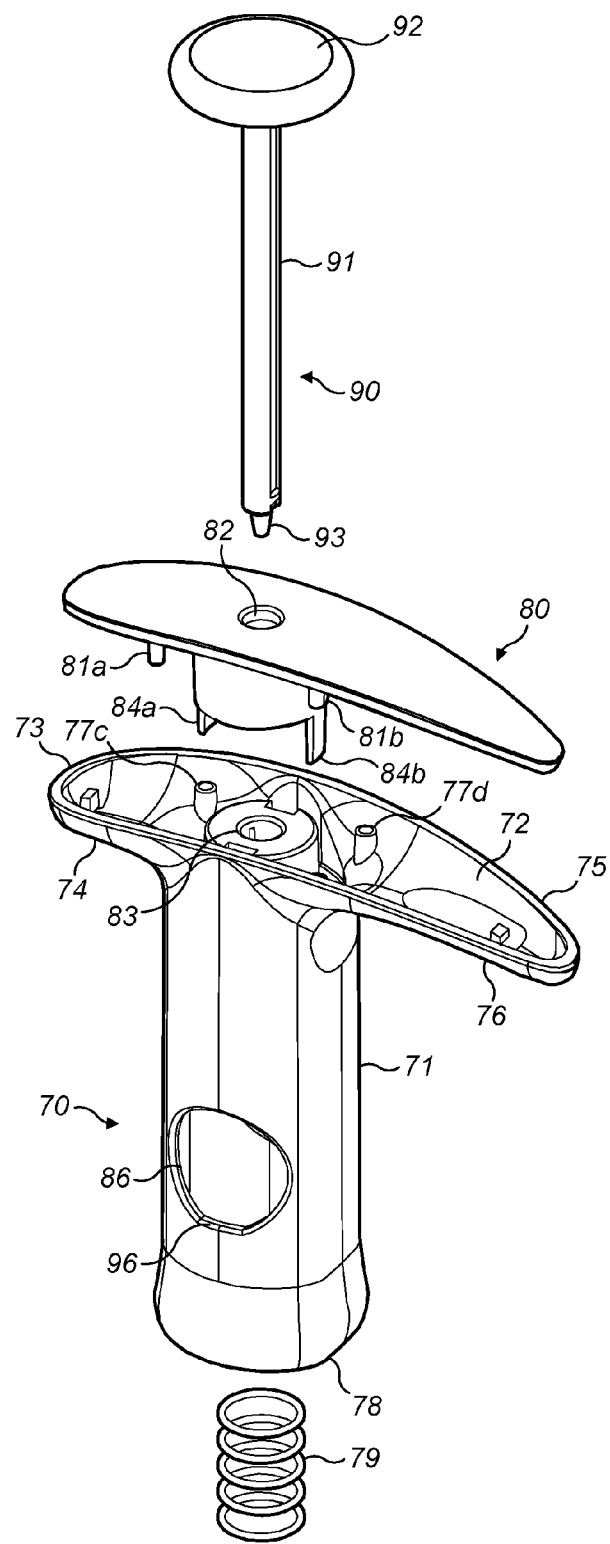
FIG. 16 is an exploded view of a manual drive unit, particularly suitable for use with the cassette unit of FIGS. 1 to 4.
Figure 25:
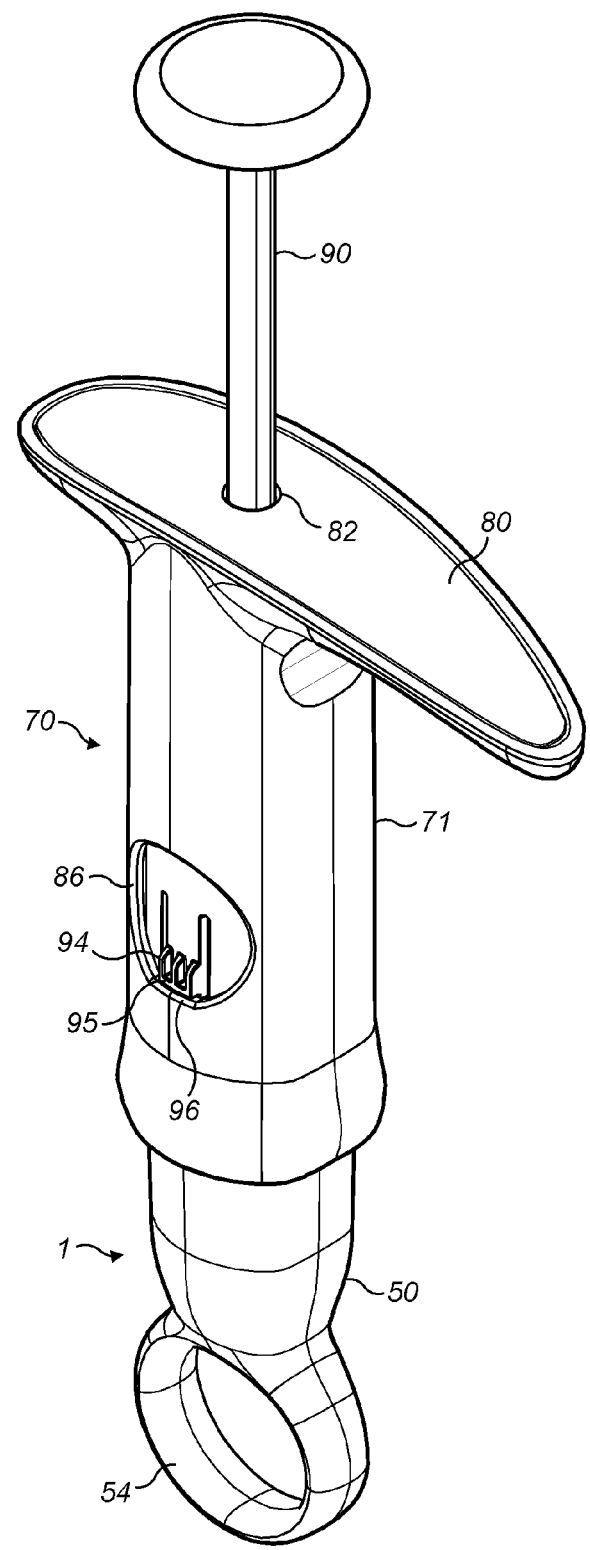
FIG. 25 is a perspective view of the manual drive unit of FIG. 16 having received in docking fashion the cassette unit of FIGS. 1 to 4 therein.

FIG. 16 shows an exploded view of a manual drive unit 70 herein for use with the cassette unit 1 as previously described. The manual drive unit 70 comprises a partly tubular form manual drive unit housing 71 that is sized and shaped at its forward end for receipt of a generally tubular form cassette unit 1. The inner walls 55 (see FIGS. 17b and 17c) of the docking cavity of the manual drive unit housing 71 may be shaped and/or provided with positioning features for positioning of the cassette unit 1 received thereby. FIG. 25 shows a view of manual drive unit 70 with the cassette unit 1 received at a docking position within the manual drive unit housing 71.

Figure 17A:
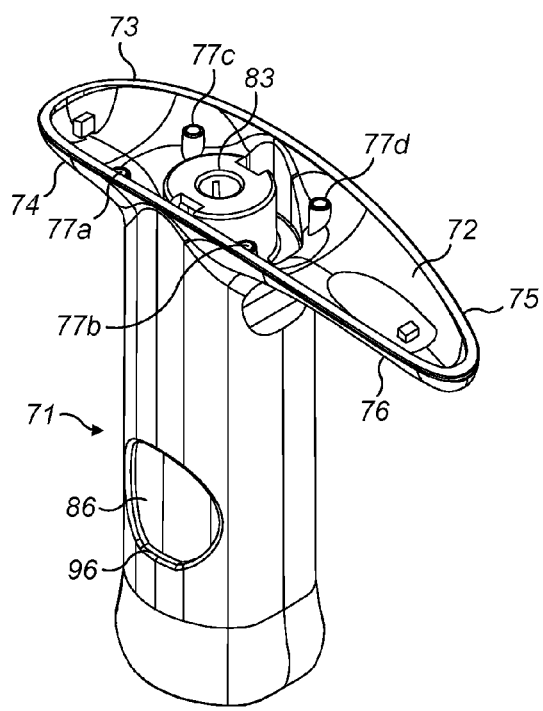
FIGS. 17a to 17c are perspective, side cross-sectional and front cross-sectional views of the housing of the manual drive unit of FIG. 16.
Figure 17B:
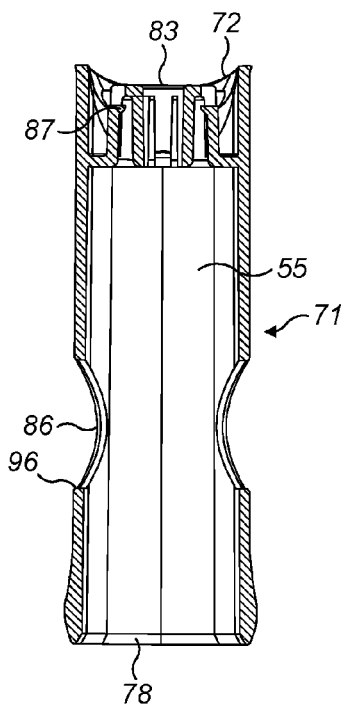
Figure 17C:
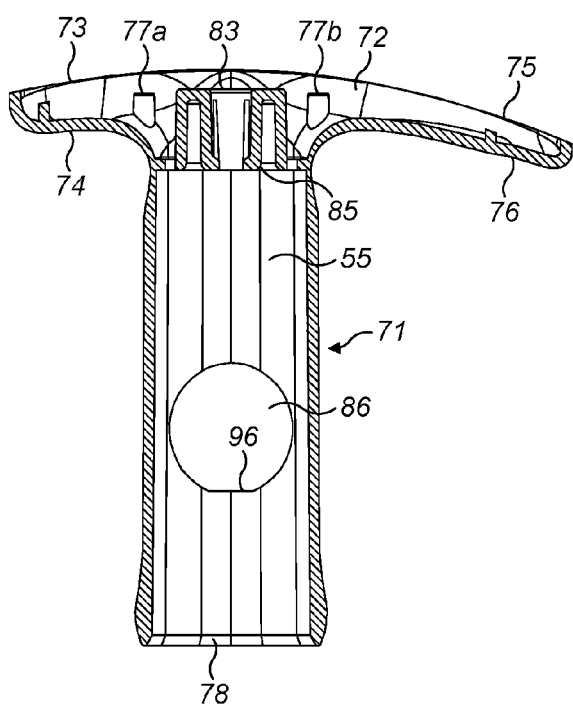

Further details of the manual drive unit housing 71 may be seen by reference to FIGS. 17a to 17c. The rearward end of manual drive unit housing 71 defines a handle 72 arranged for ease of holding by the fingers of a user. The handle 72 has a first flange 73 and a second flange 75, thereby defining a handhold. The handle 72 defines a first arc forming a bottom surface 74 of the first flange 73 contoured to correspond to a radius of a first arc (e.g. formed by a user's first finger) and a second arc forming a bottom surface 76 of the second flange 75 contoured to correspond to a radius of a second arc (e.g. formed by the user's second finger). It will be seen that the second arc 76 is shaped flatter than the first arc 74. Typically, the second flange 75 is from 1.3 to 1.7 times as long as the first flange 73. The forward end of manual drive unit housing 71 defines a needle delivery aperture 78. Spring 79, which is arranged to bias the cassette unit 1 away from the docking position towards a cassette ejected position, and the action of which will be described in more detail later, is arranged for receipt by spring retaining arms 87 of the manual drive unit housing 71.

As also shown at FIG. 25, and as will be described in more detail hereinafter, the manual drive unit housing 71 is further provided a window 86 defining a latching ledge 96 arranged for interaction with flexible locking arm features 94 on the cassette unit 1 for reversibly locking the cassette unit 1 there within at the docking position.

Figure 18A:
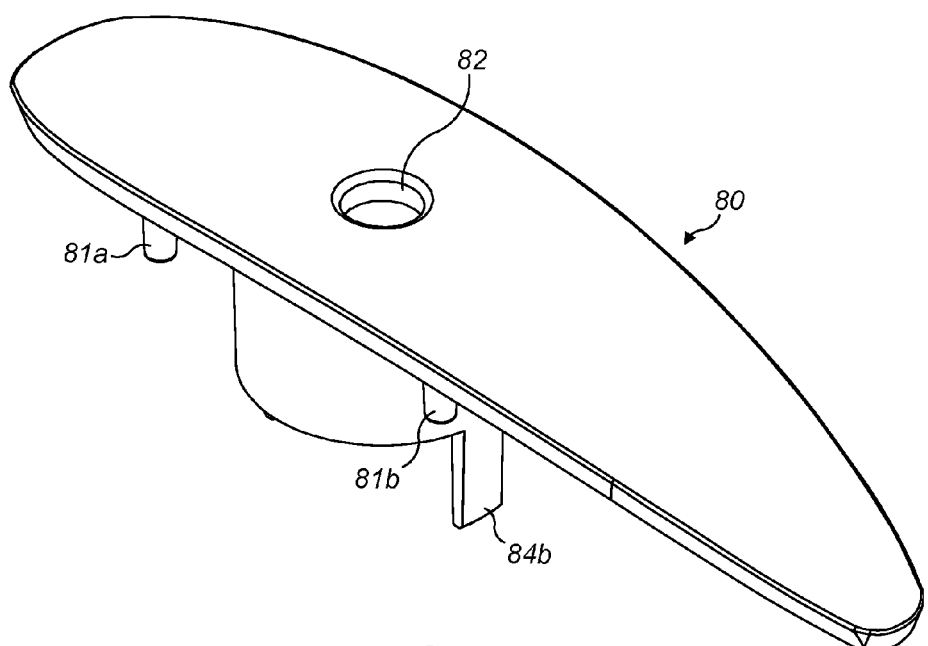
FIGS. 18a and 18b are perspective and front cross-sectional views of the cover of the manual drive unit of FIG. 16.
Figure 18B:
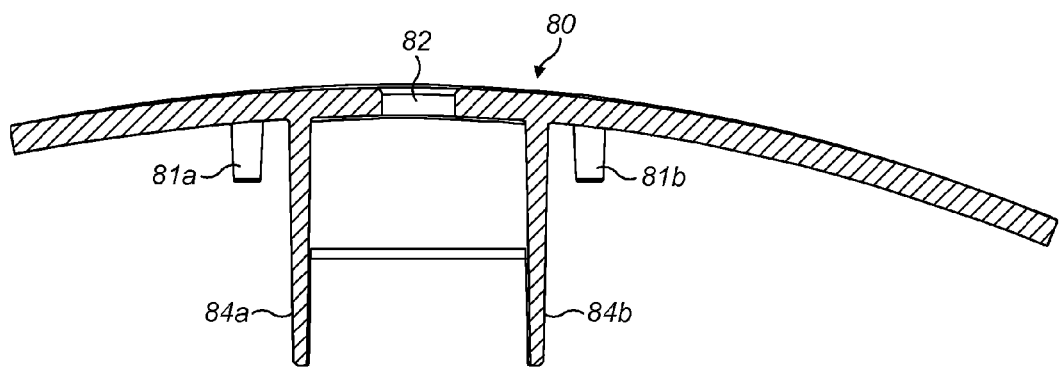

The handle 72 of the manual drive unit housing 71 defines a handle body, and said handle body is provided with a top cover 80. Further details of the top cover 80 may be seen by reference to FIGS. 18a and 18b. The top cover 80 has a plurality of first mating features in the form of pegs 81a, 81b (only two out of four visible) adapted to mate with a set of corresponding second mating features in the form of peg-holes 77a-d (four visible only at FIG. 17a) formed on the handle body. 17. The top cover 80 includes an aperture 82 for receiving the drive rod 90. Similarly, the handle body of the manual drive unit housing 73 includes an aperture 83 for receiving the drive rod 90. The top cover 80 is also provided with a cap lock release feature defining forwardly protruding arms 84a, 84b, which are arranged for pushing interaction with shuttle lock control 32 of the cassette unit 1, as will be described in more detail hereinafter.

The manual drive unit housing 71 is provided with a manually operable drive transfer element in the form of a drive rod 90 further details of which may be seen by reference to FIGS. 19a to 19c. The drive rod 90 has a drive shaft 91 having a drive head 92 with underside 99 that is shaped for ease of interaction with the user's fingers and a drive tip 93. As will be described in more detail hereinafter, within the manual drive unit 70, the drive rod 90 is drive is axially movable relative to the manual drive unit housing 71 for transferring axial drive to the plunger 18 of the syringe 10 for moving the plunger 18 into the barrel 16 of the syringe 10 to eject at least part of a volume of liquid drug formulation. As will be described in more detail hereinafter, the drive shaft 91 is provided adjacent to the drive tip 93 with an arrowhead feature 95 defining a forward retaining ledge 97, which is arranged for retaining interaction with drive rod retaining arms 85 (see FIG. 17c) of the manual drive unit housing 71 such as to retain the drive rod 90 in movable relationship to the manual drive unit housing 71. A rearward-retaining ledge 98 is also defined.

Figure 20:
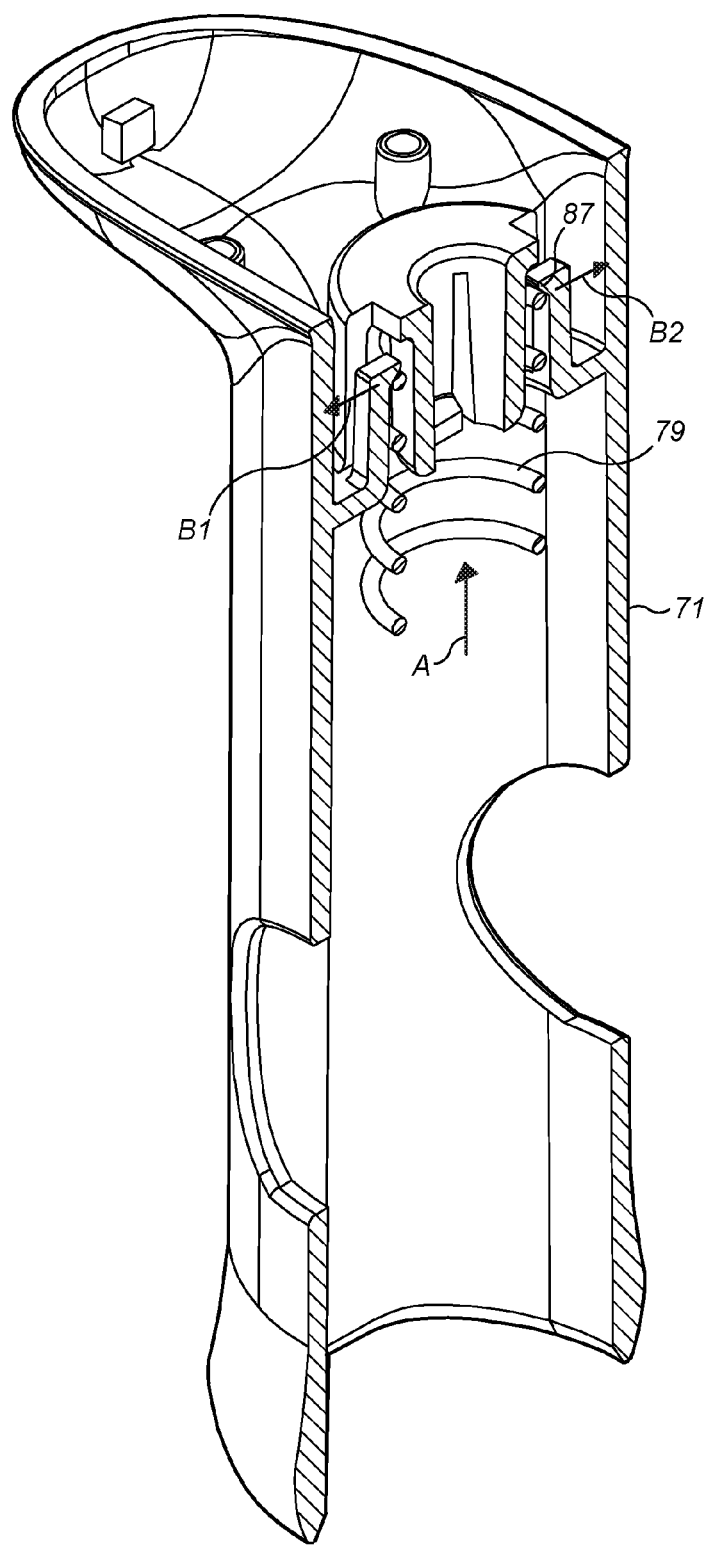
FIG. 20 is a side cross-sectional view of assembly of the spring into the housing of the manual drive unit of FIG. 16.
Figure 21:
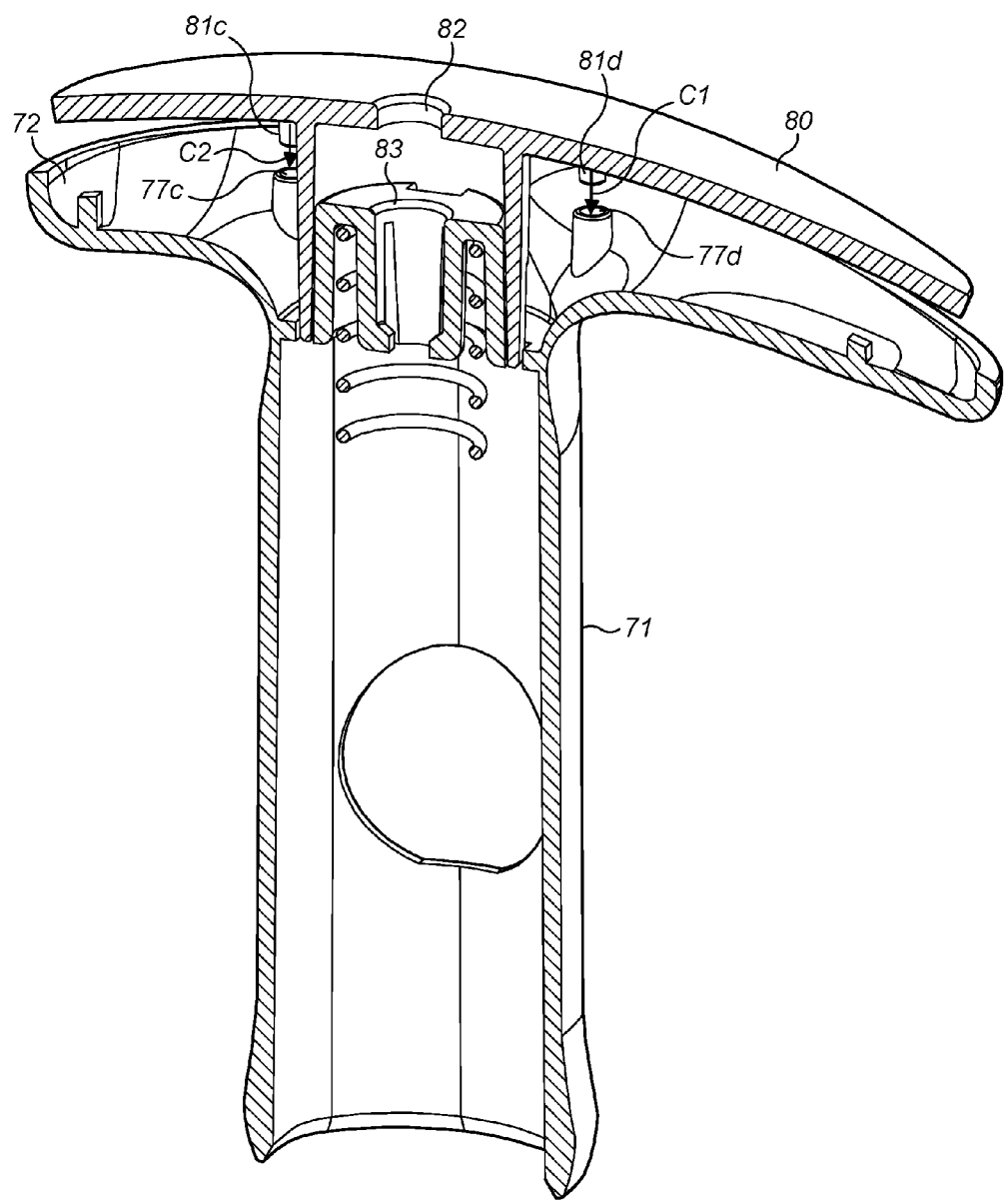
FIG. 21 is a front cross-sectional view of assembly of the cover onto the housing of the manual drive unit of FIG. 16.
Figure 22:
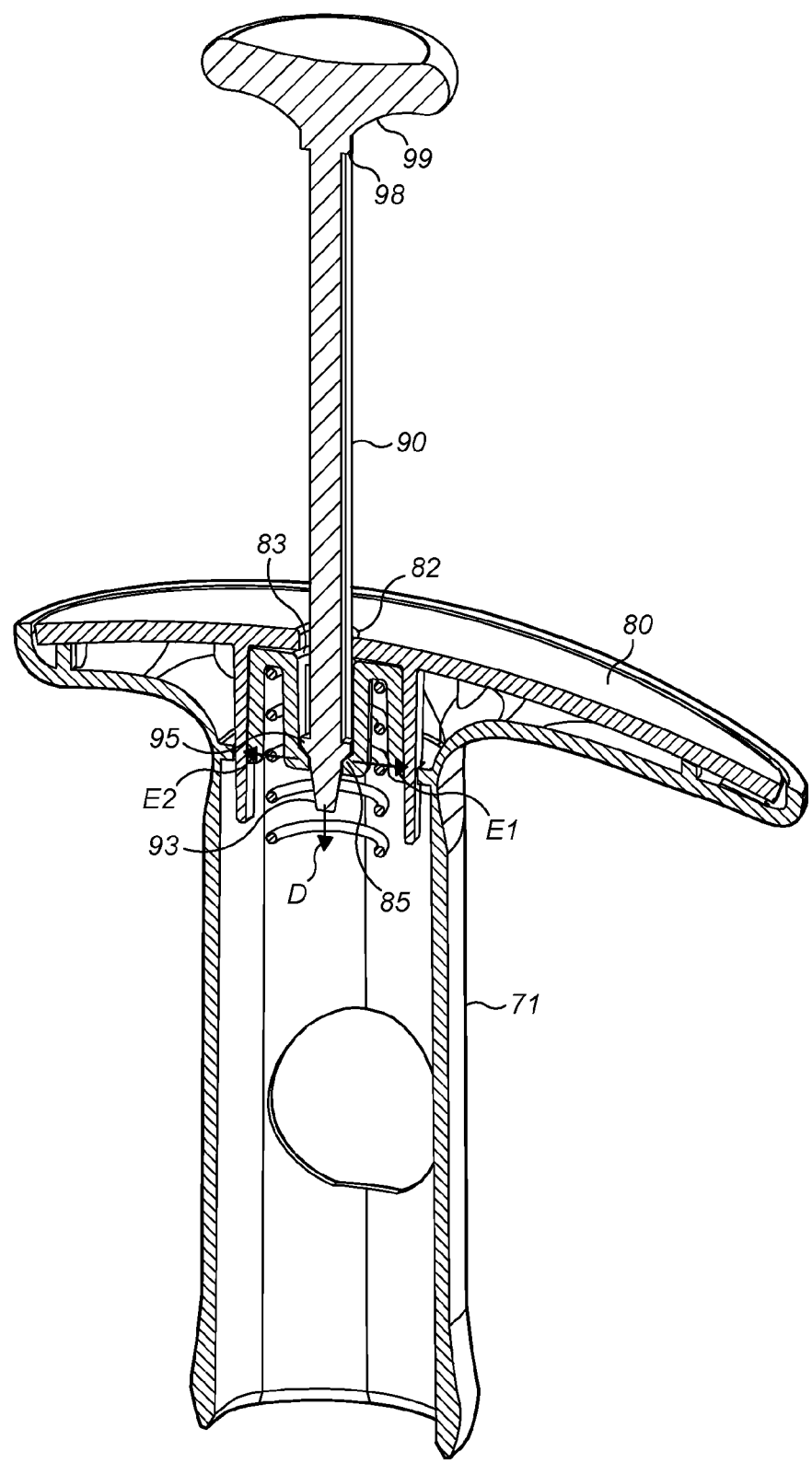
FIG. 22 is a front cross-sectional view of assembly of the drive rod into the housing of the manual drive unit of FIG. 16.

FIGS. 20 to 22 show sequential steps in the assembly of the manual drive unit 70 herein, which are typically undertaken in a manufacturing environment. For succinctness, only the parts relevant to the particular assembly operation are labelled on each Figure.

At FIG. 20, spring 79 is inserted into the manual drive unit housing 71 through the needle delivery aperture 78 thereof. As shown by arrow A, the head (i.e. most rearward located part) of the spring 79 is pushed past spring retaining arms 87 of the manual drive unit housing 71, which flex outwards (as shown by arrows B1, B2) to receive the head of the spring 79 and then flex backwards such as to retain the spring 79 in place. The action of the spring 79 within the manual drive unit 70 is to bias an inserted cassette unit 1 away from the docking position and towards a cassette ejected position (e.g. see FIGS. 27 and 28a).

At FIG. 21, top cover 80 is mated with handle 72 part of the manual drive unit housing 71. As shown by arrows C1, C2, first mating features in the form of pegs 81c, 81d (only two out of four visible at FIG. 21) are brought into mating relationship with a set of corresponding second mating features in the form of peg-holes 77c, 77d (only two out of four visible at FIG. 21) formed on the handle body. It will be noted that aperture 82 of the top cover 80 and aperture 83 of the manual drive unit housing 73 are in registration.

At FIG. 22, drive rod 90 is introduced into the manual drive unit housing by forward insertion through aperture 82 of the top cover 80 and aperture 83 of the manual drive unit housing 73. As shown by arrow D, drive tip 93 with adjacent arrowhead feature 95 of the drive rod 90 is pushed past drive rod retaining arms 85 (as shown by arrows E1, E2) of the manual drive unit housing 71 such as to retain the drive rod 90 in axial movable relationship to the manual drive unit housing 71.

Figure 23:
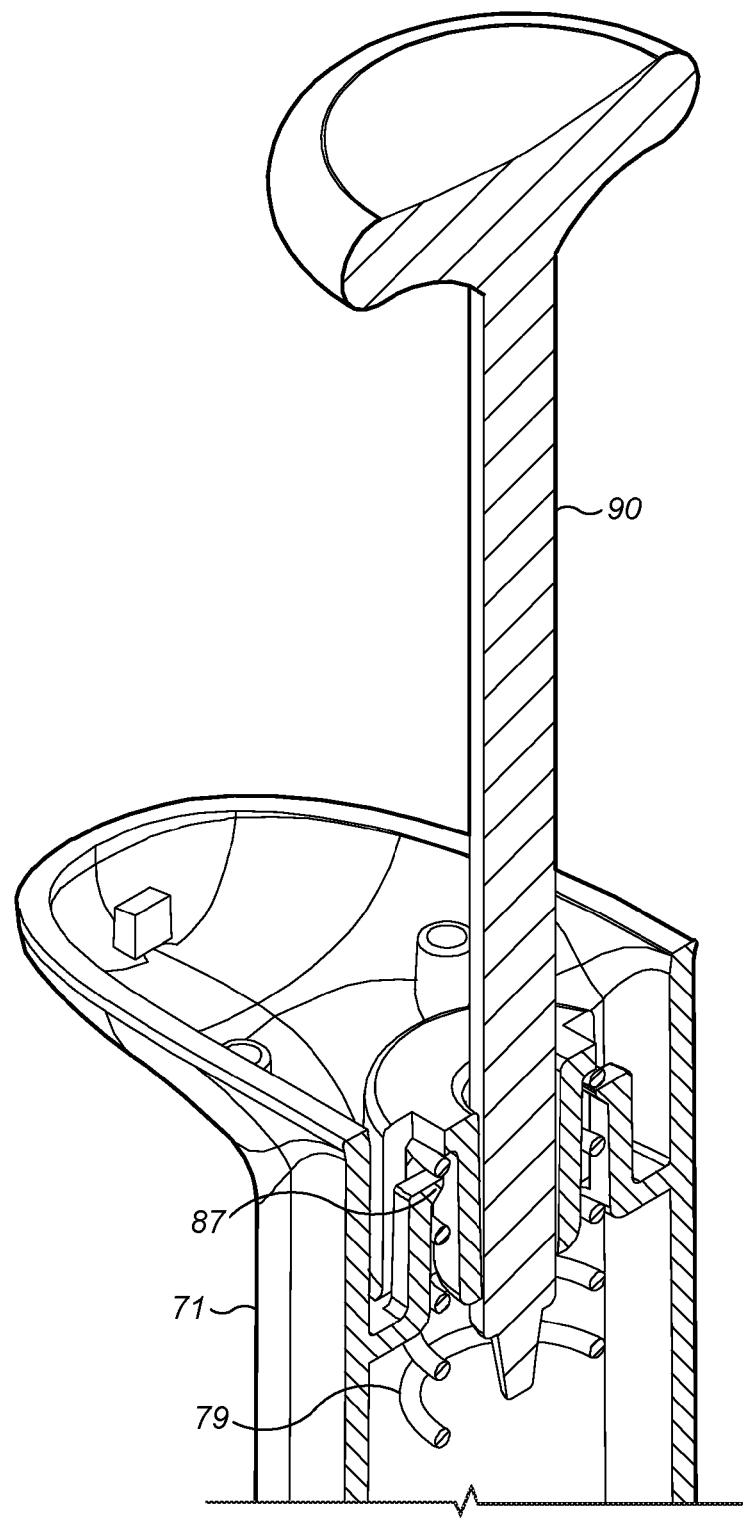
FIG. 23 is a side cross-sectional view of a detail of the relationship between the spring and housing of the manual drive unit of FIG. 16.
Figure 24:
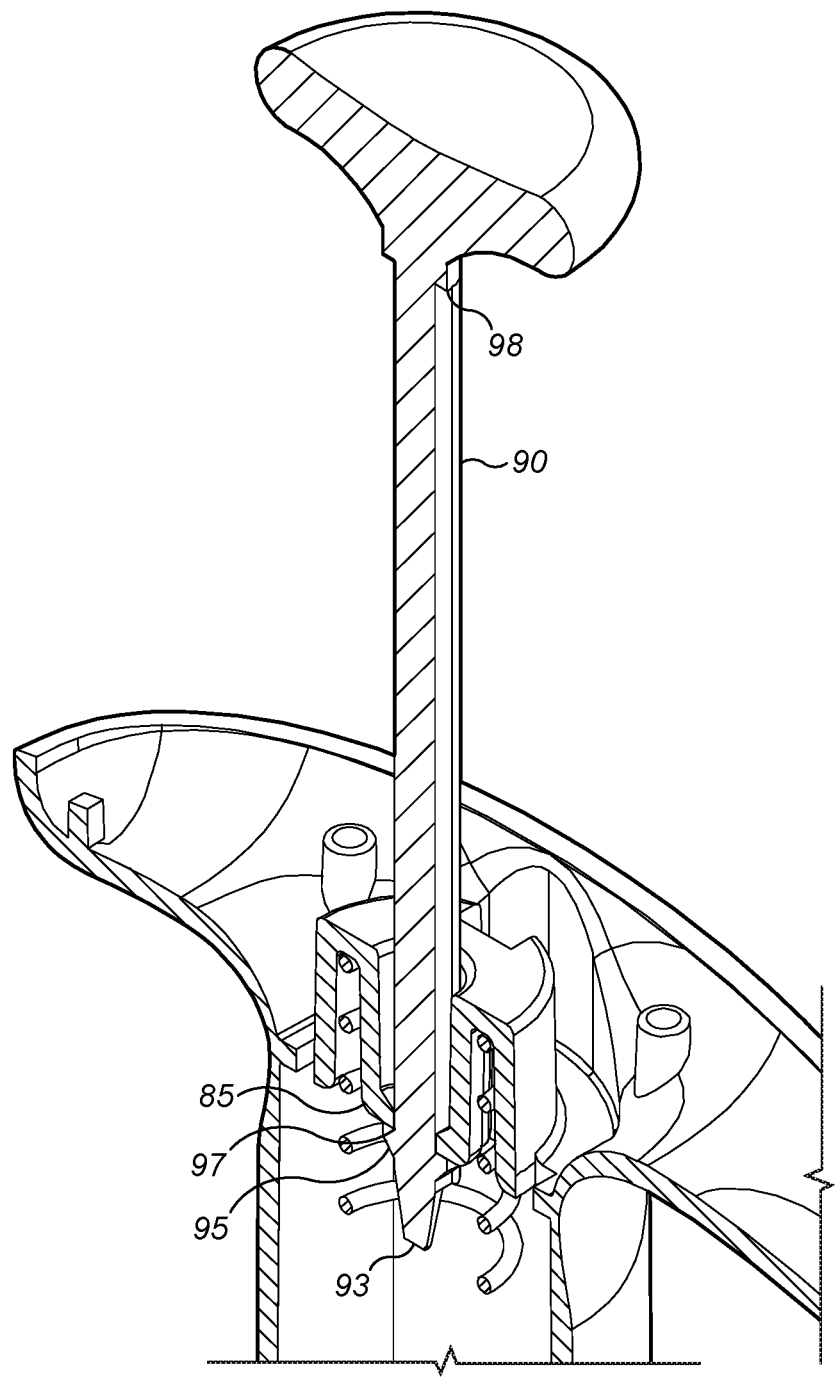
FIG. 24 is a front cross-sectional view of a detail of the relationship between the drive rod and housing of the manual drive unit of FIG. 16.

FIGS. 23 and 24 show details of the relationship between the manual drive unit housing 71, spring 79 and drive rod 90 in the assembled manual drive unit 70. For the purposes of illustration only top cover 80 is not shown in FIGS. 23 and 24.

At FIG. 23, the relationship between spring 79 and manual drive unit housing 71 is most clearly shown. Spring retaining arms 87 of the manual drive unit housing 71 have received the head of the spring 79 such as to retain the spring 79 in place within the housing 71. In other embodiments, spring 79 is absent.

At FIG. 24, the relationship between drive rod 90 and manual drive unit housing 71 is most clearly shown. Drive rod retaining arms 85 of the manual drive unit housing 71 have received the drive shaft 91 of the drive rod 90, whereby forward retaining ledge 97 of the drive rod abuts the underside of drive rod retaining arms 85 of the manual drive unit housing 71 such as to retain the drive rod 90 in axial movable relationship to the manual drive unit housing 71. It will also be appreciated that the retaining interaction between the forward retaining ledge 97 of the drive rod 90 and the underside of drive rod retaining arms 85 of the manual drive unit housing 71 effectively acts to limit the possible rearward extent of axial travel of the drive rod 90 relative to the manual drive unit housing 71. In addition, the interaction between the underside 99 of the drive rod 90 and the aperture 82 of the top cover (see also FIG. 22) effectively acts to limit the possible forwards extent of axial travel of the drive rod 90 relative to the manual drive unit housing 71. Thus, the drive rod 90 is effectively retained within the manual drive unit housing 71 and is axial movable there within, but only within defined limits to rearward and forward axial travel, which are generally selected to correspond to an injection stroke.

FIG. 25 shows the manual drive unit 70 having received a representative cassette unit 1 at the docking position, wherein ring pull 54 of the removable cap 50 protrudes from the manual drive unit housing 71. As so-received within the manual drive unit 70, the cassette unit 1 is selectively locked therein by the interaction of engaging tips 95 of locking arms 94 with the latching ledge 96 of window 86 of the manual drive unit housing 71. The locking arms 94 are arranged to flex into the cassette unit locking position (i.e. with latching engagement of engaging tips 95 of locking arms 94 with the latching ledge 96 of window 86) on insertion of the cassette unit 1 into the manual drive unit 70 at the docking position.

Figure 26:
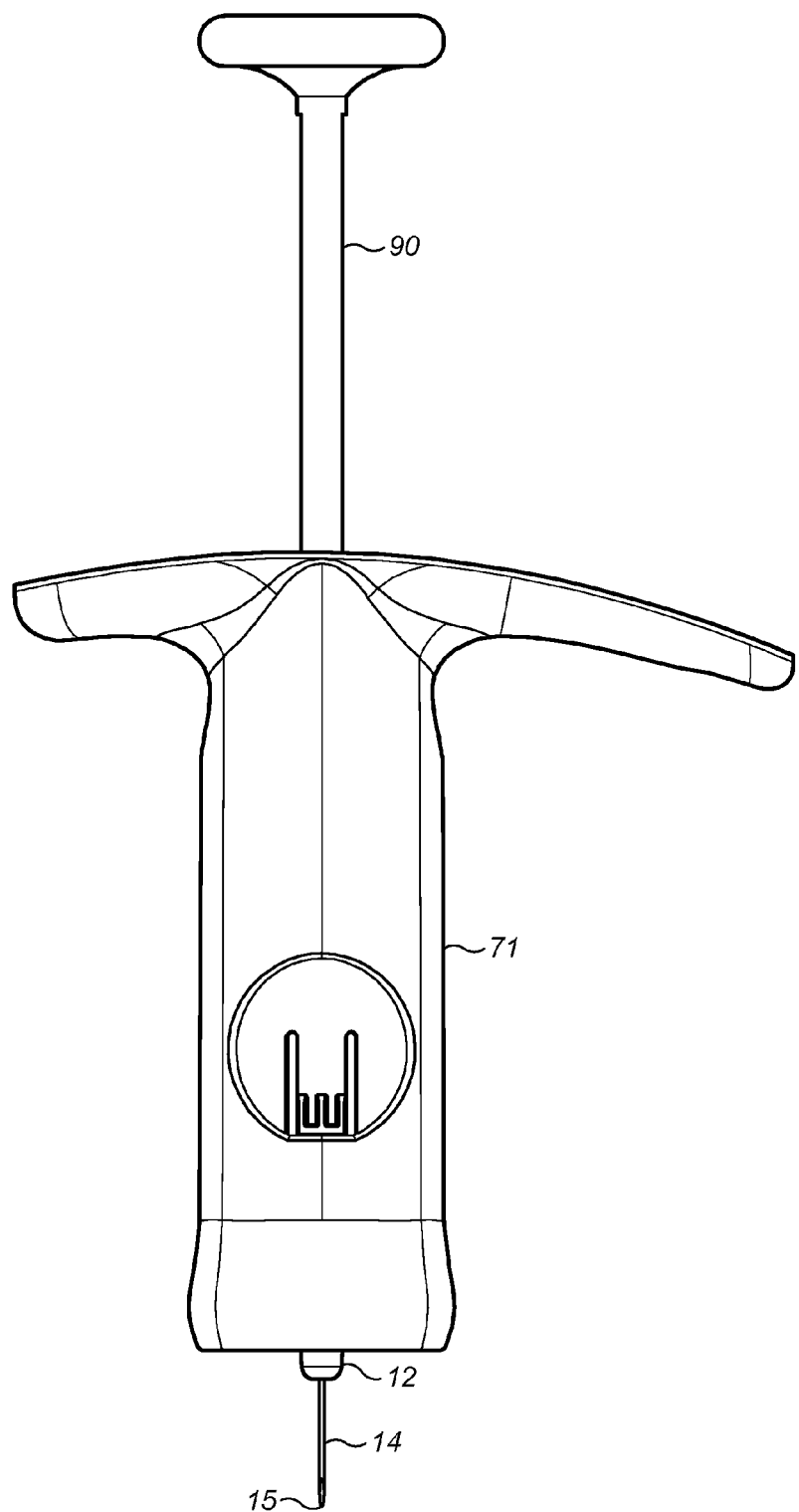
FIG. 26 is a perspective view of the manual drive unit of FIG. 16 having received the cassette unit of FIGS. 1 to 4 therein, as shown with the cap of the cassette unit removed and thus, in the 'ready to inject' position.

During use, as shown at FIG. 26, the cap 50 is removed to expose the needle 14 and needle tip 15 of the syringe 10.

Figure 27:
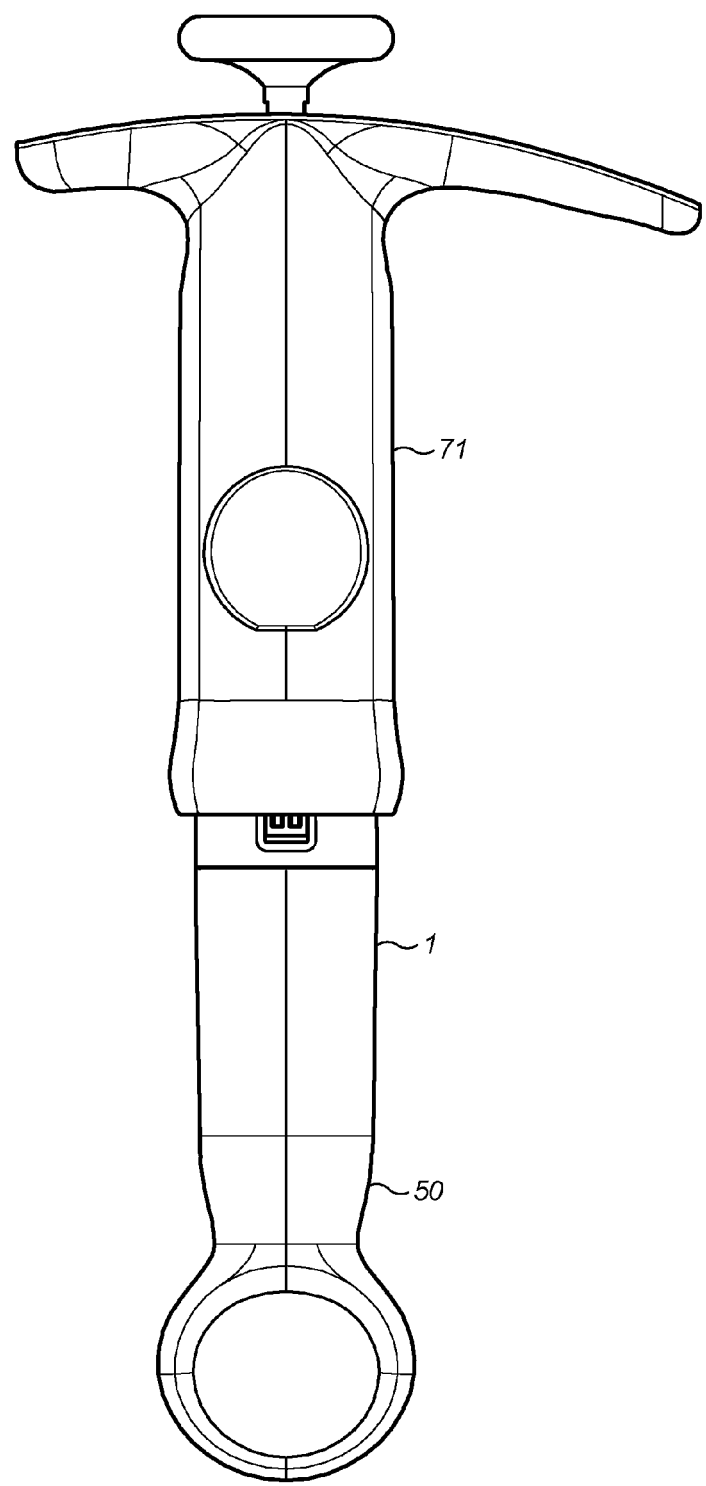
FIG. 27 is a perspective view of the manual drive unit of FIG. 16 and cassette unit of FIGS. 1 to 4, as shown in the 'cassette-ejected' position.

After use, the user manually pushes/flexes locking arms 94 inwards, thereby allowing the engaging tips 95 thereof to move out of latching engagement with latching ledge 96 of window 86. Under the action of spring 79, the cassette unit 1 is then ejected from the manual drive unit housing 79 to the cassette unit 1 ejected position as shown at FIG. 27.

Further use aspects of the injector herein may now be appreciated by reference to FIGS. 28a to 28f and to the following description of a typical use operation: These show and describe sequential use steps of a first manual drive unit 70 as already described by reference to FIGS. 16 to 24 as particularly used in conjunction with a cassette unit 1 essentially in accord with that already described by reference to FIGS. 1 to 15. For clarity, only those aspects of FIGS. 28a to 28f, which are most relevant to the use operation being described, are identified by labelling.

Figure 28A:
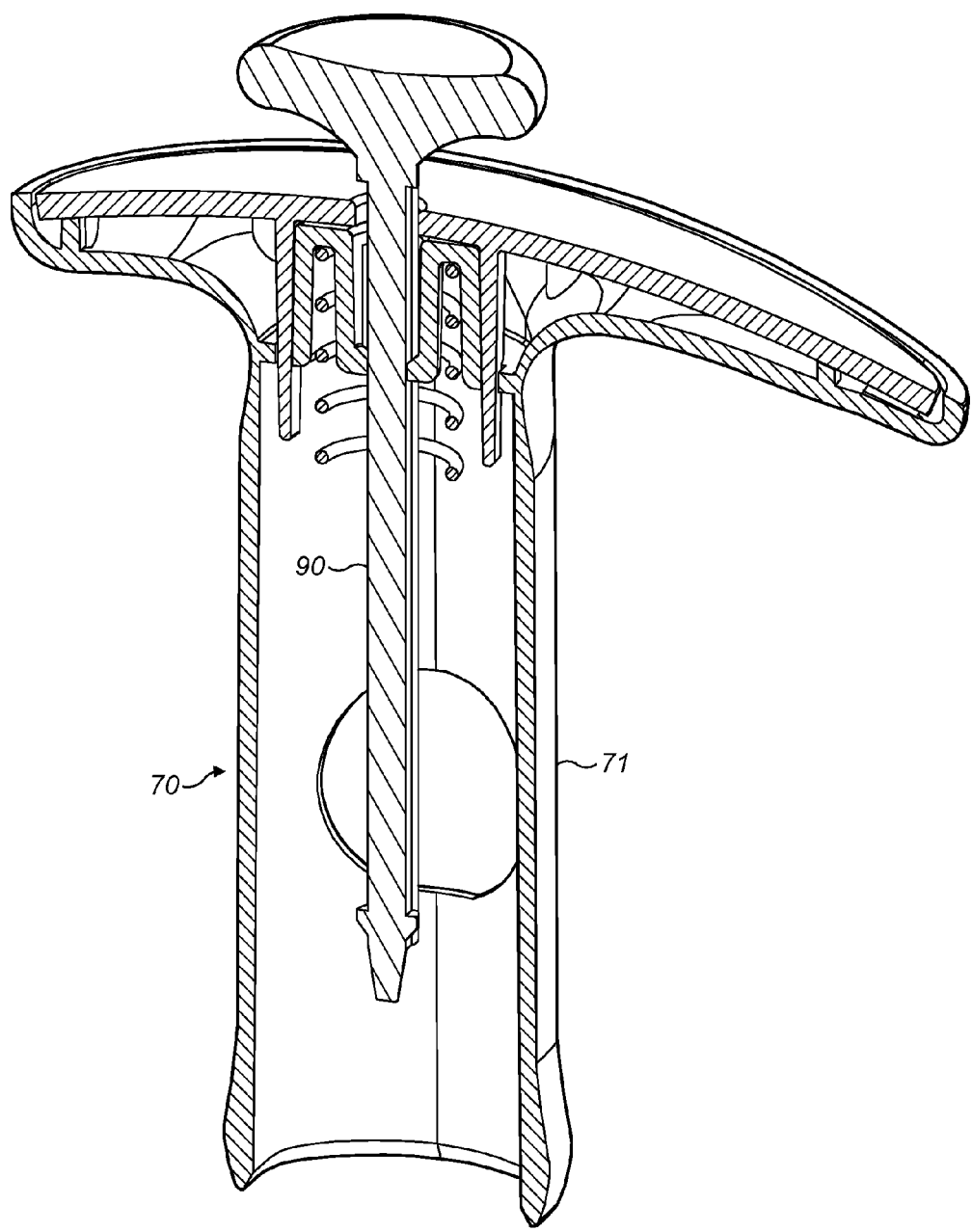
FIGS. 28a to 28f show front cross-sectional views of sequential stages of use for injection of the manual drive unit of FIG. 16 with the cassette unit of FIGS. 1 to 4.

The manual drive unit 70 and cassette unit 1 are typically supplied as separate entities for assembly by the user into a use configuration. FIG. 28a shows a manual drive unit 70 with the drive rod 90 at its forward most extent within the manual drive unit housing 71 and ready to receive a cassette unit 1.

Figure 28B:
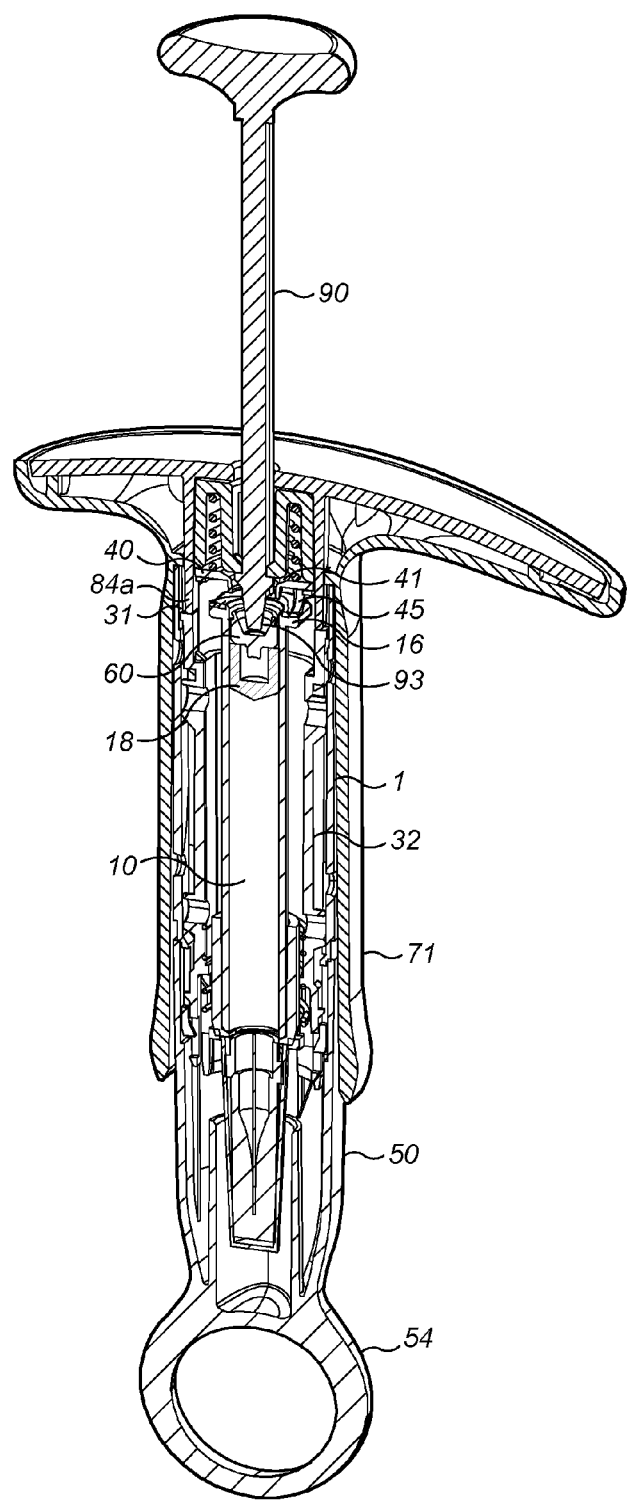

In a first stage of a typical use operation, as shown at FIG. 28*b*, the user inserts cassette unit 1 comprising syringe 10 and having removable cap 50 to the docking position within the manual drive unit housing 71 of the manual drive unit 70. This corresponds to that position shown at FIG. 25, and in which, as previously described in relation to that Figure, the cassette unit 1 is selectively locked therein by the interaction of engaging tips 95 of locking arms 94 with the latching ledge 96 of window 86 of the manual drive unit housing 71.

In the docking position, drive tip 93 of drive rod 90 is received within the drive transfer element-receiving opening 41 of the cassette unit end-cap 40. End-cap spring 45 defines a sprung biasing relationship between the cassette unit end-cap 40 and the flange 16 of the syringe 10, thereby urging the syringe 10 forwards in relation to the cassette unit end cap 40.

Plunger slaving part 60 is in releasable engagement with the cassette unit end-cap 40. As will be described hereinafter, in use, the plunger slaving part 60 is subsequently released from the cassette unit end-cap 40 in response to forward axial drive provided by the drive rod 90 to a rear drive-receiving face thereof.

The general function of the tapering drive tip 93 of the drive rod 90 is to give rise to a point load instead of a face load. The slaving part 60 is made of a hard material, thus acting to reduce friction and torsion loads on the system. The slaving part 60 is arranged to function such that when a load is applied to its top face the load is evenly transmitted directly into the syringe plunger 18. In embodiments, the slaving part 60 is brightly coloured and performs a second function of providing an easy-to-identify visual indicator of the position of the plunger 18 within the syringe 10 so that the patient can visually confirm the drug had been fully injected.

As also shown at FIG. 28*b*, in the docking position, the shuttle lock control 32 is in the second 'cassette unlocked' position (having been pushed relatively forward by the interaction of protruding arms 31 with defining forwardly protruding arms 84*a* (only one labelled) of the cap lock release feature of the top cover 80 and thus, the removable cap 50 is in the cap unlocked position. As shown more clearly at FIGS. 9*b*, 10*b* and 11*b*, in the 'cap unlocked' position the inner face of the locking arm 26 of the cassette unit housing 20 is no longer blocked. As a result, inwards movement of the locking arm 26 is no longer prevented and disengagement of the tip 29 of the locking arm 26 from socket through-hole 52 of the removable cap 50 is achievable by suitable inwards pushing action on the tip 29/locking arm 26. Such inward pushing action on the locking arm 26 is achievable by pulling the cap 50 away from the cassette unit 1, which results in the angled tip 29 interacting with the wall edges of the socket through-hole 52 to push the locking arm 26 inwards.

Figure 28C:
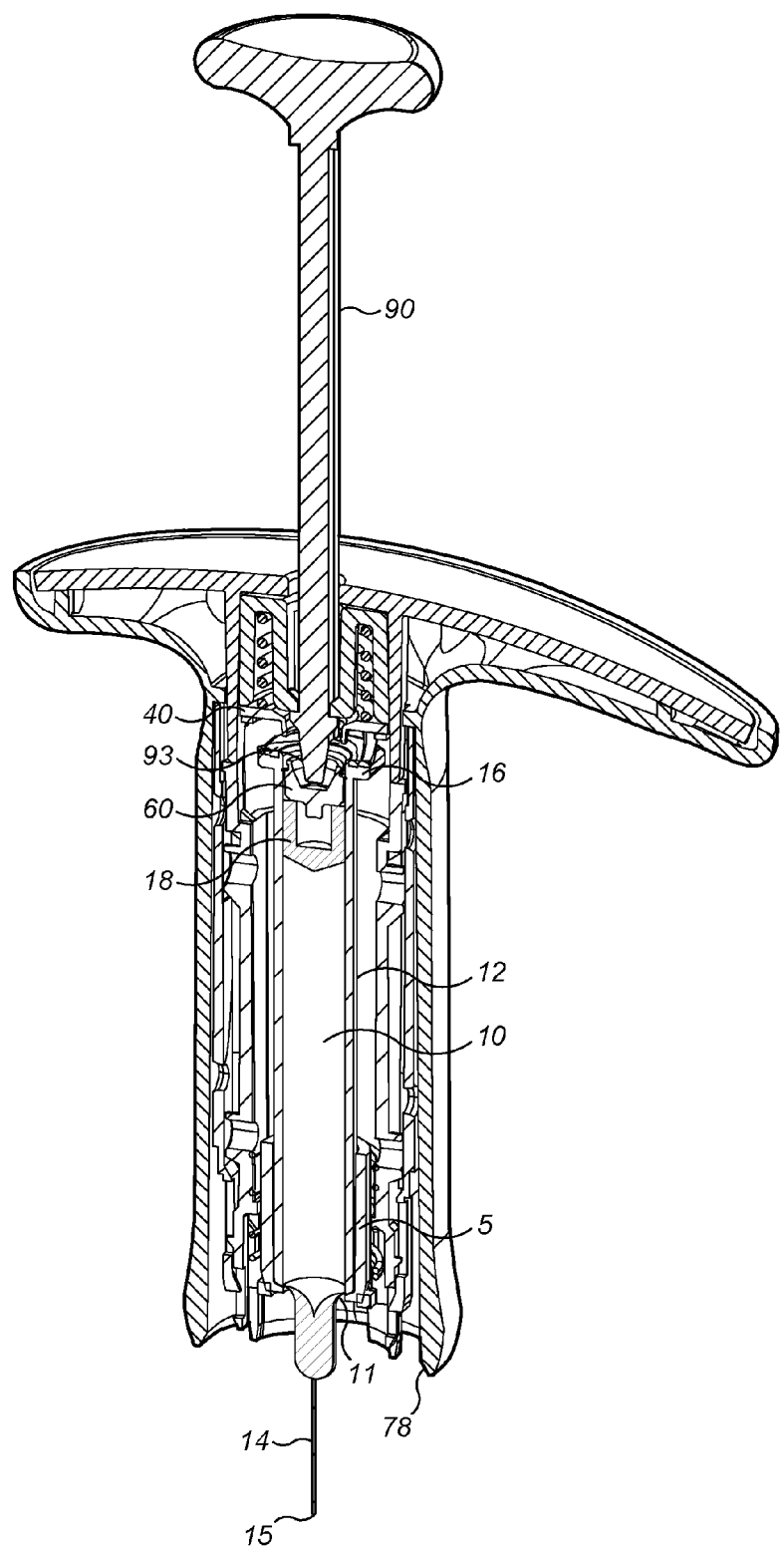

In a second stage of a typical use operation, as shown at FIGS. 28*c* and 26, the user has removed the cap 50 together with needle sheath 17 and rigid needle shield 19. The needle 14 with tip 15 of the syringe 10 is now uncovered and protrudes from the needle delivery aperture 78 of the manual drive unit housing 71. This corresponds to the 'ready to inject' position.

Once the injector is at the 'ready to inject' position of FIGS. 28*c* and 26, ejection of drug from the syringe barrel 12 can commence. Such ejection is in response to manual driving forwards of drive rod 90 by the user. Typical manual drive actions are shown by reference to FIGS. 29 and 30, which both show the drive rod 90 in the fully driven in position.

Figure 29:
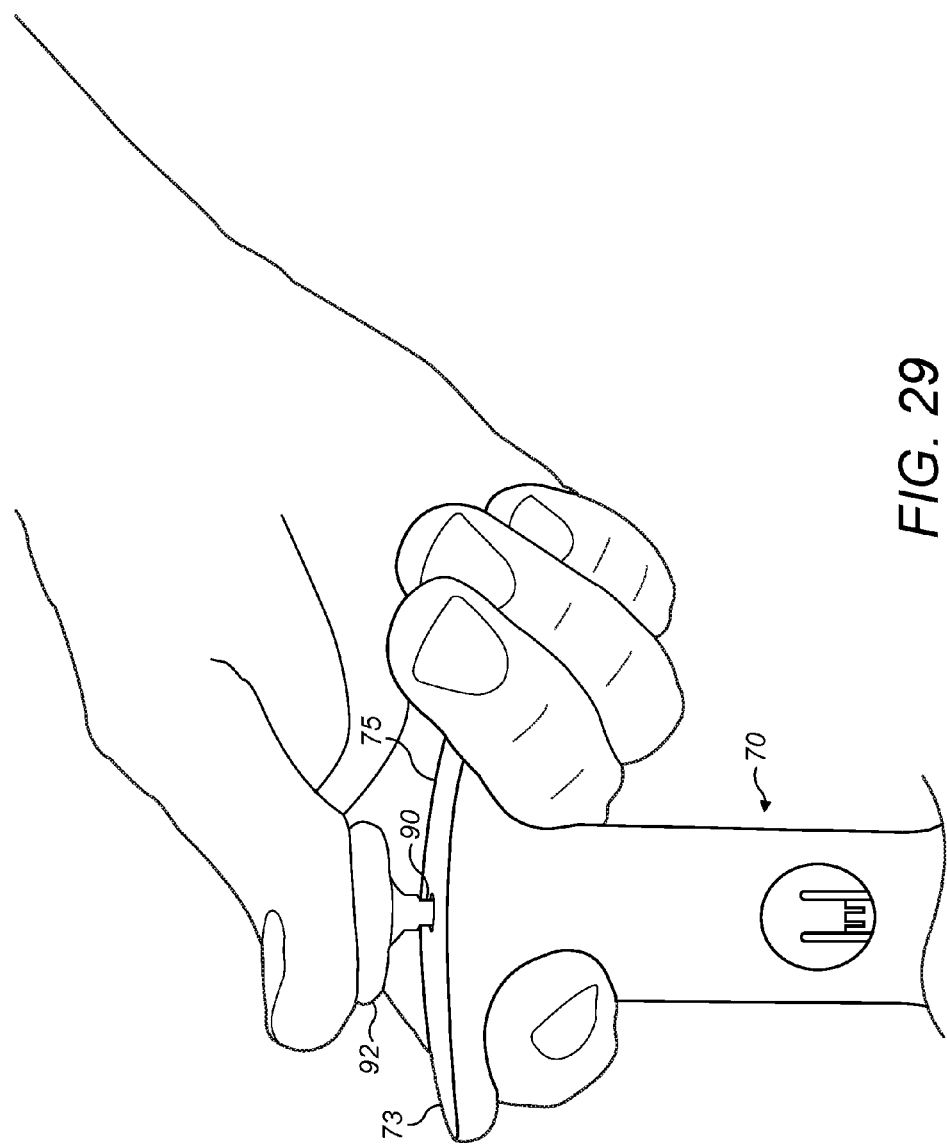
FIG. 29 shows the manual drive unit of FIG. 16 in a first use configuration within the hand of a user.
Figure 30:
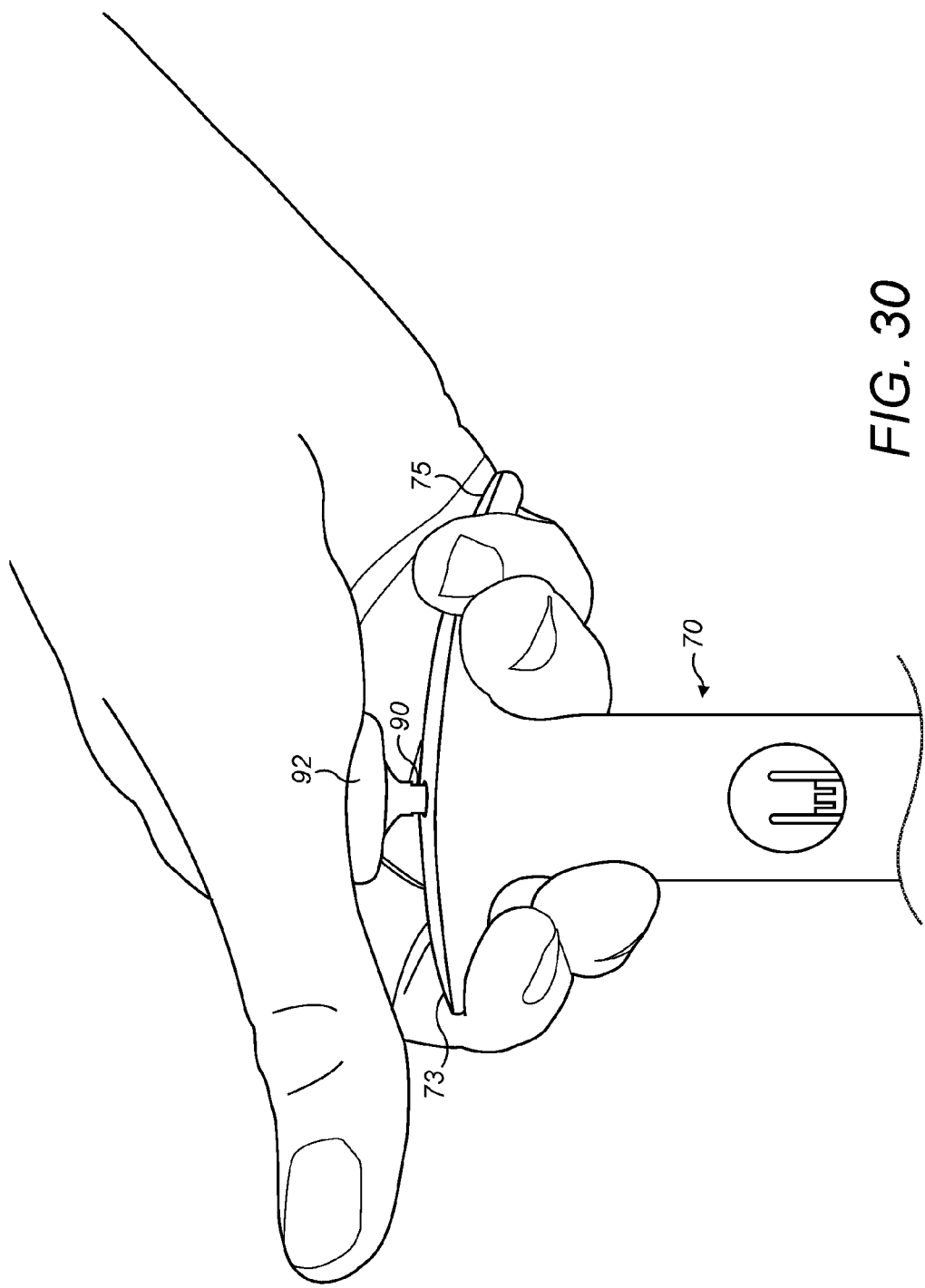
FIG. 30 shows the manual drive unit of FIG. 16 in a second use configuration within the hand of a user.

FIGS. 29 and 30 also depict the positioning of the drive rod 90 with respect to the handhold 73, 75. As shown in FIG. 29, the handhold 73, 75 is shaped to allow the patient's thumb to comfortably sit on the drive head 92 of the drive rod 90. The drive head 92 is typically formed of a plastic material, and may in embodiments be provided with a rubber over mould. The drive head 92 is shaped to receive the surface of the patient's thumb or other preferred finger(s) or parts of the patient's hand. FIG. 29 shows the base of the patient's thumb resting on the drive head 92. In some embodiments, the user prefers to place his palm on the drive head 92 for manipulating the drive rod. FIG. 30 shows the patient using the base of his palm for pushing the drive rod 90 for ejecting the contents of the syringe. The shape of the drive head 92 forms a depression for receiving the patient's finger or other parts of the patient's hand during the use of the manual drive unit 70, which aids in preventing the patient's finger or hand from slipping from the top surface of the drive head 92, thereby making the injection process safer.

As a result of manual driving movement of the drive rod 90, drive tip 93 is now in driving contact with rear drive-receiving end of slaving part 60. The resulting forward advancement thereof results in release of the plunger slaving part 60 from the end-cap 40 and then in forward sliding movement of that slaving part 60 within the syringe barrel 12, which in turn results in plunging movement of the plunger 18 within the barrel 12 of the syringe 10 to expel the drug formulation contents through the tip 15 of the needle 14 and into the injection site (e.g. skin of the user). The slaving part 60 functions such that when a driving load is applied to its rear drive-receiving face 63, 66 by drive tip 93 of drive rod 90 the load is evenly transmitted directly into the syringe plunger 18.

To reduce the risk of the syringe 10 fracturing under the loads associated with injecting the drug, it is important for a majority of the load path to travel through the forward shoulder 11 of the syringe barrel 12 and lesser load to pass through the flange 16 at the rear end thereof. It may therefore be seen at FIG. 28*c* that forward shoulder 11 of the syringe 10 is surrounded by shoulder support feature 5 (see also FIGS. 5*a* to 5*c*).

Figure 28D:
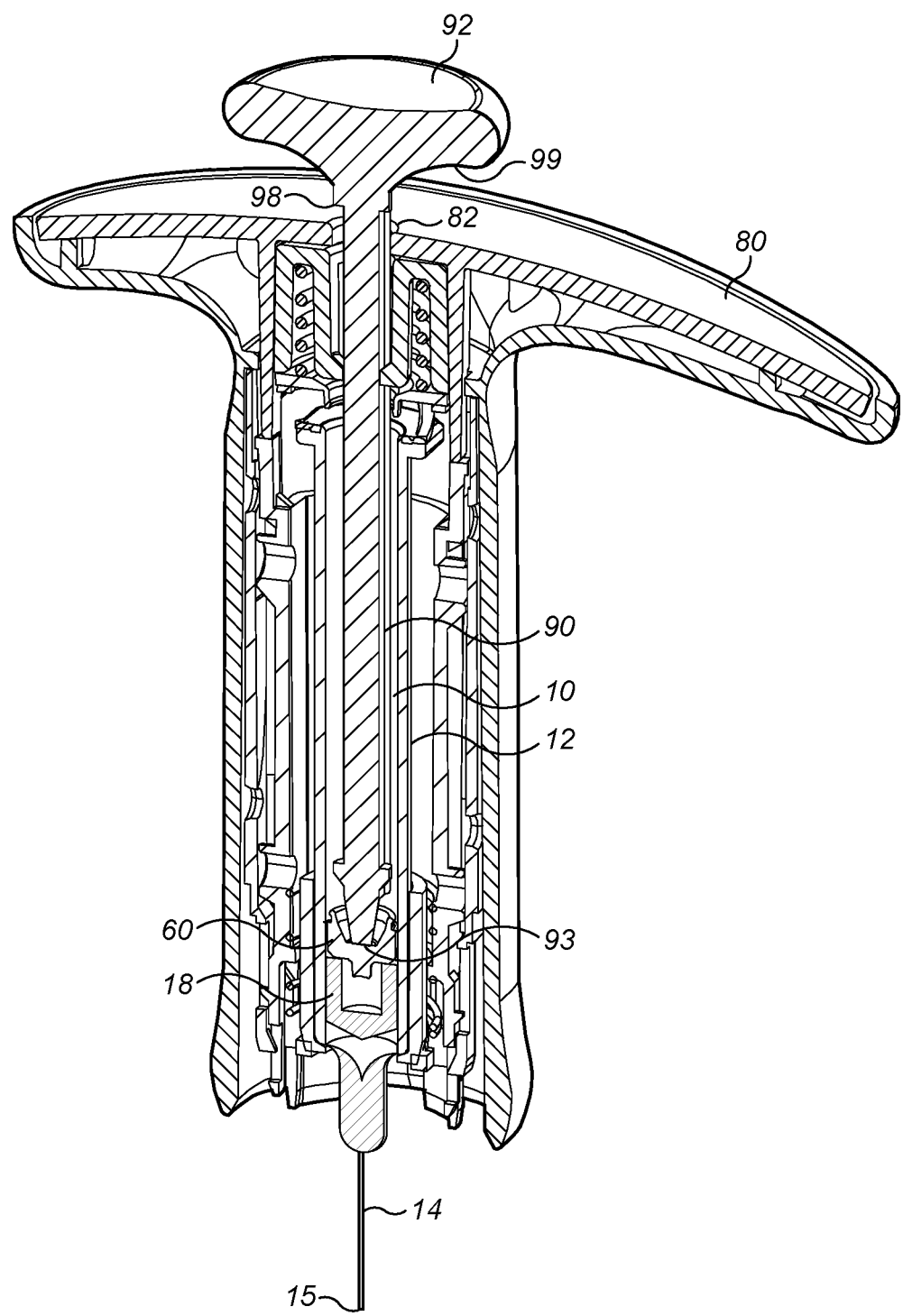

In a third stage of a typical use operation, as shown at FIG. 28*d*, post-completion of the injection, the drive rod 90 has been driven to its furthest forwards extent (governed by the limiting relationship between underside 99 of drive head 92 of the drive rod 90 and the aperture 82 of the top cover 80). The plunger 18 has been driven forwards within the barrel 12 of the syringe 10 to expel the drug formulation contents through the tip 15 of the needle 14 and into the injection site (e.g. skin of the user). The next step is for the user to replace the cap 50.

Figure 28E:
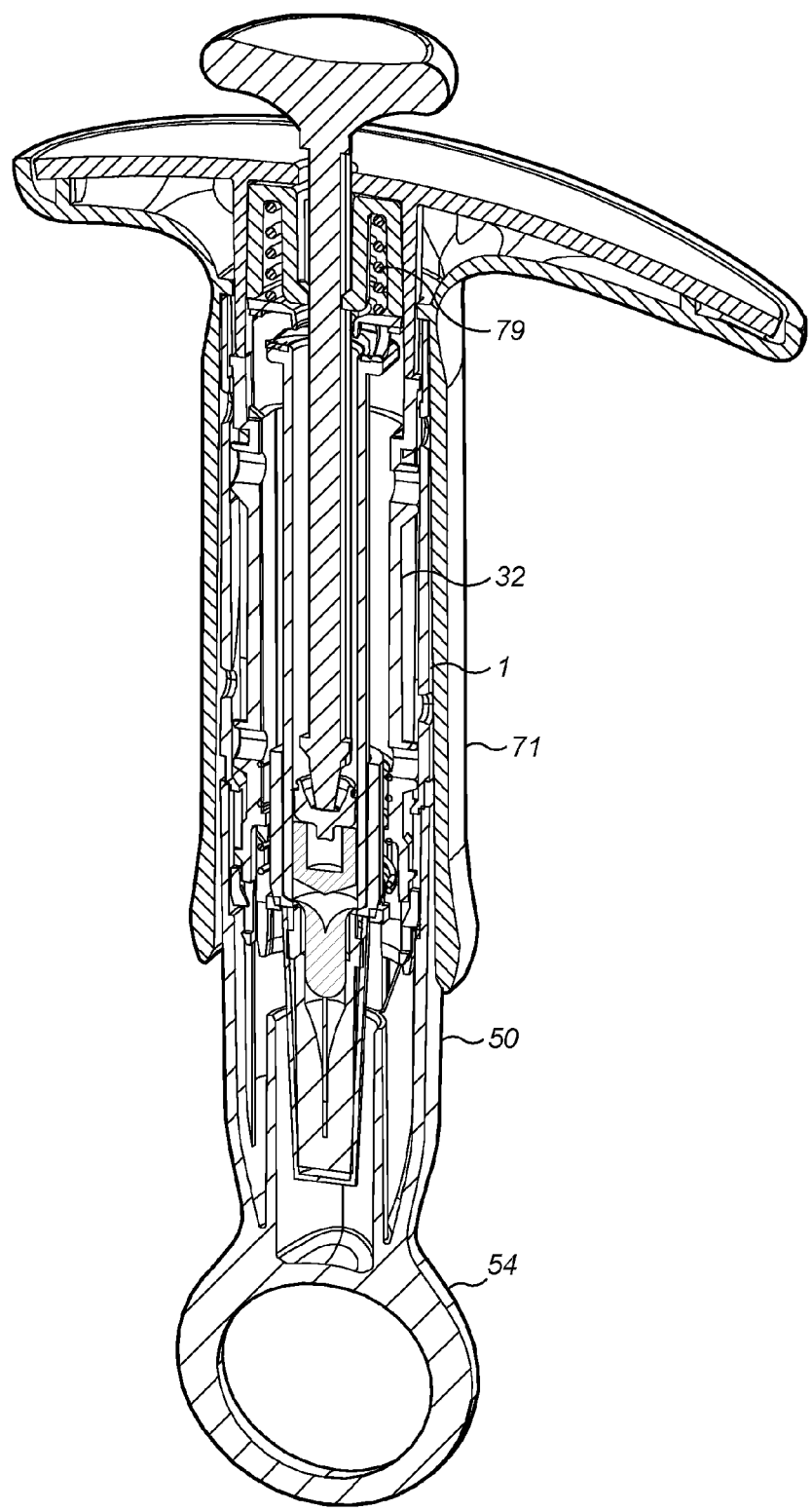
Figure 28F:
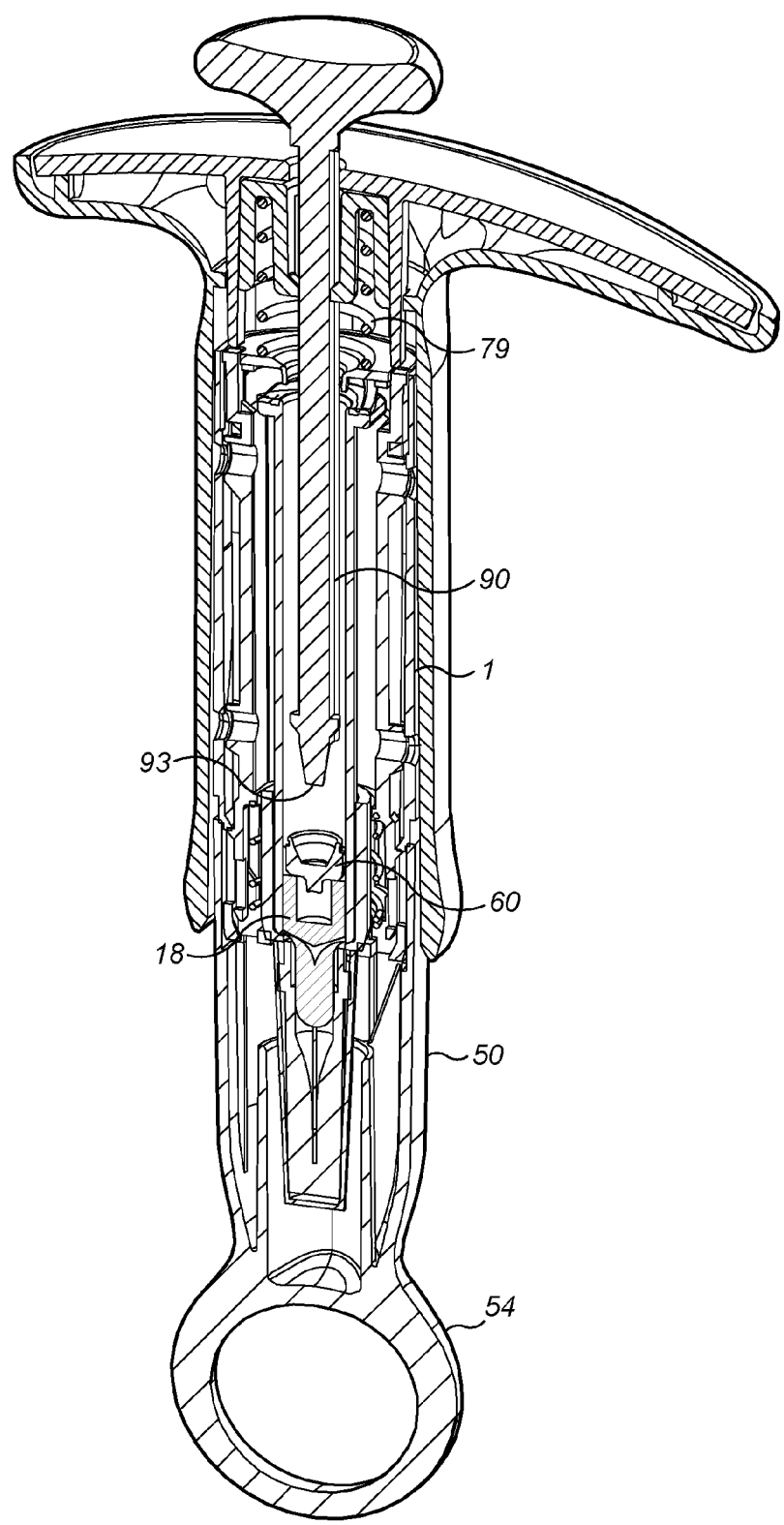

Thus, in a fourth stage of a typical use operation, as shown at FIG. 28*e*, the cap 50 with needle sheath 17 and rigid needle shield 19 has now been replaced on the cassette unit 1 following completion of the injection procedure. In this position, and as previously described in relation to FIGS. 8*b*, 9*c*, 10*c* and 11*c*, the shuttle lock control 32 is in the third 'cassette used' position, locating intermediate the first and second shuttle lock control positions The inner face of the locking arm 26 of the cassette unit housing 20 is again blocked, thereby preventing any inwards movement thereof and so effectively also thereby, preventing any disengagement of the angled tip 29 of that locking arm 26 from socket through-hole 52 of the removable cap 50. In this position, ejector spring 79 is noted to be in a compressed state.

To remove the cassette unit 1 from the manual drive unit 70, the user manually presses on engaging tip 95 of locking arm 94 (e.g. see FIG. 25) to move engaging tips 95 of locking arms 94 out of locking engagement with the latching ledge 96 of window 86 of the manual drive unit housing 71, thus allowing the cassette unit 1 to be released from the cassette unit manual drive unit housing 71. The cassette unit 1 now experiences the forward biasing action of spring 79, which urges the cassette unit 1 forwards and out of the manual drive unit housing to the 'cassette unit ejected' position of FIGS. 28e and 27. In this position, it will also be noted that drive tip 93 of drive rod 90 is now spaced from plunger slaving part 60, but that that plunger slaving part 60 and plunger 18 remain at their forwards most position within the syringe barrel.

The cassette unit 1 is now removed from the manual drive unit housing 71 to leave the manual drive unit in the 'ready to use' position of FIG. 28a. The used cassette unit 1 is typically discarded.

Figure 31:
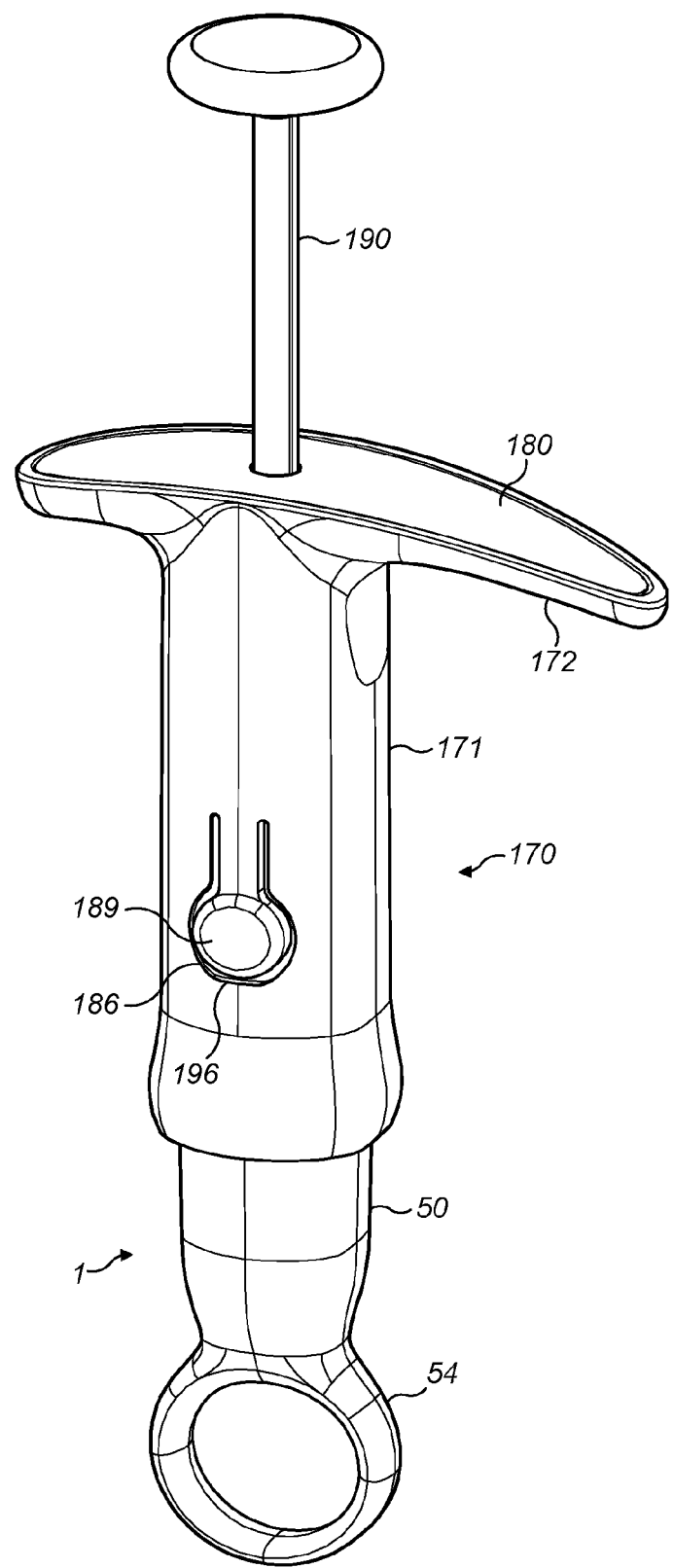
FIG. 31 is a perspective view of a second manual drive unit, particularly suitable for use with the cassette unit of FIGS. 1 to 4.

FIG. 31 shows a perspective view of a second manual drive unit 170 herein for use with the cassette unit 1 as previously described. The second manual drive unit 170 may be appreciated to be a variant of the first manual drive unit 70, and thus also comprises a partly tubular form manual drive unit housing 171 that is sized and shaped at its forward end for receipt of a generally tubular form cassette unit 1. The housing 171 defines a handle 172 arranged for ease of holding by the fingers of a user, which is provided with a top cover 180. The manual drive unit housing 171 is provided with a manually operable drive transfer element in the form of a drive rod 190.

The manual drive unit housing 171 is further provided with a shaped opening 186 defining a latching ledge 196 arranged for interaction with flexible locking arm features 94 (not clearly visible on FIG. 31, but of corresponding form to those shown at FIG. 25 in relation to the first manual drive unit 70) on the cassette unit 1 for reversibly locking the cassette unit 1 there within at the docking position. The manual drive unit housing 171 is further provided with a flexible push arm 189 generally locating above the shaped opening 186.

FIG. 31 shows the second manual drive unit 170 having received a representative cassette unit 1 at the docking position, wherein ring pull 54 of the removable cap 50 protrudes from the manual drive unit housing 171. As so-received within the second manual drive unit 170, the cassette unit 1 is selectively locked therein by the interaction of engaging tips 95 of locking arms 94 of the cassette unit 1 with the latching ledge 196 (not visible, but refer to FIG. 25, which shows a corresponding interaction) of shaped opening 186 of the manual drive unit housing 171. As with the first manual drive unit 70 shown at FIG. 25, the locking arms 94 are arranged to flex into the cassette unit locking position (i.e. with latching engagement of engaging tips 95 of locking arms 94 with the latching ledge 196 of shaped opening 186) on insertion of the cassette unit 1 into the manual drive unit 70 at the docking position.

During use, the cap 50 is removed to expose the needle 14 and needle tip 15 of the syringe 10 (corresponding to what is shown at FIG. 26 in relation to the first manual drive unit 70).

After use of the second manual drive unit 170, and replacement of the cap 50, the user manually pushes/flexes the flexible push arm 189 inwards, thereby also pushing the locking arms 94 inwards and so allowing the engaging tips 95 thereof to move out of latching engagement with latching ledge 196 of shaped opening 186. As with the first manual drive unit 70, the cassette unit 1 is then ejected from the manual drive unit housing 170 (in embodiments, under the action of a spring, not visible) to a cassette unit 1 ejected position (corresponding to FIG. 27 in relation to the first manual drive unit 70).

Figure 32:
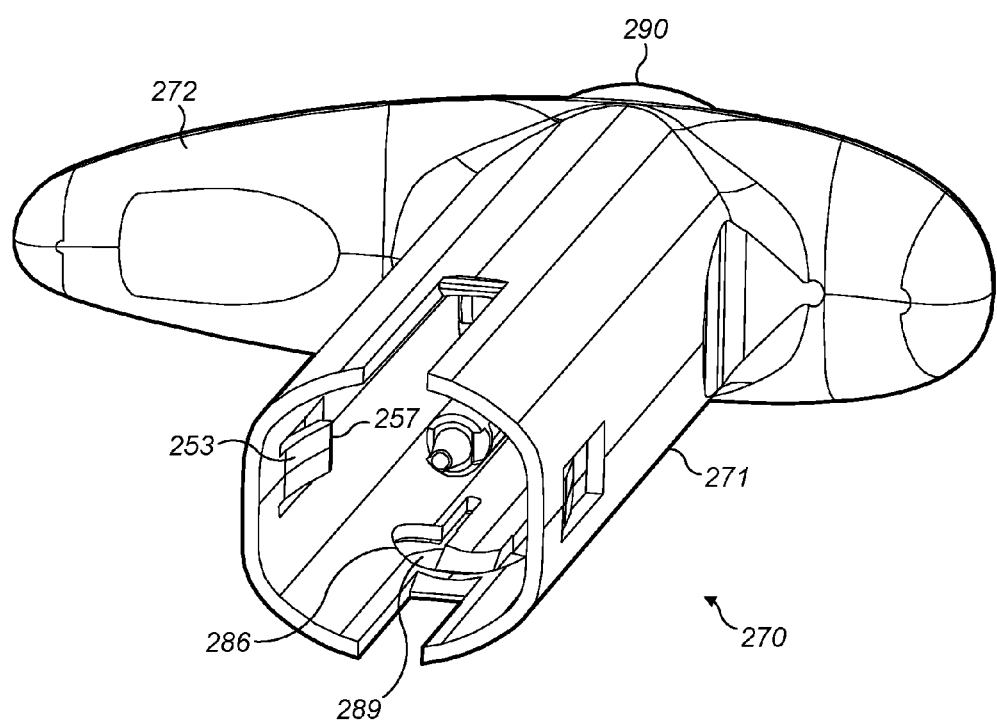
FIG. 32 is a perspective view of a third manual drive unit, particularly suitable for use with the cassette unit of FIGS. 1 to 4, and shown absent its forward end cover.
Figure 33:
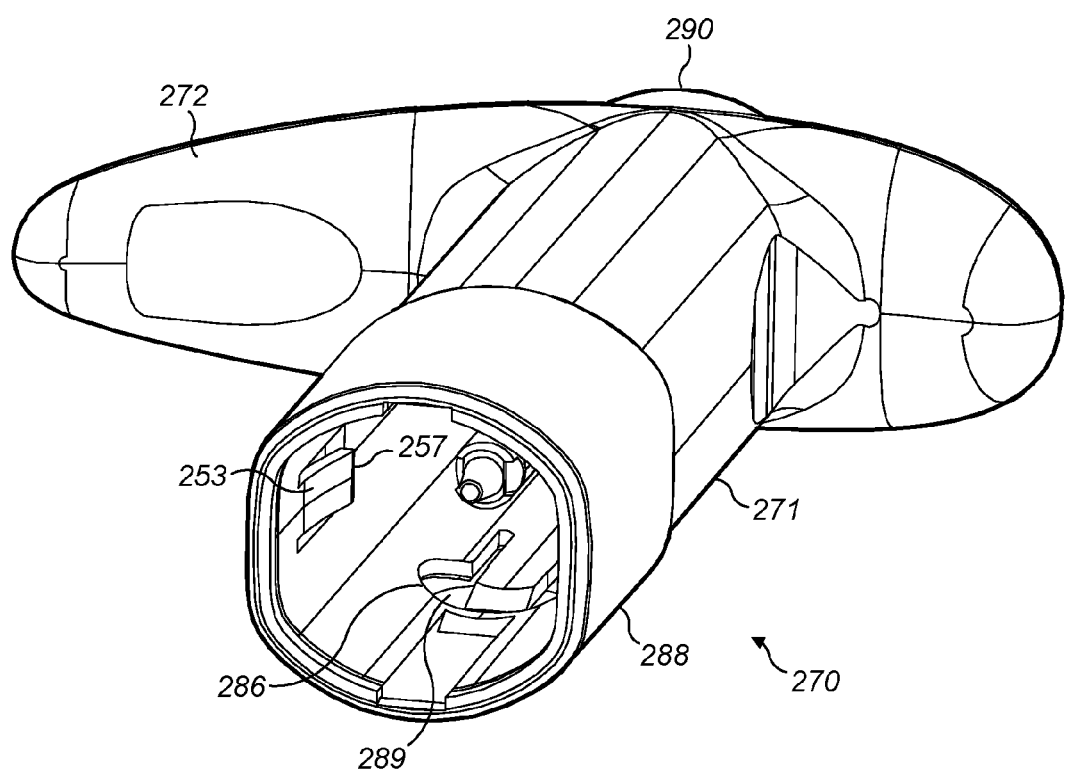
FIG. 33 is a perspective view of the third manual drive unit of FIG. 33, now shown with its forward end cover in place.

FIGS. 32 and 33 show perspective views of a third manual drive unit 270 herein for use with the cassette unit 1 as previously described, wherein in FIG. 32 the third manual drive unit 270 is shown for illustrative purposes only absent its forward end cover 288, and in FIG. 33, the forward end cover 288 is shown in place. The second manual drive unit 270 may be appreciated to be a variant of the first and second manual drive units 70; 170, and thus also comprises a partly tubular form manual drive unit housing 271 that is sized and shaped at its forward end for receipt of a generally tubular form cassette unit 1. The housing 271 defines a handle 272 arranged for ease of holding by the fingers of a user, which is provided with a top cover 280 (see FIG. 34a). The manual drive unit housing 271 is provided with a manually operable drive transfer element in the form of a drive rod 290.

The forward end cover 288 fits over the forward end of the manual drive unit housing 271 and acts in use, to assist the user to position a 45° injection angle. The forward end cover 288 also acts to cover up the end detail of the manual drive unit housing 271 and assists with snug receipt of the cassette unit 1. In addition, the forward end cover acts to cover up access (e.g. undesirable user finger access) from out-with the manual drive unit housing 271 to the cassette unit securing arms 253.

The third manual drive unit housing 271 is further provided with a shaped opening 286 defining a latching ledge 296 (see FIG. 34a) arranged for interaction with flexible locking arm features 94 (not visible on FIGS. 32 and 33, but of corresponding form to those shown at FIG. 25 in relation to the first manual drive unit 70) on the cassette unit 1 for reversibly locking the cassette unit 1 there within at the docking position. The third manual drive unit housing 271 is further provided with a flexible push arm 289 (having identical form to that flexible push arm 189 of the second manual drive unit 170 as shown at FIG. 31) generally locating above the shaped opening 286.

The third manual drive unit housing 271 is further provided with upwardly and inwardly protruding cassette unit securing arms 253 having securing tips 257, which as will be described hereinafter, are arranged to provide a safety function during use, by preventing removal of an uncapped cassette 1 from the third manual drive unit housing 271.

Figure 34A:
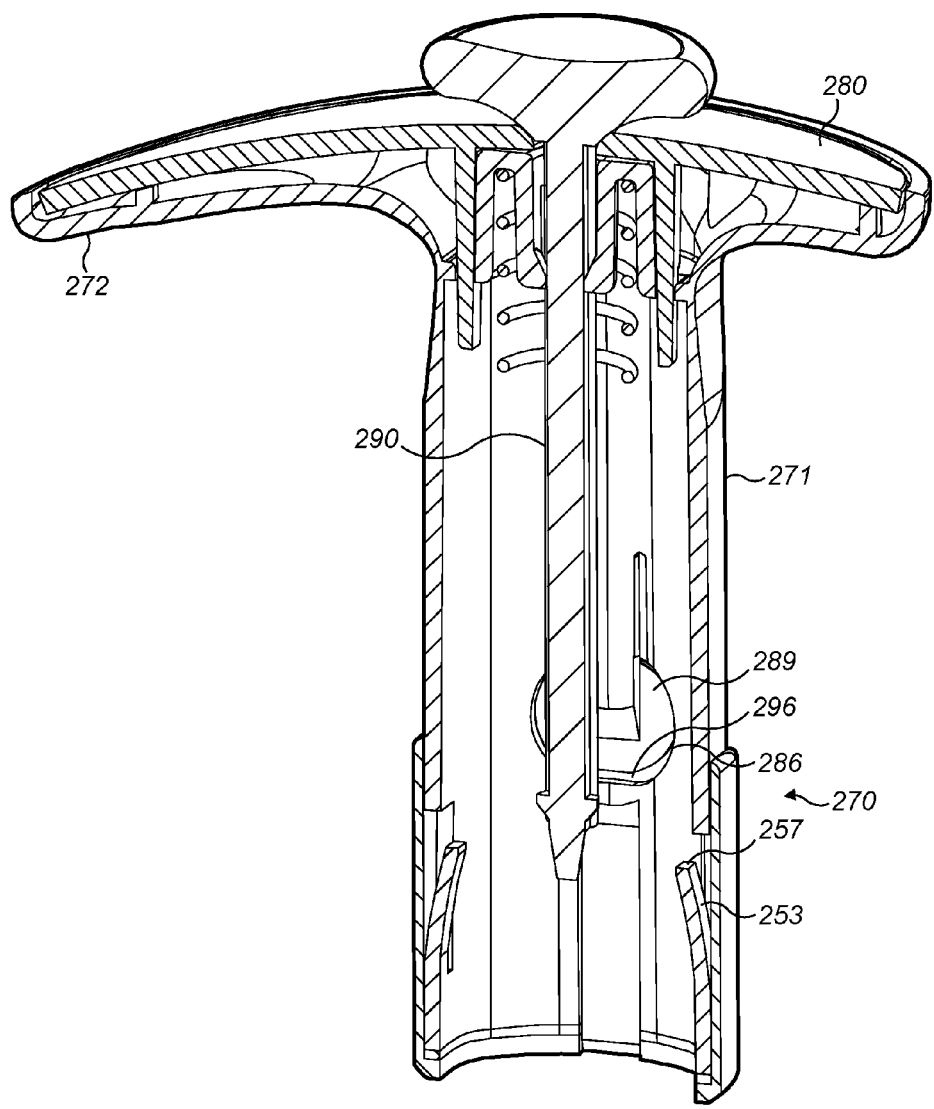
FIGS. 34a to 34c show front cross-sectional views of sequential stages of preparing for injecting use of the third manual drive of FIG. 33 with the cassette unit of FIGS. 1 to 4.
Figure 34B:
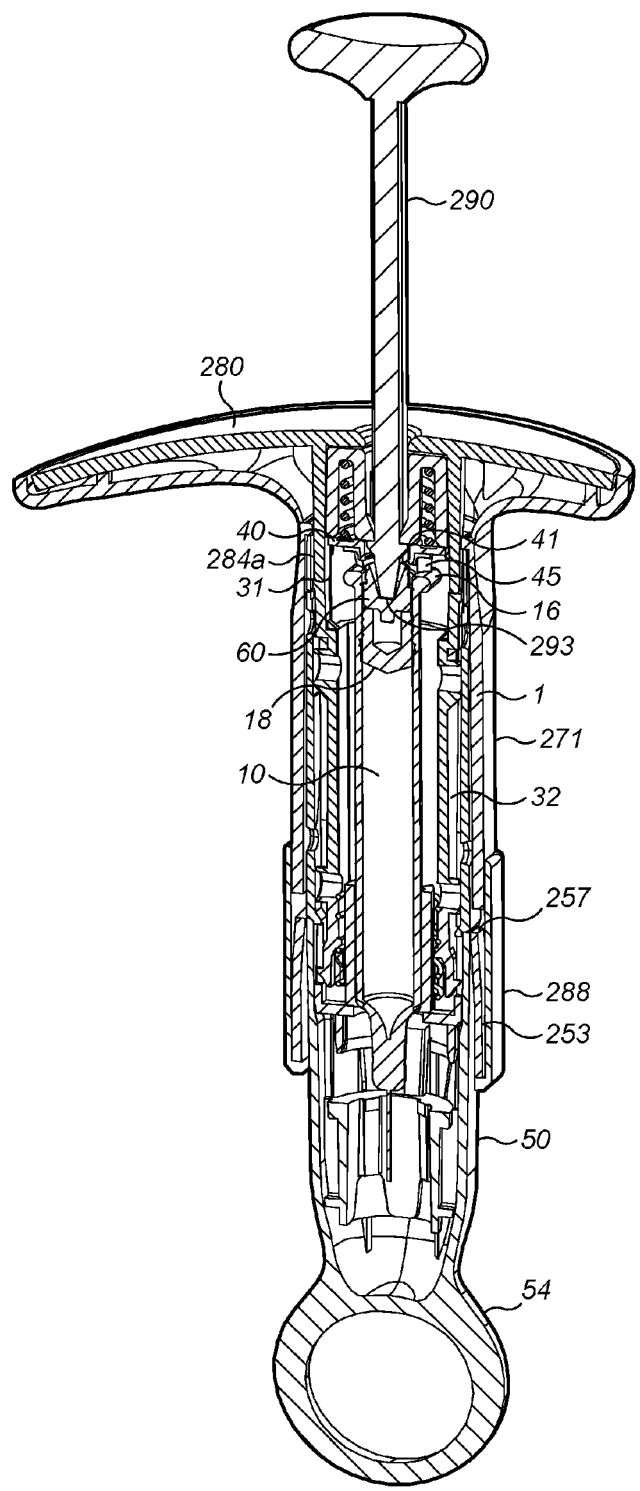
Figure 34C:
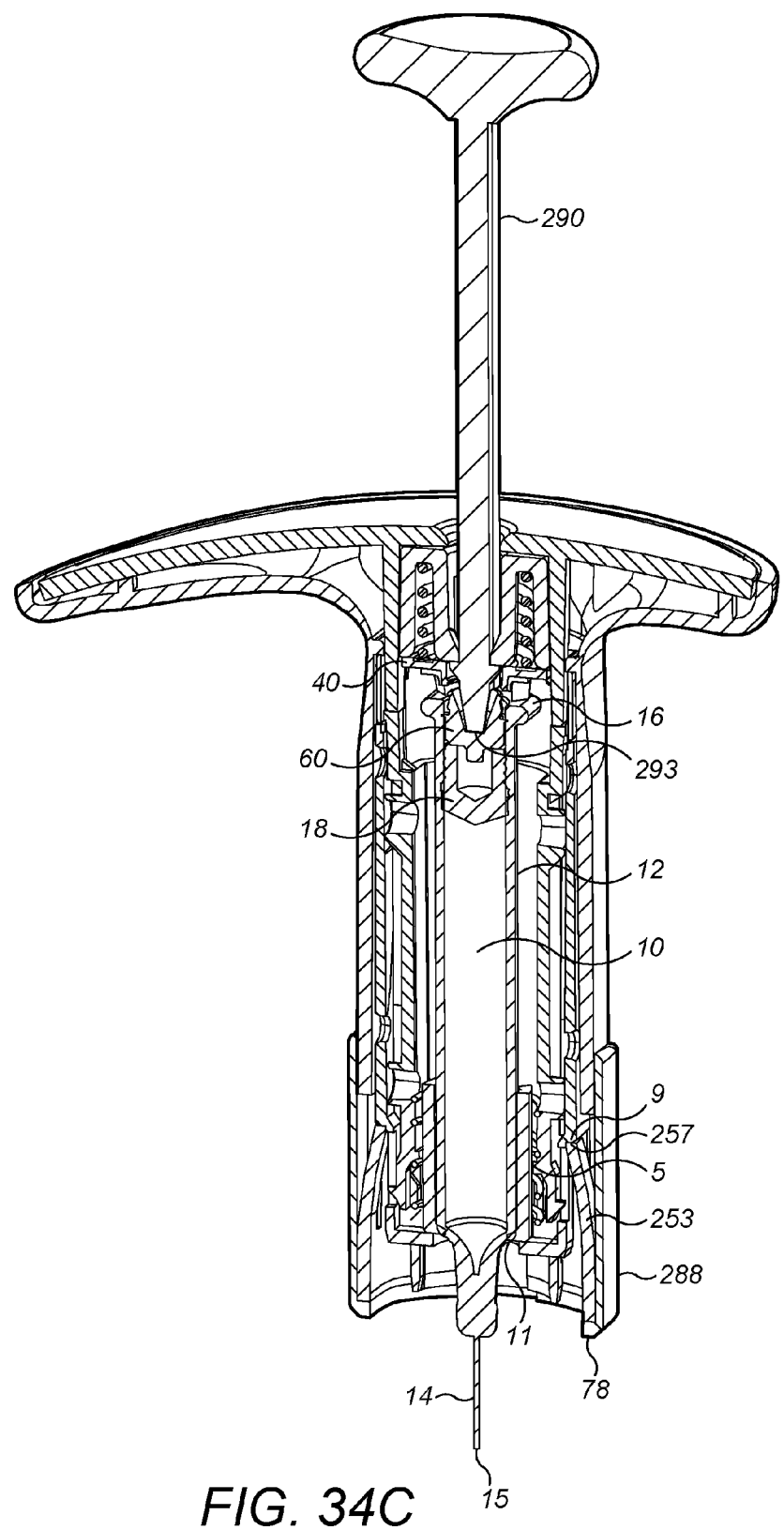

Aspects of preparing the third manual drive unit herein for injecting use with a cassette unit 1 may now be appreciated by reference to FIGS. 34a to 34c and to the following description of a typical preparation for injecting use operation. For clarity, only those aspects of FIGS. 34a to 34c, which are most relevant to the use operation being described, are identified by labelling.

The third manual drive unit 270 and cassette unit 1 are typically supplied as separate entities for assembly by the user into a use configuration. FIG. 34a shows a third manual drive unit 270 with the drive rod 290 at its forward most extent within the third manual drive unit housing 271 and ready to receive a cassette unit 1. In the position as shown at FIG. 34a, before receiving a cassette 1, the cassette unit securing arms 253 having securing tips 257 may be seen to protrude upwardly and inwardly into the third manual drive unit housing 271.

In a first stage of a typical preparing for injecting use operation, as shown at FIG. 34b, the user inserts cassette unit 1 comprising syringe 10 and having removable cap 50 to the docking position within the manual drive unit housing 271 of the third manual drive unit 270.

In the docking position, drive tip 293 of drive rod 290 is received within the drive transfer element-receiving opening 41 of the cassette unit end-cap 40. End-cap spring 45 defines a sprung biasing relationship between the cassette unit end-cap 40 and the flange 16 of the syringe 10, thereby urging the syringe 10 forwards in relation to the cassette unit end cap 40. Plunger slaving part 60 is in releasable engagement with the cassette unit end-cap 40. During injecting use, the plunger slaving part 60 is subsequently released from the cassette unit end-cap 40 in response to forward axial drive provided by the drive rod 290 to a rear drive-receiving face thereof.

As also shown at FIG. 34b, in the docking position, the shuttle lock control 32 is in the second 'cassette unlocked' position (having been pushed relatively forward by the interaction of protruding arms 31 with defining forwardly protruding arms 284a (only one labelled) of the cap lock release feature of the top cover 280 and thus, the removable cap 50 is in the cap unlocked position.

As shown more clearly at FIGS. 9b, 10b and 11b in relation to the first manual drive unit 70, in the 'cap unlocked' position the inner face of the locking arm 26 of the cassette unit housing 20 is no longer blocked. As a result, inwards movement of the locking arm 26 is no longer prevented and disengagement of the tip 29 of the locking arm 26 from socket through-hole 52 of the removable cap 50 is achievable by suitable inwards pushing action on the tip 29/locking arm 26. Such inward pushing action on the locking arm 26 is achievable by pulling the cap 50 away from the cassette unit 1, which results in the angled tip 29 interacting with the wall edges of the socket through-hole 52 to push the locking arm 26 inwards.

As further shown at FIG. 34b, in the docking position, the cassette unit securing arms 253 having securing tips 257 have been pushed outwards by interaction with the upper walls of the removable cap 50 of the cassette 1.

In a second stage of a typical preparing for injecting use operation, as shown at FIG. 28c, the user has removed the cap 50 together with needle sheath 17 and rigid needle shield 19. The needle 14 with tip 15 of the syringe 10 is now uncovered and protrudes from the needle delivery aperture 278 of the third manual drive unit housing 271. This corresponds to the 'ready to inject' position.

As further shown at FIG. 34c, in the 'ready to inject' position, the cassette securing arms 253 are no longer pushed outwards by interaction with the cap 50 (which has been removed, so that the cassette is uncapped) and therefore spring back to their initial position (of FIG. 34a) of protruding upwardly and inwardly into the third manual drive unit housing 271. It may therefore be seen that the securing tips 257 of the securing arms 253 abut the leading end wall 9 of the cassette unit housing 20, thereby preventing removal of the cassette unit 1 from the manual drive unit housing during the drug ejection steps of the injection procedure. Such cassette unit 1 securing action is only released when the cap 50 is removed after the injection procedure, when the cassette unit securing arms 253 revert to their pushed outwards configuration (i.e. as shown at FIG. 34b).

Once the injector is at the 'ready to inject' position of FIG. 34c, ejection of drug from the syringe barrel 12 can commence. Such ejection is in response to manual driving forwards of drive rod 290 by the user. Typical manual drive actions are shown by reference to FIGS. 29 and 30, which show corresponding actions in relation to use of the second manual drive unit 170.

After completion of an injection operation using the third manual drive unit 270, and also after replacement of the cap 50, the user manually pushes/flexes the flexible push arm 289 inwards, thereby also pushing the locking arms 94 inwards and so allowing the engaging tips 95 thereof to move out of latching engagement with latching ledge 296 of shaped opening 286. As with the first and second manual drive units 70; 170, the cassette unit 1 is then ejected from the third manual drive unit housing 270 (in embodiments, under the action of a spring, not visible) to a cassette unit 1 ejected position (corresponding to FIG. 27 in relation to the first manual drive unit 70).

The injector of the invention is suitable for the injected delivery of drug, particularly for the treatment and/or prophylaxis of a number of diseases, disorders or conditions, including infections (viral, e.g. HIV infection, bacterial, fungal and parasitic); endotoxic shock associated with infection; inflammatory diseases/autoimmunity such as osteoarthritis, rheumatoid arthritis, psoriatic arthritis, systemic lupus erythematosus (SLE), ankylosing spondilitis, COPD, asthma, Alzheimer's Disease, Crohn's disease, ulcerative colitis, irritable bowel syndrome and psoriasis; immune mediated inflammatory disorders of the central and peripheral nervous system such as multiple sclerosis and Guillain-Barr syndrome; graft-versus-host disease; organ transplant rejection; pain; cancer (including solid tumours such as melanomas, hepatoblastomas, sarcomas, squamous cell carcinomas, transitional cell cancers, ovarian cancers and hematologic malignancies, acute myelogenous leukaemia, chronic myelogenous leukemia, gastric cancer and colon cancer); congenital disorders, e.g. cystic fibrosis and sickle cell anaemia; growth disorders; epilepsy; treatment of infertility; heart disease including ischaemic diseases such as myocardial infarction as well as atherosclerosis and intravascular coagulation; bone disorders such as osteopenia and osteoporosis; and metabolic/idiopathic disease, e.g. diabetes.

In embodiments, the syringe of the injector herein contains a liquid drug formulation, which is designed for refrigerated rest (e.g. at from 2-8° C.) and for injected delivery at room temperature (e.g. at or about 18-30° C.). In embodiments, the viscosity of the liquid drug formulation is less than 120 mPa·s (120 centipoise), in embodiments less than 100 mPa·s (100 centipoise) at a delivery temperature of 20° C.

Appropriate drugs may thus be selected from biologically active agents, including chemical entities, polysaccharides, steroids and, especially, naturally occurring and recombinant proteins, including glycoproteins, polypeptides and oligopeptides and polymeric derivatives thereof. Particular proteins, polypeptides and oligopeptides include hormones, such as insulin, epinephrine, norepinephrine, adrenocorticotrophin, somatotropin, erythropoietin and oxytocin; cytokines, such as lymphokines, chemokines and interleukins and receptors therefor, e.g. interleukin (IL)-1α, IL-1β, IL-2, IL-3, IL-4, IL-5, IL-6, IL-13, IL17, interferon (IFN)-α, IFN-β, IFN-γ, granulocyte, monocyte colony stimulating factor, tumour necrosis factor-a; growth factors, such as nerve growth factor and platelet-derived growth factor; enzymes, such as tissue plasminogen activator; and, especially, immunoglobulins. Immunoglobulins include whole antibodies and functionally active fragments and/or derivatives thereof, for example polyclonal, monoclonal, recombinant, multi-valent, mono- or multi-specific, humanised or chimeric antibodies, single chain antibodies, Fab fragments, Fab' and F(ab')$_2$ fragments. Polymeric derivatives of such proteins, polypeptides and oligopeptides include derivatives formed between the protein, polypeptide or oligopeptide and a naturally occurring or synthetic polymer, e.g. a polysaccharide or a polyalylklene polymer such as a poly(ethyleneglycol) [PEG] or derivative thereof, e.g. methoxypoly (ethyleneglycol) [mPEG]. Particular agents include growth hormones and hormones for the treatment of infertility. Other particular agents are for the treatment of epilepsy such as brivaracetam and seletracetam.

The injector device herein has been found to be of particular utility where the drug is an immunoglobulin or a fragment thereof, especially a PEGylated or mPEGylated antibody fragment.

The liquid drug formulations herein are typically aqueous formulations, which comprise the drug in solution and additionally other optional formulation components, which may include buffers (e.g. lactate, acetate), NaCl, and pH modifiers (e.g. NaOH).

The injector device herein has been found to be of particular utility wherein the concentration of the drug (e.g. a therapeutic biologic type drug) in the liquid drug formulation is quite high. In particular, where the drug is a pegylated antibody the injector device has been found to be of particular utility wherein the concentration of the drug is greater than 100 mg/ml, particularly greater than 150 mg/ml such as 200 mg/ml.

It is to be understood that the foregoing description is merely illustrative and is not to be limited to the details given herein. While several embodiments have been provided in the present disclosure, it should be understood that the disclosed systems, devices, and methods, and their components, may be embodied in many other specific forms without departing from the scope of the disclosure.

Variations and modifications will occur to those of skill in the art after reviewing this disclosure. The disclosed features may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented. Examples of changes, substitutions, and alterations are ascertainable by one skilled in the art and could be made without departing from the scope of the information disclosed herein. All references cited herein are incorporated by reference in their entirety and made part of this application.

The application of which this description and claims form part may be used as a basis for priority in respect of any subsequent application. The claims of such subsequent application may be directed to any feature or combination of features described herein. They may take the form of product, method or use claims and may include, by way of example and without limitation, one or more of the following claims.

The invention claimed is:

1. A manual drive unit for use with a cassette unit comprising a cassette unit housing containing there within a syringe comprising a barrel; a hollow needle at a front end of said barrel; and a plunger that is axially movable within the barrel, the manual drive unit comprising:

a manual drive unit housing defining a docking cavity and a needle delivery aperture, wherein said docking cavity is arranged for docking receipt of said cassette unit at a docking position; and received by said manual drive unit housing and axially movable relative thereto, a manually operable drive transfer element for transferring axial drive to the plunger of the syringe for moving the plunger into the barrel of the syringe to eject at least part of a volume of liquid drug formulation, wherein the manual drive unit housing defines a handle arranged for ease of holding by fingers of a user, wherein the handle of the manual drive unit housing defines a handle body, and said handle body is provided with a top cover, and wherein the handle body and/or the top cover is provided with a cap lock release feature defining forwardly protruding elements arranged for pushing interaction with a cap lock feature of the cassette unit.

2. The manual drive unit according to claim 1, wherein said manual drive unit housing defines a drive aperture for receipt of said drive transfer element.

3. The manual drive unit according to claim 1, wherein the drive transfer element is provided with a first retaining feature arranged for retaining interaction with a second retaining feature of the manual drive unit housing such as to retain the drive transfer element in movable relationship to the manual drive unit housing.

4. The manual drive unit according to claim 3, wherein said retaining interaction acts to limit an extent of axial driving movement of the drive transfer element relative to the manual drive unit housing.

5. The manual drive unit according to claim 1, wherein the drive transfer element defines a drive shaft having a drive head and a drive tip.

6. The manual drive unit according to claim 5, wherein a first retaining feature is provided to said drive shaft adjacent to said drive tip.

7. The manual drive unit according to claim 1, wherein said manual drive unit housing is provided with one or more cassette unit locking features for reversibly locking the cassette unit there within at said docking position.

8. The manual drive unit according to claim 7, wherein the manual drive unit housing is provided with a flexible push arm arranged for pushing interaction with said one or more cassette unit locking features.

9. The manual drive unit according to claim 1, wherein said manual drive unit housing is provided with a biasing element arranged to bias the cassette unit away from the docking position towards a cassette ejected position.

10. The manual drive unit according to claim 1, wherein the manual drive unit housing defines the docking cavity of generally tubular form for docking receipt of the cassette unit having the cassette unit housing of generally tubular form.

11. The manual drive unit according to claim 1, wherein said handle has a first flange and a second flange, thereby defining a handhold.

12. The manual drive unit according to claim 11, wherein the handle defines a first arc forming a bottom surface of the first flange contoured to correspond to a radius of an arc formed by the user's fingers and a second arc forming a bottom surface of the second flange contoured to correspond to a radius of an arc formed by the user's fingers.

13. The manual drive unit according to claim 12, wherein the second arc is shaped flatter than the first arc.

14. The manual drive unit according to claim 12, wherein the second flange is from 1.3 to 1.7 times as long as the first flange.

15. The manual drive unit according to claim 1, wherein said top cover has a plurality of first mating features adapted to mate with a set of corresponding second mating features formed on the handle body.

16. The manual drive unit according to claim 1, wherein the top cover includes an aperture for receiving the drive transfer element.

17. The manual drive unit according to claim 1, wherein the handle body includes an aperture for receiving the drive transfer element.

18. The manual drive unit according to claim 1, wherein the docking cavity of the manual drive unit housing is provided with positioning features for positioning of the cassette unit received thereby.

19. An injector comprising:
(a) a manual drive unit according to claim 1; and
(b) a cassette unit comprising:
a cassette unit housing defining a cassette unit housing cavity, a rearward entrance to said cassette unit housing cavity and a forward needle projection aperture;
said cassette unit housing cavity in receipt of a syringe comprising:
a barrel for containing a volume of a liquid drug formulation, said barrel defining a flange at a rear end thereof and a forward shoulder at a forward end thereof;
a hollow needle at a front end of said barrel, said hollow needle defining a needle tip for dispensing of said liquid drug formulation; and
a plunger that is axially movable within the barrel,
wherein said plunger of the syringe is arranged for receipt of axial drive from the manually operable drive transfer element for moving the plunger into the barrel of the syringe to eject at least part of said volume of liquid drug formulation.

20. The injector according to claim 19, axially movable within the barrel for forward movement into contact with said plunger, a plunger slaving part arranged for receipt of axial drive from the manually operable drive transfer element and to transfer said axial drive to the plunger for moving the plunger into the barrel of the syringe to eject at least part of said volume of liquid drug formulation.

21. The injector according to claim 20, wherein said plunger slaving part defines a circumferential wall arranged for frictional sliding relationship with an inner wall of the barrel, a rear drive-receiving face and a front plunger-contacting face.

22. The injector according to claim 21, wherein the front plunger-contacting face of plunger slaving part is arranged for engagement with the plunger.

23. The injector according to claim 19, wherein the cassette unit additionally comprises a removable cap that in a capping position fits over and thereby, acts such as to close off, the needle projection aperture of the cassette unit housing.

24. A manual drive unit for use with a cassette unit comprising a cassette unit housing containing there within a syringe comprising a barrel; a hollow needle at a front end of said barrel; and a plunger that is axially movable within the barrel, the manual drive unit comprising:
a manual drive unit housing defining a docking cavity and a needle delivery aperture, wherein said docking cavity is arranged for docking receipt of said cassette unit at a docking position; and
received by said manual drive unit housing and axially movable relative thereto, a manually operable drive transfer element for transferring axial drive to the plunger of the syringe for moving the plunger into the barrel of the syringe to eject at least part of a volume of liquid drug formulation,
wherein the manual drive unit housing is provided with one or more cassette unit securing arms arranged to prevent removal of an uncapped cassette unit therefrom, and
wherein the one or more cassette unit securing arms interact with a removable cap of the cassette unit such that when the removable cap is in place, the one or more cassette unit securing arms are displaced to a cassette unit non-securing position, and when the removable cap is not in place, the one or more cassette unit securing arms are in a cassette unit securing position.

25. An injector comprising:
(a) a manual drive unit for use with a cassette unit comprising a cassette unit housing containing there within a syringe comprising a barrel; a hollow needle at a front end of said barrel; and a plunger that is axially movable within the barrel, the manual drive unit comprising:
a manual drive unit housing defining a docking cavity and a needle delivery aperture, wherein said docking cavity is arranged for docking receipt of said cassette unit at a docking position; and
received by said manual drive unit housing and axially movable relative thereto, a manually operable drive transfer element for transferring axial drive to the plunger of the syringe for moving the plunger into the barrel of the syringe to eject at least part of a volume of liquid drug formulation;
(b) a cassette unit comprising:
a cassette unit housing defining a cassette unit housing cavity, a rearward entrance to said cassette unit housing cavity and a forward needle projection aperture, said cassette unit housing cavity in receipt of a syringe comprising:
a barrel for containing a volume of a liquid drug formulation, said barrel defining a flange at a rear end thereof and a forward shoulder at a forward end thereof;
a hollow needle at a front end of said barrel, said hollow needle defining a needle tip for dispensing of said liquid drug formulation; and
a plunger that is axially movable within the barrel, wherein said plunger of the syringe is arranged for receipt of axial drive from the manually operable drive transfer element for moving the plunger into the barrel of the syringe to eject at least part of said volume of liquid drug formulation; and
in capping relationship with said rearward entrance of the cassette unit housing, a cassette unit end-cap, said cassette unit end-cap defining a drive transfer element-receiving opening for receipt of the drive transfer element.

26. An injector comprising:
(a) a manual drive unit for use with a cassette unit comprising a cassette unit housing containing there within a syringe comprising a barrel; a hollow needle at a front end of said barrel; and a plunger that is axially movable within the barrel, the manual drive unit comprising:

a manual drive unit housing defining a docking cavity and a needle delivery aperture, wherein said docking cavity is arranged for docking receipt of said cassette unit at a docking position; and received by said manual drive unit housing and axially movable relative thereto, a manually operable drive transfer element for transferring axial drive to the plunger of the syringe for moving the plunger into the barrel of the syringe to eject at least part of a volume of liquid drug formulation;

(b) a cassette unit comprising:

a cassette unit housing defining a cassette unit housing cavity, a rearward entrance to said cassette unit housing cavity and a forward needle projection aperture, said cassette unit housing cavity in receipt of a syringe comprising:

a barrel for containing a volume of a liquid drug formulation, said barrel defining a flange at a rear end thereof and a forward shoulder at a forward end thereof;

a hollow needle at a front end of said barrel, said hollow needle defining a needle tip for dispensing of said liquid drug formulation; and a plunger that is axially movable within the barrel, wherein said plunger of the syringe is arranged for receipt of axial drive from the manually operable drive transfer element for moving the plunger into the barrel of the syringe to eject at least part of said volume of liquid drug formulation; and axially movable within the barrel for forward movement into contact with said plunger, a plunger slaving part arranged for receipt of axial drive from the manually operable drive transfer element and to transfer said axial drive to the plunger for moving the plunger into the barrel of the syringe to eject at least part of said volume of liquid drug formulation, wherein in a pre-use configuration, the plunger slaving part is shaped for releasable engagement with a cassette unit end-cap.

27. An injector comprising:

a manual drive unit for use with a cassette unit comprising a cassette unit housing containing there within a syringe comprising a barrel; a hollow needle at a front end of said barrel; and a plunger that is axially movable within the barrel the manual drive unit comprising:

a manual drive unit housing defining a docking cavity and a needle delivery aperture, wherein said docking cavity is arranged for docking receipt of said cassette unit at a docking position; and received by said manual drive unit housing and axially movable relative thereto, a manually operable drive transfer element for transferring axial drive to the plunger of the syringe for moving the plunger into the barrel of the syringe to eject at least part of a volume of liquid drug formulation; and (b) a cassette unit comprising:

a cassette unit housing defining a cassette unit housing cavity, a rearward entrance to said cassette unit housing cavity and a forward needle projection aperture, said cassette unit housing cavity in receipt of a syringe comprising:

a barrel for containing a volume of a liquid drug formulation, said barrel defining a flange at a rear end thereof and a forward shoulder at a forward end thereof;

a hollow needle at a front end of said barrel, said hollow needle defining a needle tip for dispensing of said liquid drug formulation; and a plunger that is axially movable within the barrel, wherein said plunger of the syringe is arranged for receipt of axial drive from the manually operable drive transfer element for moving the plunger into the barrel of the syringe to eject at least part of said volume of liquid drug formulation, wherein the cassette unit additionally comprises a removable cap that in a capping position fits over and thereby, acts such as to close off, the needle projection aperture of the cassette unit housing, and wherein the cassette unit housing is provided with a cap lock feature that is movable from a first cap locking position in which it prevents removal of the removable cap from the cassette unit to a second cap un-locking position in which it no longer prevents such cap removal.

28. The injector according to claim 27, wherein the cap lock feature defines one or more first engagement features arranged for reversibly engaging one or more second engagement features of said removable cap for reversible lock engagement of the removable cap to the cassette unit housing.

29. The injector according to claim 28, wherein the manual drive unit includes a cap lock release feature capable of interacting with said cap lock feature to disengage the one or more first engagement features of the cassette unit housing from the one or more second engagement features of the removable cap when the cassette unit is at the docking position in the drive unit.

30. The injector according to claim 28, additionally comprising a shuttle lock control defining one or more blocking elements for selectively blocking movement of said one or more first engagement features relative to said one or more second engagement features.

31. The injector according to claim 30, wherein said shuttle lock control is axially movable relative to the cassette unit housing between:

(i) a first 'cassette unused' position, in which said one or more blocking elements block movement of the one or more first engagement features relative to the one or more second engagement features, thereby keeping the removable cap in locked relationship to the cassette unit housing;

(ii) a second 'cassette unlocked' position, in which said one or more blocking elements no longer block movement of the one or more first engagement features relative to the one or more second engagement features, thereby allowing for unlocking of the removable cap from the cassette unit housing and for removal and replacement thereof; and (iii) after replacement of the removable cap, a third 'cassette used' position, locating intermediate said first and second positions, in which the one or more blocking elements again block movement of the one or more first engagement features relative to the one or more second engagement features, thereby restoring the locked relationship between the removable cap and the cassette unit housing.

32. The injector according to claim 31, wherein the shuttle lock control of the cassette unit is only movable from the first 'cassette unused' position to the second 'cassette unlocked' position when the cassette unit locates at the docking position within the drive unit housing.

33. The injector according to claim 27, wherein the removable cap is provided with a finger-grip feature that is sized and shaped for gripping by a finger of a user to allow for removal of the removable cap and a needle cover from the cassette unit housing.

34. The injector according to claim 27, additionally comprising a needle cover defining a needle sheath for sheathing of the needle tip of the syringe, wherein the removable cap is provided with a connector defining one or more needle cover gripping elements for gripping the needle cover.

* * * * *